(12) United States Patent
Becker et al.

(10) Patent No.: US 9,382,288 B2
(45) Date of Patent: Jul. 5, 2016

(54) DERIVATIVES OF STEROID BENZYLAMINES, HAVING AN ANTIPARASITIC ANTIBACTERIAL, ANTIMYCOTIC AND/OR ANTIVIRAL ACTION

(75) Inventors: Katja Becker, Wettenberg (DE); Reimar Krieg, Jena (DE); Bruno Schönecker, Jena (DE)

(73) Assignee: Justus-Liebig-Universitat Giessen, Giessen (DE)

( * ) Notice: Subject to any disclaimer, the term of this patent is extended or adjusted under 35 U.S.C. 154(b) by 355 days.

(21) Appl. No.: 13/877,733

(22) PCT Filed: Oct. 6, 2011

(86) PCT No.: PCT/DE2011/001829
§ 371 (c)(1),
(2), (4) Date: Jun. 17, 2013

(87) PCT Pub. No.: WO2012/051988
PCT Pub. Date: Apr. 26, 2012

(65) Prior Publication Data
US 2013/0266645 A1 Oct. 10, 2013

(30) Foreign Application Priority Data
Oct. 6, 2010 (DE) .......................... 102010047714

(51) Int. Cl.
*C07J 11/00* (2006.01)
*A61K 31/56* (2006.01)
*A61K 45/06* (2006.01)
*C07J 41/00* (2006.01)

(52) U.S. Cl.
CPC ............ *C07J 11/00* (2013.01); *A61K 31/56* (2013.01); *A61K 45/06* (2013.01); *C07J 41/005* (2013.01)

(58) Field of Classification Search
CPC ...... C07J 41/0072; C07J 11/00; A61K 31/56; A61K 45/06
See application file for complete search history.

(56) References Cited

U.S. PATENT DOCUMENTS

| | | | |
|---|---|---|---|
| 4,917,826 A | 4/1990 | Johnson et al. | |
| 5,196,542 A * | 3/1993 | Johnson .............. | C07D 213/38 540/107 |
| 5,274,089 A * | 12/1993 | Bundy et al. ................. | 540/112 |
| 5,621,123 A * | 4/1997 | Johnson et al. ............... | 552/522 |

FOREIGN PATENT DOCUMENTS

DE  19633206 A1 * 2/1998

OTHER PUBLICATIONS

Norhayati et al (Medical Journal of Malaysia, Jun. 2003, vol. 58, pp. 296-306).*
Akritidis (Clinical Microbiology and Infection, 2011, vol. 17, pp. 331-335).*
Gros et al (Journal of Medicinal Chemistry, 2006, vol. 49, pp. 6094-6103).*
DE 19633206 a1, English translation from Espacenet, reference date Feb. 1998.*
Rutkowski et al (Experimental Parasitology, Feb. 2007, vol. 115, pp. 143-159).*
Gordi (Clinical Pharmacokinetics of the antimalarial artemisinin based on saliva sampling, Acta Universitatis Upsaliensis, 2001, pp. 1-55).*
International Search Report for PCT/DE2011/001829 mailed on Apr. 26, 2012.

* cited by examiner

*Primary Examiner* — Sean Basquill
*Assistant Examiner* — Mark V Stevens
(74) *Attorney, Agent, or Firm* — Amin, Turocy & Watson LLP

(57) ABSTRACT

The present invention relates to compounds derived from steroids of the general formula (I)

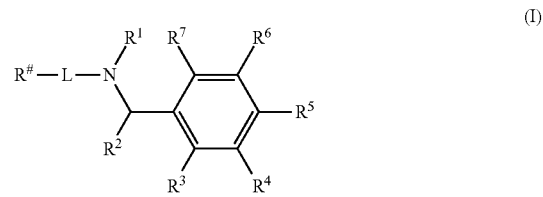

wherein L represents a linker and $R^{\#}$ represents a steroid residue, the use of compounds of the general formula (I) in medicine and for the prophylaxis and/or the treatment of infectious diseases. Furthermore described are pharmaceutical compositions containing at least one compound of the general formula (I). A further aspect of the invention relates to the synthesis of said compounds of the general formula (I).

2 Claims, 4 Drawing Sheets

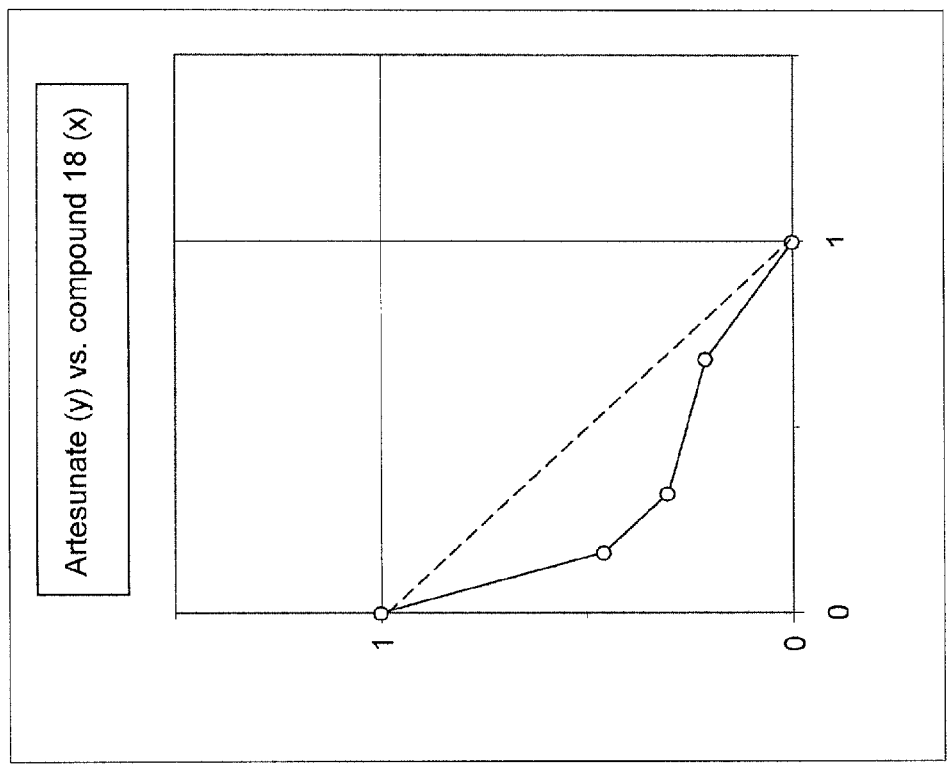
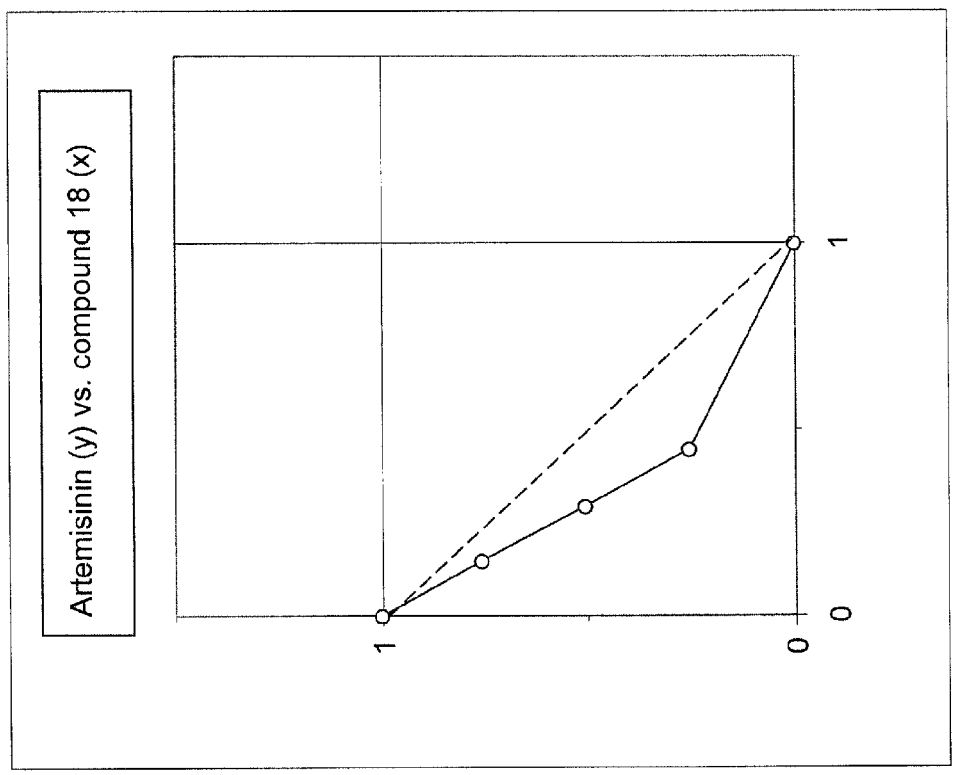
Figure 3

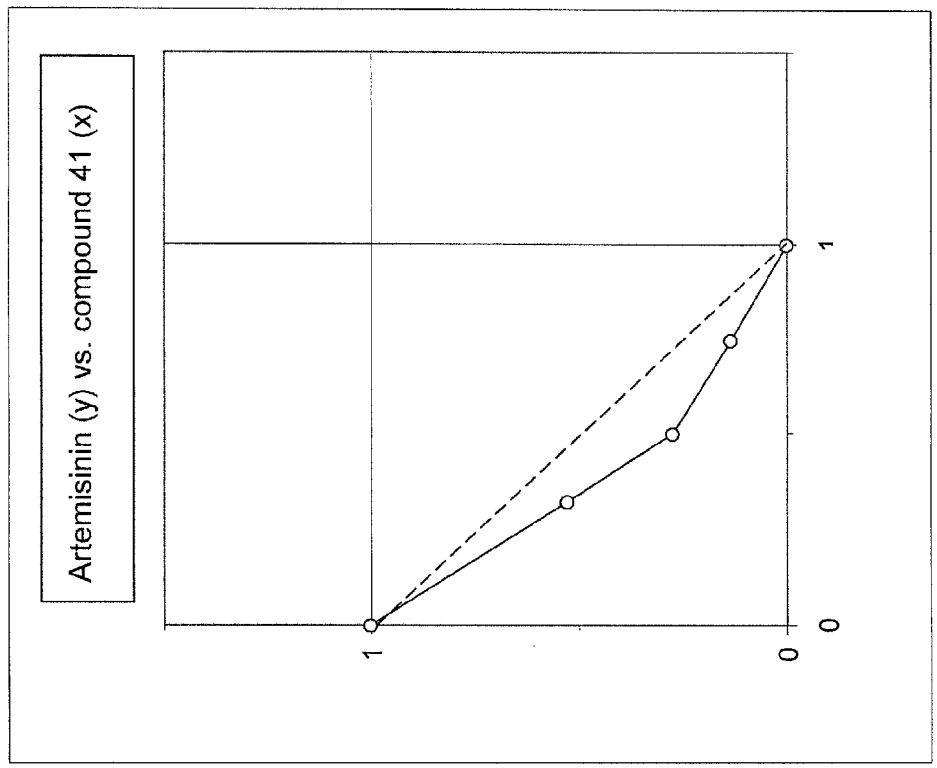
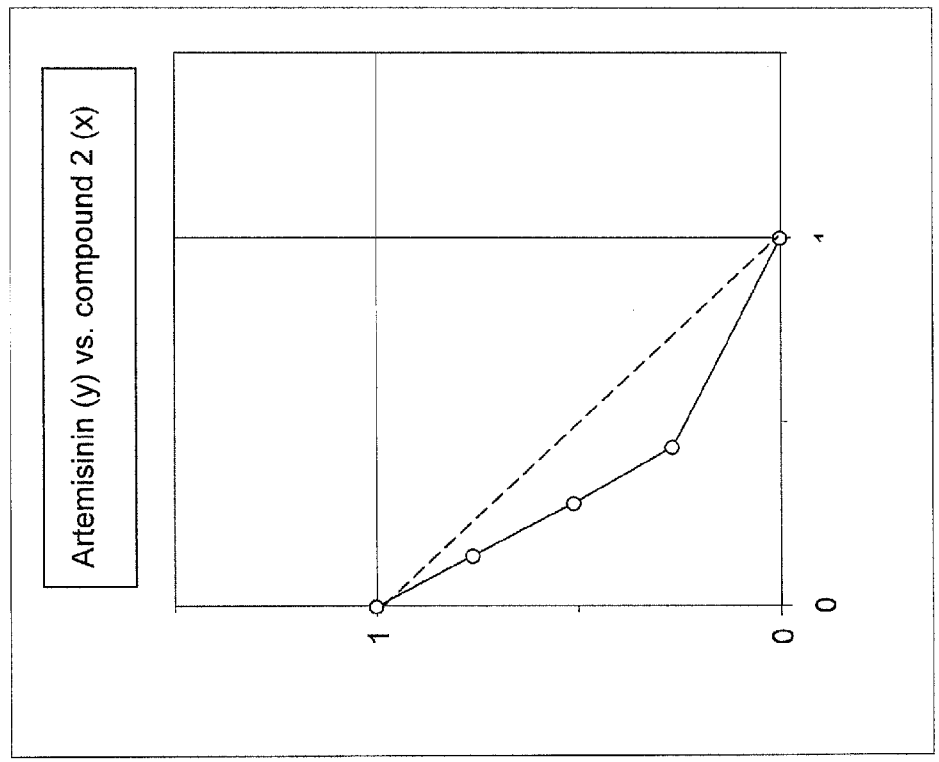
Figure 4

DERIVATIVES OF STEROID BENZYLAMINES, HAVING AN ANTIPARASITIC ANTIBACTERIAL, ANTIMYCOTIC AND/OR ANTIVIRAL ACTION

The invention relates to steroid-derived compounds of the general formula (I); the use thereof in medicine and for the prophylaxis and/or treatment of infectious diseases. Furthermore described are pharmaceutical compositions containing at least one compound of the present invention. Another aspect of the invention relates to the synthesis of compounds of the formula (I).

An infectious disease, colloquially referred to as "infection" or "contagious disease", is a disease caused by a pathogen. An infectious disease however is not to be equated with an infection, since not all infections inevitably lead to a disease. Infectious diseases show a broad range of temporary courses and symptoms, which are often specific for the causative organism. They may be acute and occur within a few days, or develop slowly over weeks, month, sometimes even year. While some infectious diseases are locally confined, others are systemic. Crucial for the course and prognosis of an infectious disease is among others the ability of the immune system to eliminate the pathogen. But the risk associated with an infectious disease also depends on the so-called virulence of the pathogen. If and in which severity grade an infection subsequently leads to an infectious disease is among many other factors also determined by the number of ingested pathogens (minimal infectious dose).

The immune system serves as biological defense system of higher organisms, preventing tissue damage caused by pathogenic organisms. This system destroys aberrant endogenous cells and is furthermore able to destroy and eliminate microorganisms like bacteria, viruses and other parasites or foreign substances which have invaded the body. The immune system represents a complex network of different organs, cell types and molecules.

Despite ambitious vaccination programs, viral infections like influenza, but also infections caused by human immunodeficiency virus ("HIV"), human papilloma virus (HPV types 16 or 18), human cytomegalovirus ("HCMV") or human hepatitis B or C viruses ("HBV", type B; "HCV", type C) remain a frequent cause of life-threatening diseases worldwide and are considered particularly in immunodeficient humans as important cause of disease and death. Even though it could be demonstrated that an antiviral chemotherapy with substances like amantadine and rimantadine is able to reduce the duration of symptoms of clinical infections (e.g. influenza infections), severe side-effects and a fast development of resistant variants were described. New classes of antiviral active substances are currently developed which are in particular targeted against viral proteins like e.g. the influenza neuraminidase. The ability of viruses to quickly alter target proteins by mutation however poses an obstacle for an effective treatment with active substances selectively inhibiting the function of specific, viral polypeptides. Great demand thus exists for new therapeutic strategies suitable for the prevention and treatment of viral infections.

Demand also exists with respect to new therapies for the prevention and treatment of bacterial infections, most of all bacterial infections which are caused by multi-resistant bacteria. Bacterial infections are currently treated with various antibiotics. Even though antibiotics can be highly effective for the treatment of a large variety of bacterial infections, a number of constraints exist concerning the efficacy and safety of antibiotics. Some individuals for example show an allergic reaction to certain antibiotics, while others suffer from severe side-effects. The use of antibiotics for the treatment of bacterial infections furthermore pronounces the development of antibiotic-resistant bacterial strains. Consequently, here also great demand exists for the development of new substances suitable for the treatment of bacterial diseases.

Parasitism is a type of symbiotic relationship between organisms of various species in which one organism, the parasite, lives in or on a host organism and obtains nutrition from and at the expense of the host. Generally, parasites are much smaller than their hosts, show a high degree of specialization for their respective host and the colonization thereof and reproduce faster and in greater numbers than their hosts. Classic examples of parasitism are interactions between vertebrates as hosts and various parasites like unicellular protozoas, multicellular worms (helminths) and arthropods. Examples for parasitic infections in humans are infections caused by protozoa and protists or worm infections. A few parasites transmit disease pathogens to humans which provoke sometimes lethal diseases (parasitoses). A list of parasitic diseases is given further below. The definition parasite also applies to many bacteria and fungi; these are however, due to their medical significance and also on the basis of their partly only facultative parasitism dealt with in own scientific disciplines, namely bacteriology and mycology within the field of microbiology, and are for this reason described separately in this application.

Parasites reduce the host's fitness due to their general pathology, a competition for food, organ damages or behavioral changes. A parasitic infestation of low intensity can often take a harmless course, i.e. without causing major damage, and provoke no lasting symptoms. Medium and severe infections however may cause serious disease patterns, consequently enhancing both morbidity as well as mortality.

*Plasmodium falciparum*, a unicellular parasite belonging to the apicomplexa, is the causative organism of malaria tropica. Malaria is also called marsh fever or intermittent fever. Plasmodia are transmitted by female mosquito bites of which *Anopheles gambiae* represents the most prominent example. After an initial phase in the liver, these parasites live and multiply in red blood cells. The lysis of red blood cells every other day releases new parasites into the blood, thus causing the fever attacks which are characteristic of malaria. To date, roughly 3 billion people in 108 countries live with the risk of a malaria infection. With 240 million malaria cases annually, *P. falciparum* causes up to one million cases of death, whereby Africa is most severely affected, accounting for more than 90% of all deaths. In the year 2004, *P. falciparum* became one of the leading causes for death caused by only a single pathogen worldwide. The onset of chloroquine resistance of the pathogen marked the beginning of a new chapter in the history of malaria in Southeast Asia, and since 1973, chloroquine had to be replaced by a combination of sulphadoxine and pyrimethamine (SP). Since 1985, increasingly mefloquine has been used. The rapid development of resistances against generally used drugs lead to the introduction of other active substances. The therapy regimens for the prevention and treatment of chloroquine-resistant *P. falciparum* are associated with higher costs and more side-effects as compared to chloroquine. Thus measures are urgently needed to develop new effective, affordable and alternative therapies against malaria.

Schistosomatidae are trematodes living in the blood vessels of vertebrates. A water snail serves as intermediate host. Schistosomoses or bilharzioses are important tropical diseases in more than 70 countries. In addition to *S. mansoni*, also *S. haematobium* (only in Africa) and *S. japonicum* (only in Asia) are of major importance. According to estimations of the World Health Organization (WHO), approximately 200 million people are currently infected with schistosomas. The eggs can be detected in the stool (for *S. haematobium* in the urine) and in the blood. In addition to a direct damage of blood vessels and intestinal epithelia caused by migrating eggs, also immunological processes play a role in disease development. These are in particular immune responses against egg antigens. Worm eggs unable to migrate into the intestines are deposited in the liver (and other organs) and are encapsulated by host cells (granuloma formation). This results in organ damages, in particular to liver fibrosis.

The present invention has therefore the object of providing new antiparasitic, antibacterial, antimycotic and/or antiviral drugs.

This object is solved by the technical teaching of the independent claims. Further advantageous embodiments, aspects and details of the invention are derived from the dependent claims, descriptions and examples.

The present inventions relates to compounds of the general formula (I)

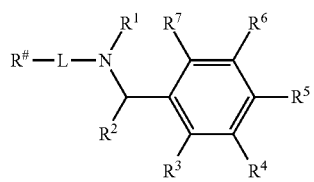

(I)

wherein
L represents a chemical bond or one of the following spacers: —(CH$_2$)$_n$—, —(O—CH$_2$—CH$_2$)$_n$—, —(O—CH$_2$)$_n$—, —(O—CH$_2$—CH$_2$—CH$_2$)$_n$—, —(CH=CH)$_n$—, —(CH$_2$)$_n$—N(R$^8$)—, —(CH$_2$)$_n$—SO$_2$—, —(CH$_2$)$_n$—CO—, —(CH$_2$—CH$_2$—O)$_n$—CH$_2$—CH$_2$—, —(CH$_2$—O)$_n$—CH$_2$—, —(CH$_2$—CH$_2$—CH$_2$—O)$_n$—CH$_2$—CH$_2$—CH$_2$—;

n represents one of the following integers: 0, 1, 2, 3, 4, 5, 6;
R$^\#$ represents a steroid residue;
whereby the steroid residue R$^\#$ may carry a second, third or even forth arylmethylamino fragment of the formula:

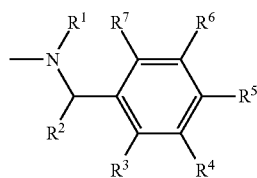

R$^1$, R$^2$, R$^8$ and R$^9$ independently of one another represent the following residues: —H, —C≡CH, —C≡C—CH$_3$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, -cyclo-C$_3$H$_5$, -cyclo-C$_4$H$_7$, -cyclo-C$_5$H$_9$, -cyclo-C$_6$H$_{11}$, —CHO, —CO—CH$_3$, —CO—C$_2$H$_5$, —CO—C$_3$H$_7$;

R$^1$ and R$^2$ together may represent a bond;
R$^1$ and R$^7$ together form a methylene or an ethylene group;
R$^2$ and R$^3$ together form an ethylene or a propylene group;
R$^3$, R$^4$, R$^5$, R$^6$ and R$^7$ independently of one another represent the following residues: —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OPh$_3$, —SH, —SCH$_3$, —SC$_2$H$_5$, —SC$_3$H$_7$, —S-cyclo-C$_3$H$_5$, —SCH(CH$_3$)$_2$, —SC(CH$_3$)$_3$, —NO$_2$, —F, —Cl, —Br, —I, —P(O)(OH)$_2$, —P(O)(OCH$_3$)$_2$, —P(O)(OC$_2$H$_5$)$_2$, —P(O)(OCH(CH$_3$)$_2$)$_2$, —C(OH)[P(O)(OH)$_2$]$_2$, —Si(CH$_3$)$_2$(C(CH$_3$)$_3$), —Si(C$_2$H$_5$)$_3$, —Si(CH$_3$)$_3$, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —O—CO-Ph, —O—CO—CH$_3$, —O—CO—C$_2$H$_5$, —O—CO—C$_3$H$_7$, —O—CO-cyclo-C$_3$H$_5$, —O—CO—CH(CH$_3$)$_2$, —O—CO—C(CH$_3$)$_3$, —O—CO-para-C$_6$H$_4$—OR$^9$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NHCOCH$_3$, —NHCOC$_2$H$_5$, —NHCOC$_3$H$_7$, —NHCO-cyclo-C$_3$H$_5$, —NHCO—CH(CH$_3$)$_2$, —NHCO—C(CH$_3$)$_3$, —NHCO—OCH$_3$, —NHCO—OC$_2$H$_5$, —NHCO—OC$_3$H$_7$, —NHCO—O-cyclo-C$_3$H$_5$, —NHCO—OCH(CH$_3$)$_2$, —NHCO—OC(CH$_3$)$_3$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —SOCH$_3$, —SOC$_2$H$_5$, —SOC$_3$H$_7$, —SO-cyclo-C$_3$H$_5$, —SOCH(CH$_3$)$_2$, —SOC(CH$_3$)$_3$, —SO$_2$CH$_3$, —SO$_2$C$_2$H$_5$, —SO$_2$C$_3$H$_7$, —SO$_2$-cyclo-C$_3$H$_5$, —SO$_2$CH(CH$_3$)$_2$, —SO$_2$C(CH$_3$)$_3$, —SO$_3$H, —SO$_3$CH$_3$, —SO$_3$C$_2$H$_5$, —SO$_3$C$_3$H$_7$, —SO$_3$-cyclo-C$_3$H$_5$, —SO$_3$CH(CH$_3$)$_2$, —SO$_3$C(CH$_3$)$_3$, —SO$_2$NH$_2$, —OCF$_3$, —OC$_2$F$_5$, —O—COOCH$_3$, —O—COOC$_2$H$_5$, —O—COOC$_3$H$_7$, —O—COO-cyclo-C$_3$H$_5$, —O—COOCH(CH$_3$)$_2$, —O—COOC(CH$_3$)$_3$, —NH—CO—NH$_2$, —NH—CO—NHCH$_3$, —NH—CO—NHC$_2$H$_5$, —NH—CO—NHC$_3$H$_7$, —NH—CO—NH-cyclo-C$_3$H$_5$, —NH—CO—NH[CH(CH$_3$)$_2$], —NH—CO—NH[C(CH$_3$)$_3$], —NH—CO—N(CH$_3$)$_2$, —NH—CO—N(C$_2$H$_5$)$_2$, —NH—CO—N(C$_3$H$_7$)$_2$, —NH—CO—N(cyclo-C$_3$H$_5$)$_2$, —NH—CO—N[CH(CH$_3$)$_2$]$_2$, —NH—CO—N[C(CH$_3$)$_3$]$_2$, —NH—CS—NH$_2$, —NH—CS—NHCH$_3$, —NH—CS—NHC$_2$H$_5$, —NH—CS—NHC$_3$H$_7$, —NH—CS—NH-cyclo-C$_3$H$_5$, —NH—CS—NH[CH(CH$_3$)$_2$], —NH—CS—NH[C(CH$_3$)$_3$], —NH—CS—N(CH$_3$)$_2$, —NH—CS—N(C$_2$H$_5$)$_2$, —NH—CS—N(C$_3$H$_7$)$_2$, —NH—CS—N(cyclo-C$_3$H$_5$)$_2$, —NH—CS—N[CH(CH$_3$)$_2$]$_2$, —NH—CS—N[C(CH$_3$)$_3$]$_2$, —NH—C(=NH)—NH$_2$, —NH—C(=NH)—NHCH$_3$, —NH—C(=NH)—NHC$_2$H$_5$, —NH—C(=NH)—NHC$_3$H$_7$, —NH—C(=NH)—NH-cyclo-C$_3$H$_5$, —NH—C(=NH)—NH[CH(CH$_3$)$_2$], —NH—C(=NH)—NH[C(CH$_3$)$_3$], —NH—C(=NH)—N(CH$_3$)$_2$, —NH—C(=NH)—N(C$_2$H$_5$)$_2$, —NH—C(=NH)—N(C$_3$H$_7$)$_2$, —NH—C(=NH)—N(cyclo-C$_3$H$_5$)$_2$, —NH—C(=NH)—N[CH(CH$_3$)$_2$]$_2$, —NH—C(=NH)—N[C(CH$_3$)$_3$]$_2$, —O—CO—NH$_2$, —O—CO—NHCH$_3$, —O—CO—NHC$_2$H$_5$, —O—CO—NHC$_3$H$_7$, —O—CO—NH-cyclo-C$_3$H$_5$, —O—CO—NH[CH(CH$_3$)$_2$], —O—CO—NH[C(CH$_3$)$_3$], —O—CO—N(CH$_3$)$_2$, —O—CO—N(C$_2$H$_5$)$_2$, —O—CO—N(C$_3$H$_7$)$_2$, —O—CO—N(cyclo-C$_3$H$_5$)$_2$, —O—CO—N[CH(CH$_3$)$_2$]$_2$, —O—CO—N[C(CH$_3$)$_3$]$_2$, —O—CO—OCH$_3$, —O—CO—OC$_2$H$_5$, —O—CO—OC$_3$H$_7$, —O—CO—O-cyclo-C$_3$H$_5$, —O—CO—OCH(CH$_3$)$_2$, —O—CO—OC(CH$_3$)$_3$, —CH$_2$F, —CHF$_2$, —CF$_3$, —CH$_2$Cl, —CH$_2$Br, —CH$_2$I, —CH$_2$—

$CH_2F$, $-CH_2-CHF_2$, $-CH_2-CF_3$, $-CH_2-CH_2Cl$, $-CH_2-CH_2Br$, $-CH_2-CH_2I$, cyclo-$C_3H_5$, cyclo-$C_4H_7$, cyclo-$C_5H_9$, cyclo-$C_6H_{11}$, cyclo-$C_7H_{13}$, cyclo-$C_8H_{15}$, -Ph, $-CH_2$-Ph, $-CPh_3$, $-CH_3$, $-C_2H_5$, $-C_3H_7$, $-CH(CH_3)_2$, $-C_4H_9$, $-CH_2-CH(CH_3)_2$, $-CH(CH_3)-C_2H_5$, $-C(CH_3)_3$, $-C_5H_{11}$, $-CH(CH_3)-C_3H_7$, $-CH_2-CH(CH_3)-C_2H_5$, $-CH(CH_3)-CH(CH_3)_2$, $-C(CH_3)_2-C_2H_5$, $-CH_2-C(CH_3)_3$, $-CH(C_2H_5)_2$, $-C_2H_4-CH(CH_3)_2$, $-C_6H_{13}$, $-C_7H_{15}$, $-C_8H_{17}$, $-C_3H_6-CH(CH_3)_2$, $-C_2H_4-CH(CH_3)-C_2H_5$, $-CH(CH_3)-C_4H_9$, $-CH_2-CH(CH_3)-C_3H_7$, $-CH(CH_3)-CH_2-CH(CH_3)_2$, $-CH(CH_3)-CH(CH_3)-C_2H$, $-CH_2-CH(CH_3)-CH(CH_3)_2$, $-CH_2-C(CH_3)_2-C_2H_5$, $-C(CH_3)_2-C_3H_7$, $-C(CH_3)_2-CH(CH_3)_2$, $-C_2H_4-C(CH_3)_3$, $-CH(CH_3)-C(CH_3)_3$, $-CH=CH_2$, $-CH_2-CH=CH_2$, $-C(CH_3)=CH_2$, $-CH=CH-CH_3$, $-C_2H_4-CH=CH_2$, $-CH_2-CH=CH-CH_3$, $-CH=CH-C_2H_5$, $-CH_2-C(CH_3)=CH_2$, $-CH(CH_3)-CH=CH$, $-CH=C(CH_3)_2$, $-C(CH_3)=CH-CH_3$, $-CH=CH-CH=CH_2$, $-C_3H_6-CH=CH_2$, $-C_2H_4-CH=CH-CH_3$, $-CH_2-CH=CH-C_2H_5$, $-CH=CH-C_3H_7$, $-CH_2-CH=CH-CH=CH_2$, $-CH=CH-CH=CH-CH_3$, $-CH=CH-CH_2-CH=CH_2$, $-C(CH_3)=CH-CH=CH_2$, $-CH(CH_3)-CH=CH_2$, $-CH=CH-C(CH_3)=CH_2$, $-C_2H_4-C(CH_3)=CH_2$, $-CH_2-CH(CH_3)-CH=CH_2$, $-CH(CH_3)-CH=CH_2$, $-CH(CH_3)-CH_2-CH=CH_2$, $-CH_2-CH=C(CH_3)_2$, $-CH_2-C(CH_3)=CH-CH_3$, $-CH(CH_3)-CH=CH-CH_3$, $-CH=CH-CH(CH_3)_2$, $-CH=C(CH_3)-C_2H_5$, $-C(CH_3)=CH-C_2H_5$, $-C(CH_3)=C(CH_3)_2$, $-C(CH_3)_2-CH=CH_2$, $-CH(CH_3)-C(CH_3)=CH_2$, $-C(CH_3)=CH-CH_2-CH_3$, $-CH=C(CH_3)-CH=CH_2$, $-CH=CH-C(CH_3)=CH_2$, $-C_4H_8-CH=CH_2$, $-C_3H_6-CH=CH-CH_3$, $-C_2H_4-CH=CH-C_2H_5$, $-CH_2-CH=CH-C_3H_7$, $-CH=CH-C_4H_9$, $-C_3H_6-C(CH_3)=CH_2$, $-C_2H_4-CH(CH_3)-CH=CH_2$, $-CH_2-CH(CH_3)-CH_2-CH=CH_2$, $-CH(CH_3)-C_2H_4-CH=CH_2$, $-C_2H_4-CH=C(CH_3)_2$, $-C_2H_4-C(CH_3)=CH-CH_3$, $-CH_2-CH(CH_3)-CH=CH-CH_3$, $-CH(CH_3)-CH_2-CH=CH-CH_3$, $-CH_2-CH=CH-CH(CH_3)_2$, $-CH_2-CH=C(CH_3)-C_2H_5$, $-CH_2-C(CH_3)=CH-C_2H_5$, $-CH(CH_3)-CH=CH-C_2H_5$, $-CH=CH-CH_2-CH(CH_3)_2$, $-CH=CH-CH(CH_3)-C_2H_5$, $-CH=C(CH_3)-C_3H_7$, $-C(CH_3)=CH-C_3H_7$, $-CH_2-CH(CH_3)-C(CH_3)=CH_2$, $-CH(CH_3)-CH_2-C(CH_3)=CH_2$, $-CH(CH_3)-CH(CH_3)-CH=CH_2$, $-CH(CH_3)-C(CH_3)=CH-CH_3$, $-CH_2-C(CH_3)_2-CH=CH_2$, $-C(CH_3)_2-CH_2-CH=CH_2$, $-C(CH_3)_2-CH=CH-CH_3$, $-CH=CH-C(CH_3)_3$, $-CH(CH_3)-CH=C(CH_3)_2$, $-C(CH_3)_2-C(CH_3)=CH_2$, $-C(CH_3)_2-CH=CH-CH_3$, $-CH=CH-C(CH_3)_2-CH_3$, $-CH=C(CH_3)-CH(CH_3)_2$, $-C(CH_3)=C(CH_3)-C_2H_5$, $-CH=CH-C(CH_3)_3$, $-C(CH_3)_2-C(CH_3)=CH_2$, $-C(CH_3)(C_2H_5)-CH=CH_2$, $-CH(CH_3)-C(C_2H_5)=CH_2$, $-CH_2-C(C_3H_7)=CH_2$, $-CH_2-C(C_2H_5)=CH-CH_3$, $-CH(C_2H_5)-CH=CH-CH_3$, $-C(C_4H_9)=CH_2$, $-C(C_3H_7)=CH-CH_3$, $-C(C_2H_5)=CH-C_2H_5$, $-C(C_2H_5)=C(CH_3)_2$, $-C[C(CH_3)_3]=CH_2$, $-C[CH(CH_3)(C_2H_5)]=CH_2$, $-C[CH_2-CH(CH_3)_2]=CH_2$, $-C_2H_4-CH=CH-CH=CH_2$, $-CH=CH-CH=C(CH_3)_2$, $-CH_2-CH=CH-CH_2-CH=CH_2$, $-CH=CH-CH_2-CH=CH-CH_3$, $-CH=CH-CH_2-CH_3$, $-CH=CH-CH(CH_3)-C_2H_5$, $-CH_2-CH=C(CH_3)_2$, $-CH_2-CH=CH-C(CH_3)=CH_2$, $-CH=CH-CH_2-C(CH_3)=CH_2$, $-CH=CH-CH(CH_3)-CH=CH_2$, $-CH=C(CH_3)-CH_2-CH=CH_2$, $-CH=C(CH_3)-CH_2-CH=CH_2$, $-C(CH_3)=CH-CH_2-CH=CH_2$, $-CH=CH-C(CH_3)=CH-CH_3$, $-CH=C(CH_3)-CH=CH-CH_3$, $-C(CH_3)=CH-CH=CH-CH_3$, $-CH=C(CH_3)-CH=CH-CH_3$, $-CH=CH-CH=C(CH_3)-C(CH_3)=CH_2$, $-C(CH_3)=CH-C(CH_3)=CH_2$, $-C(CH_3)=C(CH_3)-CH=CH_2$, $-CH=CH-CH=CH-CH=CH_2$, $-C\equiv CH$, $-C\equiv C-CH_3$, $-CH_2-C\equiv CH$, $-C_2H_4-C\equiv CH$, $-CH_2-C\equiv C-CH_3$, $-C\equiv C-C_2H_5$, $-C_3H_6-C\equiv CH$, $-C_2H_4-C\equiv C-CH_3$, $-CH_2-C\equiv C-C_2H_5$, $-C\equiv C-C_3H_7$, $-CH(CH_3)-C\equiv CH$, $-CH_2-CH(CH_3)-C\equiv CH$, $-CH(CH_3)-CH_2-C\equiv CH$, $-CH(CH_3)-C\equiv C-CH_3$, $-C_4H_8-C\equiv CH$, $-C_3H_6-C\equiv C-CH_3$, $-C_2H_4-C\equiv C-C_2H_5$, $-CH_2-C\equiv C-C_3H_7$, $-C\equiv C-C_4H_9$, $-C_2H_4-CH(CH_3)-C\equiv CH$, $-CH_2-CH(CH_3)-CH_2-C\equiv CH$, $-CH(CH_3)-C_2H_4-C\equiv CH$, $-CH_2-CH(CH_3)-C\equiv C-CH_3$, $-CH(CH_3)-CH_2-C\equiv C-CH_3$, $-CH(CH_3)-C\equiv C-C_2H_5$, $-CH_2-C\equiv C-CH(CH_3)_2$, $-C\equiv C-CH(CH_3)-C_2H_5$, $-C\equiv C-CH_2-CH(CH_3)_2$, $-C\equiv C-C(CH_3)_3$, $-CH(C_2H_5)-C\equiv C-CH_3$, $-C(CH_3)_2-C\equiv C-CH_3$, $-CH(C_2H_5)-CH_2-C\equiv CH$, $-CH_2-CH(C_2H_5)-C\equiv CH$, $-C(CH_3)_2-CH_2-C\equiv CH$, $-CH_2-C(CH_3)_2-C\equiv CH$, $-CH(CH_3)-CH(CH_3)-C\equiv CH$, $-CH(C_3H_7)-C\equiv CH$, $-C(CH_3)(C_2H_5)-C\equiv CH$, $-C\equiv C-C\equiv CH$, $-CH_2-C\equiv C-C\equiv CH$, $-C\equiv C-C\equiv C-CH_3$, $-CH(C\equiv CH)_2$, $-C_2H_4-C\equiv C-C\equiv CH$, $-CH_2-C\equiv C-CH_2-C\equiv CH$, $-C\equiv C-C_2H_4-C\equiv CH$, $-CH_2-C\equiv C-C\equiv C-CH_3$, $-C\equiv C-CH_2-C\equiv C-CH_3$, $-C\equiv C-C\equiv C-C_2H_5$, $-C\equiv C-CH(CH_3)-C\equiv CH$, $-CH(CH_3)-C\equiv C-C\equiv CH$, $-CH(C\equiv CH)-CH_2-C\equiv CH$, $-C(C\equiv CH)_2-CH_3$, $-CH_2-CH(C\equiv CH)_2$, $-CH(C\equiv CH)-C\equiv C-CH_3$;

wherein each pair of adjacent substituents $R^3$ and $R^4$ or $R^4$ and $R^5$ or $R^5$ and $R^6$ or $R^6$ and $R^7$ may be connected via a $-CH=CH-CH=CH-$ or an analogous heteroatom-carrying group to form a condensed aromatic or heteroaromatic ring; as well as metal complexes thereof, salts, enantiomers, enantiomeric mixtures, diastereomers, diastereomeric mixtures, tautomers, hydrates, solvates and racemates or also dimers or oligomers of the aforementioned compounds linked in any way.

Excluded from the present invention is the compound named 16β-(2-hydroxy-3,5-di-tert-butylphenyl-methylamino)-17α-hydroxy-3-methoxy-estra-1,3,5(10)-triene (Ref. 1). If residues $R^6$ and $R^7$ are bound to a naphthyl ring, these preferably form no further aromatic or heteroaromatic ring.

Within the meaning of the general formula (I), each pair of adjacent substituents of groups R3 to R7 may also be connected via $-CH=CH-CH=CH-$ or analogous heteroatom-carrying unsaturated residues or also represent different condensed aromatic and heterocyclic ring systems.

As linker or spacer L, alkyl spacers, alkenyl spacers, polyethylene glycol spacers and generally polyalkylene-oxy spacers are particularly preferred. Spacers can furthermore be synthesized using the following reagents: 4-acetoxymethyl benzoic acid, 3-(9-fluorenyl methyloxycarbonyl)amino-3-(2-nitrophenyl)propionic acid, 4-(4-formyl-3,5-dimetoxyphenoxy) butyric acid, 5-(4-formyl-3,5-dimethoxyphenoxy)pentanoic acid, 4-bromomethylphenylacetic acid, 2-(1-t-butyloxycarbonyl-4-methyl-imidazole-5-yl)-2-hydroxy-acetic acid dicyclohexylamine, 2-hydroxy-10,11-dihydro-5H-dibenzo[a,d]cycloheptene-5-one, 5-[4-(9-fluorenyl methoxycarbonyl)aminomethyl-3,5-dimethoxyphenoxy]-pentanoic acid, 4-{4-[1-(9-fluorenyl methyloxycarbonylamino)ethyl]-2-methoxy-5-nitrophenoxy}-butyric acid, 4'-{(R,S)-α-[1-(9-fluorenyl)methoxycarbonylamino]-2,4- dimethoxybenzyl}-phenoxy acetic acid, 4-(4'-formyl-3'-methoxyphenoxy)-butyric acid, 4-hydroxymethyl-benzoic acid, 4-hydroxymethyl-phenoxy acetic acid, 3-(4-hydroxymethylphenoxy)propionic acid, 4-(4-hydroxymethyl-3-methoxyphenoxy)-butyric acid, 5-(4-hydroxymethylphenoxy)pentanoic acid, 4-hydroxymethylphenyl-acetic acid, 5-[4-aminomethyl-3,5-dimethoxyphenoxy]-pentanoic acid, p-hydroxy-tetrafluorobenzoic acid hydrate, 2-(3-formyl-1H-indol-1-yl)-acetic acid, (R,S)-2-{[5-(9-fluorenyl methyloxycarbonylamino)-dibenzo[a,d]cyclo-heptane-2-yl]oxy}-acetic acid.

It is equally possible that more than one arylmethylamino fragment

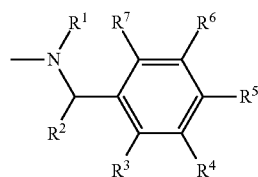

is bound to a steroid group $R^{\#}$.

The steroid group $R^{\#}$ may thus carry two, three or four arylmethylamino fragments which is to be represented by the following formula (VI):

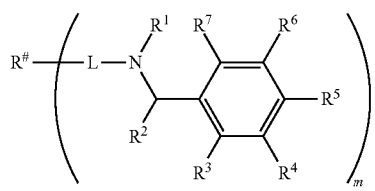

wherein
m is 1, 2, 3 or 4, and residues $R^1$ to $R^7$ and $R^{\#}$ have the abovementioned meaning.

Possible are also compounds of the general formula (II) without spacer, i.e. compounds wherein L represents a chemical bond:

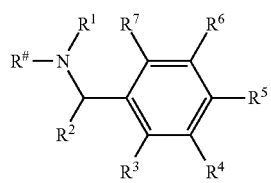

and wherein residues $R^1$ to $R^7$ and $R^{\#}$ have the abovementioned meaning.

Preferred are furthermore compounds of the general formula (III):

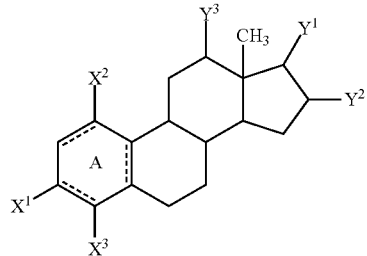

wherein
$Y^1, Y^2, Y^3$ independently of one another represent

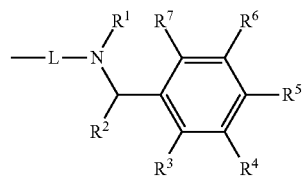

—H, —OH,
$X^1$, $X^2$, $X^3$ independently of one another represent —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —CH$_3$, —C$_2$H$_5$, —C$_3$H$_7$, —CH(CH$_3$)$_2$, —C$_4$H$_9$;
ring A may be saturated or aromatic, wherein dashed lines in ring A indicate the possible presence of three double bonds; and
residues $R^1$ to $R^7$ and spacer L have the abovementioned meaning.

Preferred is furthermore for compounds of the present invention if one of the residues $R^3$, $R^5$ or $R^7$ is a hydroxy group. Advantageous is moreover if compounds of this invention carry no —C(CH$_3$)$_3$ group at positions $R^3$-$R^7$.

Residues $X^1$ and $X^2$ are, independently of one another, preferably selected from —OH or —OCH$_3$ and residue $X^3$ is preferably —H, —CH$_3$ or —C$_2$H$_5$.

Advantageous are furthermore the general formulas (IV) and (V):

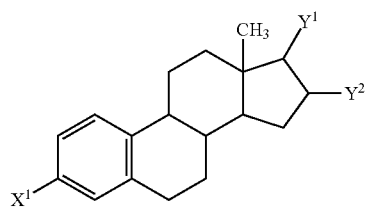

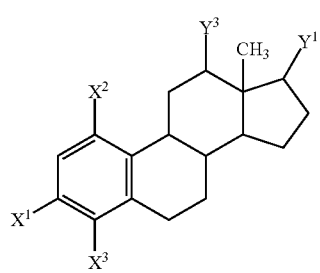

wherein residues $X^1$ to $X^3$ and residues $Y^1$ to $Y^3$ have the abovementioned meaning.

Compounds of the formula (I), (II), (III), (IV) and (V) according to the present invention may be administered per se or in the form of a pharmacologically active salt thereof. Since compounds of the general formula (I) can have alkaline as well as acidic properties, salts of said compounds can be synthesized according to commonly used procedures.

Suitable examples for salts of compounds of the formula (I), (II), (III), (IV) and (V) include acid addition salts, alkali metal salts as well as salts with amines. Among these alkali metal salts like sodium salt, potassium salt, lithium salt or magnesium salt, calcium salt, alkyl ammonium salt or amino acid salts, e.g. with basic amino acids like lysine can be named. Examples for acids which form acid addition salts with compounds of the formula (I), (II), (III), (IV) and (V) are the following: sulphuric acid, sulfonic acid, phosphoric acid, nitric acid, nitrous acid, perchloric acid, hydrobromic acid, hydrochloric acid, formic acid, acetic acid, propionic acid, succinic acid, oxalic acid, gluconic acid (glyconic acid, dextronic acid), lactic acid, malic acid, tartaric acid, tartronic acid (hydroxymalonic acid, hydroxypropanedioic acid), fumaric acid, citric acid, ascorbinic acid, maleic acid, malonic acid, hydroxymaleic acid, pyruvic acid, phenylacetic acid, (o-, m-, p-) toluic acid, benzoic acid, p-aminobenzoic acid, p-hydroxybenzoic acid, salicylic acid, p-aminosalicylic acid, methanesulfonic acid, ethanesulfonic acid, hydroxyethanesulfonic acid, ethylenesulfonic acid, p-toluenesulfonic acid, naphthylsulfonic acid, naphthylaminesulfonic acid, sulfanilic acid, camphorsulfonic acid, quinic acid (quinine acid), o-methyl-mandelic acid, hydrogen benzenesulfonic acid, picric acid (2,4,6-trinitro-phenole), adipic acid, d-o-tolyl tartaric acid, amino acids like methionine, tryptophan, arginine and in particular acidic amino acids like glutamic acid or asparaginic acid.

Core structure of all steroids is gonane, representing a cyclopentanoperhydrophenanthrene ring system (exception: vitamin D). Gonane consists of seventeen carbon atoms forming four ring systems: three cyclohexane rings (denoted as rings A, B and C in the figure of a steroid core structure shown below) and a cyclopentane ring (D-ring). Preferred are compounds of the general formula (I), wherein the steroid group is substituted at the D-ring.

Steroids differ with respect to the functional groups attached to the rings and with respect to the oxidation state of the rings. In plants, animals and fungi, a large variety of different steroids are synthesized. All steroids are produced in cells either from lanosterol (animals and fungi) or from cycloartenol (plants). Steroids have a rigid molecular structure, a generally relatively high melting point and are easily crystallizable. Due to the asymmetric C-atoms at the ring junctions, several structural isomers are possible. According to general conventions, the position of the methyl group at carbon atom 10 which is in naturally occurring steroids in most cases above the steroid plane (β-face) serves as reference point for the systematic nomenclature of the spatial configuration of substituents at the gonane core structure, which in saturated ring systems can be oriented either in axial or equatorial position: substituents directed towards the β-face (mostly equatorial) are indicated with the index "β", while substituents directed more towards the steroid underface are indicated with the index "α".

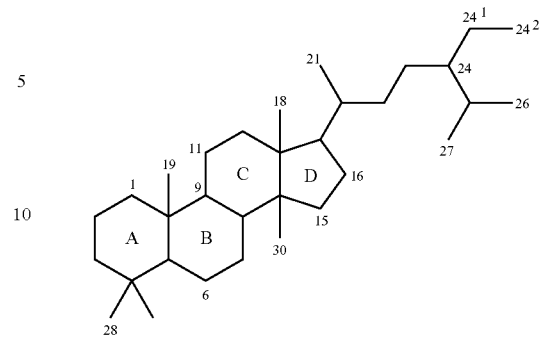

The following two formulae describe a form of the gonane core structure:

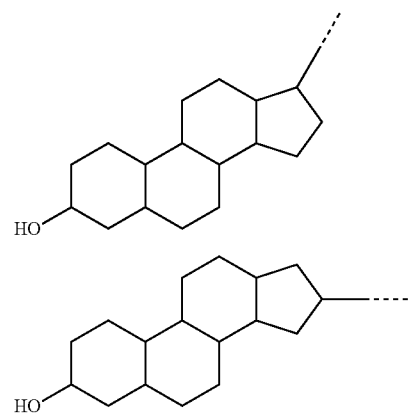

Gonane is the systematic name of the hydrocarbon core structure of steroids (perhydrocyclopenta[a]phenanthrene) lacking angular methyl groups at C-10 and C-13. Sterols (or also sterins) are steroid alcohols having a β-positioned hydroxy group at C-3 and one or more double bonds in ring B, while further oxygen-functions like for example carbonyl and carboxyl groups are missing.

The most important sterol in animals is cholesterol. Plants and microorganisms possess a larger variety of closely related sterols, e.g. ergosterol or stigmasterol. In the liver, bile acids (e.g. cholic acids) are synthesized from cholesterol. Characteristic is a side chain shortened by three C-atoms, of which the last C-atom is oxidized to a carboxyl group. The double bond in ring B is reduced, and the steroid core carries one to three α-positioned hydroxy groups. Steroid hormones of mammals are also synthesized from cholesterol.

Humans possess six steroid hormones: progesterone, cortisol, aldosterone, testosterone, estradiol and calcitriol. These steroids carry, with the exception of calcitriol, either no side chain or only a short (max. 2 C atoms) side chain. Characteristic feature is an oxo-group at C-3 and the corresponding conjugated double bond at C-4/C-5 in ring A. Differences occur in rings A, B, C and D. Estradiol is aromatic in ring A. Calcitriol differs from the other mammalian steroid hormones, it still contains the entire carbon core of the cholesterol, but is modified to a secosteroid (a steroid with open ring) by opening of ring B.

According to the present invention, furthermore preferred are the following steroid residues:
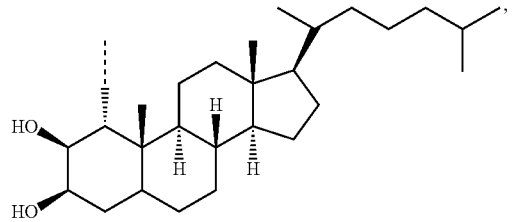
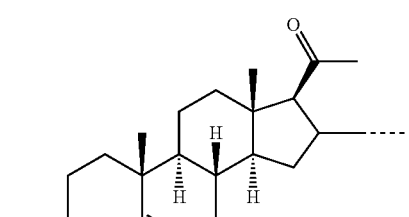
Pregnenolone residue
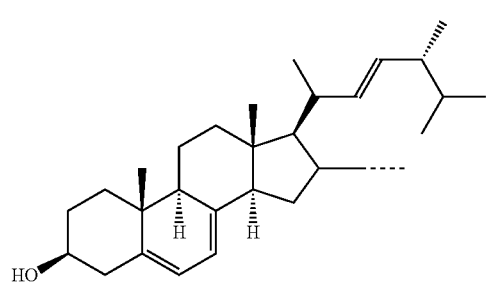
Ergosterol residue
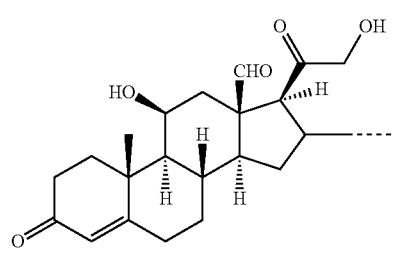
Aldosterone residue
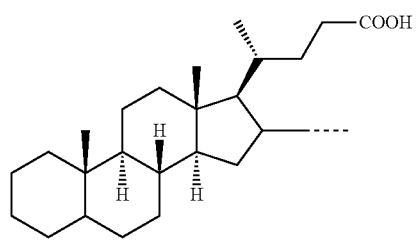
Cholanic acid residue
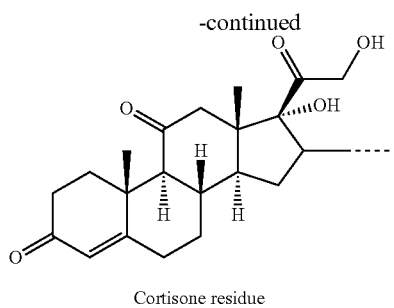
Cortisone residue
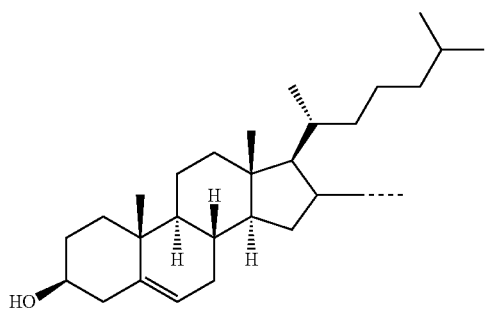
Cholesterol residue
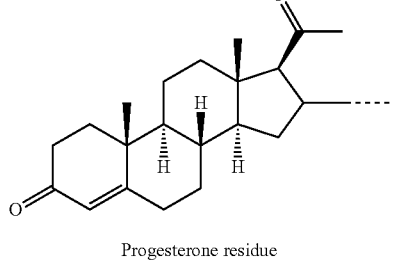
Progesterone residue
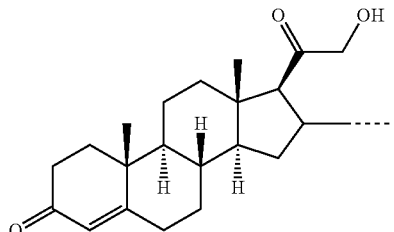
Deoxycorticosterone residue
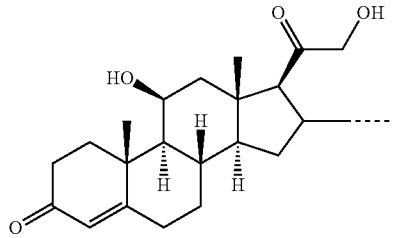
Corticosterone residue
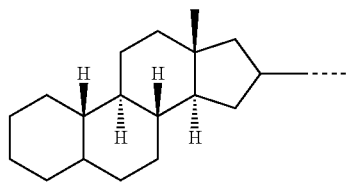
Estrane residue

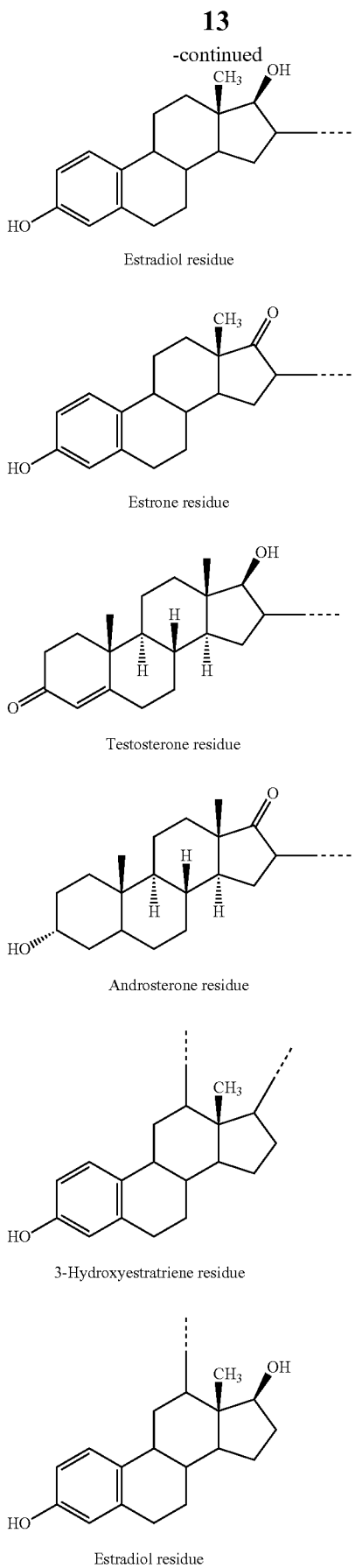
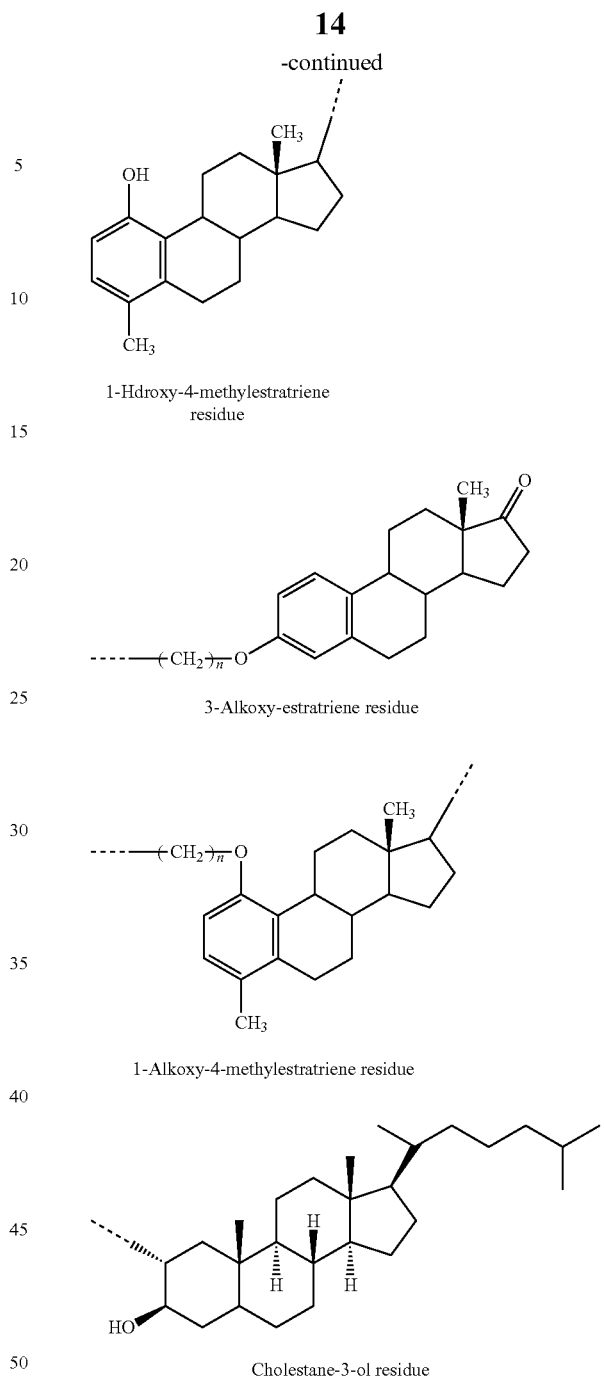

Preferred are compounds of the general formula (I), wherein R# represents a sterol residue, estrone methylether residue, estrone residue, testosterone residue, androsterone residue, estradiol residue, estrane residue, corticosterone residue, deoxycorticosterone residue, progesterone residue, pregnenolone residue, aldosterone residue, cortisone residue, cholanic acid residue, ergosterol residue or cholesterol residue. Furthermore preferred are residues derived from steroid hormones, and particularly preferred are estradiol residues—also referred to as estrogen residues—and steroid residues derived thereof. Particularly preferred are compounds of the general formula (I) in which steroid residue R# represents an estrone methylether residue of one of the following formulas:

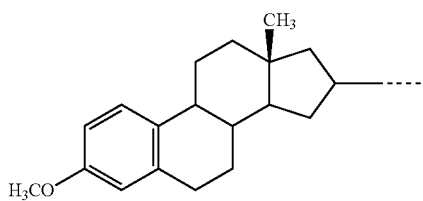
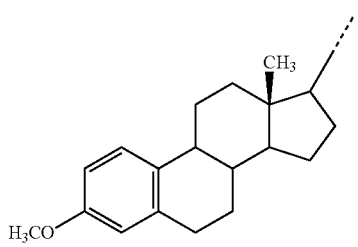
In addition preferred are the following substructures:
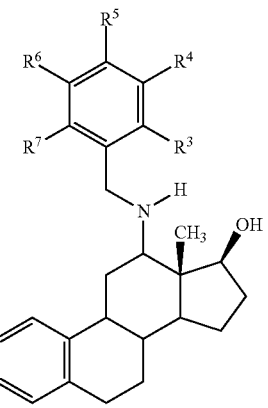
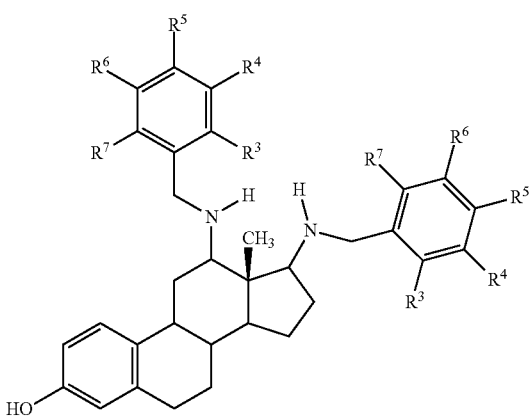
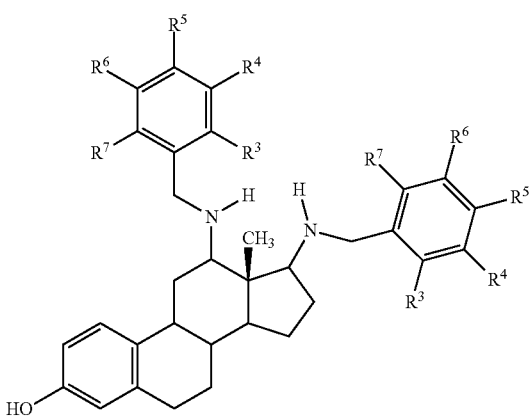
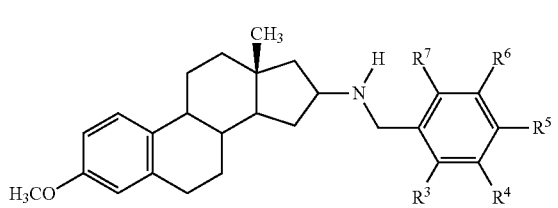
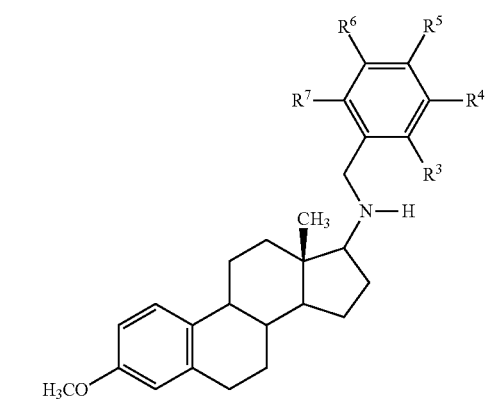
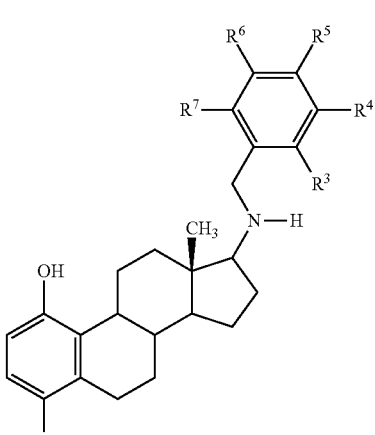
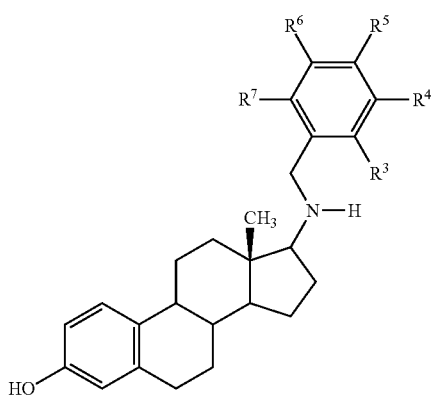
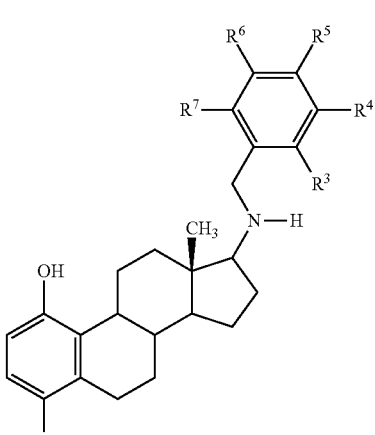
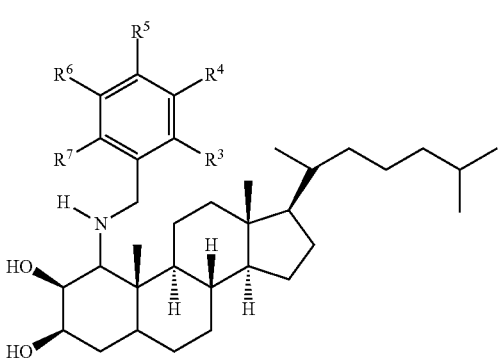

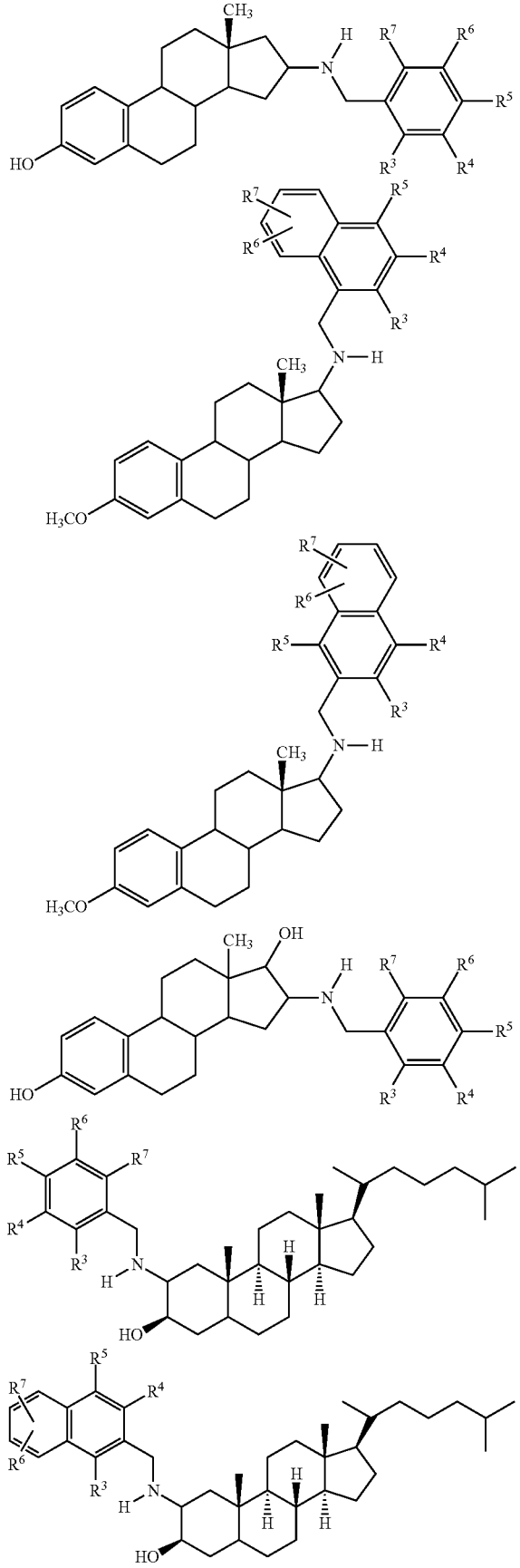
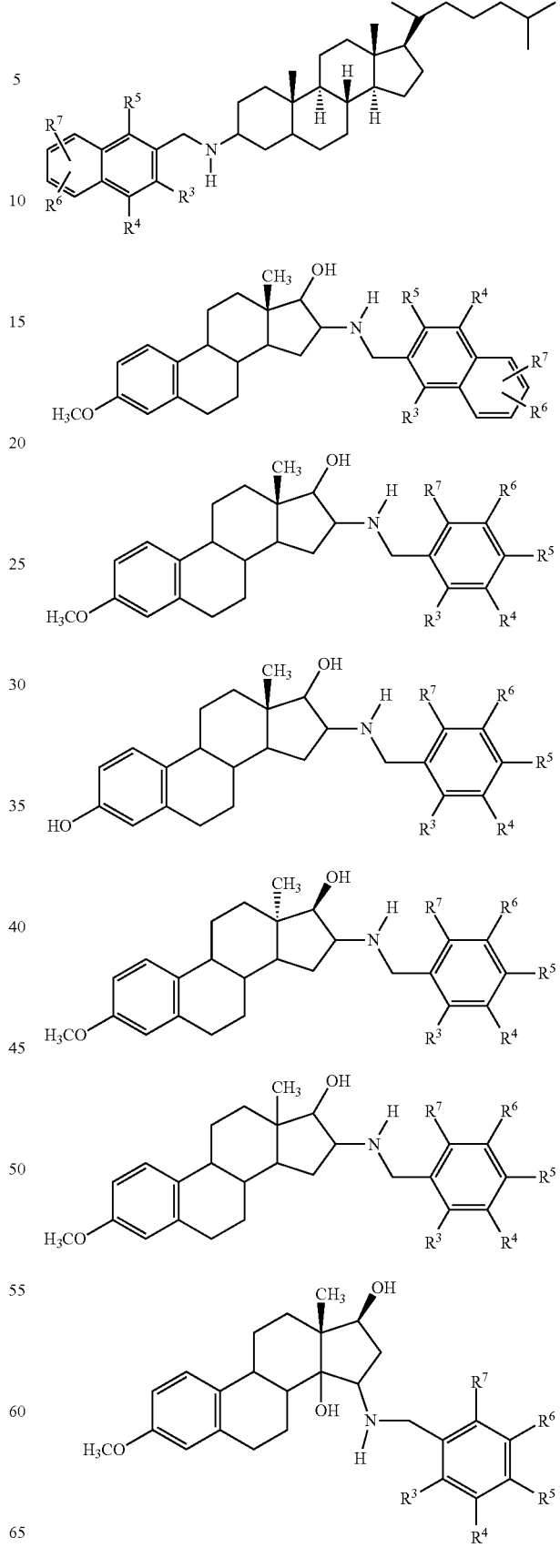

In the case that $R^1$ and $R^2$ together represent a bond, the following preferred substructures result:

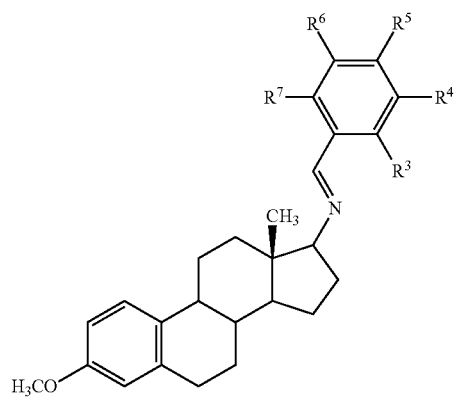

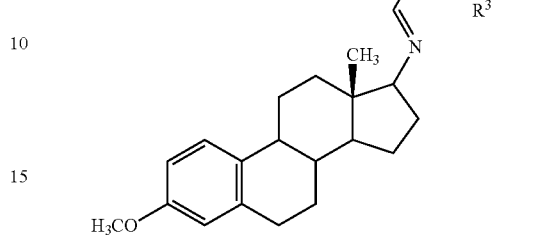

Furthermore preferred are compounds of the general formula (I) wherein $R^3$ represents —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$ or —N[C(CH$_3$)$_3$]$_2$.

The following compounds of the general formula (I) are particularly preferred:

| | Formula | Nomenclature |
|---|---|---|
| 1 | | 17β-(2-Hydroxyphenyl-methylamino)-3-methoxy-estra-1,3,5(10)-triene |
| 2 | | 17α-(2-Hydroxyphenyl-methylamino)-3-methoxy-estra-1,3,5(10)-triene |

-continued

| | Formula | Nomenclature |
|---|---|---|
| 3 | | 16β-(2-Hydroxyphenyl-methylamino)-3-methoxy-estra-1,3,5(10)-triene |
| 4 | | 16α-(2-Hydroxyphenyl-methylamino)-3-methoxy-estra-1,3,5(10)-triene |
| 5 | | 17α-(2-Methoxyphenyl-methylamino)-3-methoxy-estra-1,3,5(10)-triene |
| 6 | | 17α-(3-Hydroxyphenyl-methylamino)-3-methoxy-estra-1,3,5(10)-triene |
| 7 | | 17α-(4-Hydroxyphenyl-methylamino)-3-methoxy-estra-1,3,5(10)-triene |

-continued

| | Formula | Nomenclature |
|---|---|---|
| 8 | | 13α-3-Hydroxy-17α-(3-hydroxyphenyl-methylamino)-estra-1,3,5(10)-triene |
| 9 | | 13α-3-Hydroxy-17β-(3-hydroxyphenyl-methylamino)-estra-1,3,5(10)-triene |
| 10 | | 1-Hydroxy-17α-(2-hydroxyphenyl-methylamino)-4-methyl-estra-1,3,5(10)-triene |
| 11 | | 3, 17β-Dihydroxy-12α-(2-hydroxyphenylmethyl-amino)estra-1,3,5(10)-triene |
| 12 | | 3, 17β-Dihydroxy-12β-(2-hydroxyphenyl-methylamino)estra-1,3,5(10)-triene |

-continued

| | Formula | Nomenclature |
|---|---|---|
| 13 | | 3-Hydroxy-12α, 17α-bis(2-hydroxyphenyl-methylamino)-estra-1,3,5(10)-triene |
| 14 | | 3-Hydroxy-12β-bis(2-hydroxyphenyl-methylamino)-estra-1,3,5(10)-triene |
| 15 | | 3-Hydroxy-12α, 17β-bis(2-hydroxyphenyl-methylamino)-estra-1,3,5(10)-triene |
| 16 | | 3-Hydroxy-12β, 17α-bis(2-hydroxyphenyl-methylamino)-estra-1,3,5(10)-triene |
| 17 | | 17α-[(2-Hydroxynaphth-1-yl)-methylamino]-3-methoxy-estra-1,3,5(10)-triene |

-continued

| | Formula | Nomenclature |
|---|---|---|
| 18 | | 17β-[(3-Hydroxynaphth-2-yl)-methylamino]-3-methoxy-estra-1,3,5(10)-triene |
| 19 | | 17β-[(2-Hydroxynaphth-1-yl)-methylamino]-3-methoxy-estra-1,3,5(10)-triene hydroperchlorate |
| 20 | | 17β-(3-Hydroxyphenyl-methylamino)-3-methoxy-estra-1,3,5(10)-triene |
| 21 | | 3β-Hydroxy-2α-(2-hydroxyphenyl-methyl amino)-cholane |
| 22 | | 2β,3β-Dihydroxy-1α-(2-hydroxyphenyl-methyl amino)-cholane |

| | Formula | Nomenclature |
|---|---|---|
| 23 | | 17β-[4-(N,N-Diethylamino)-2-hydroxyphenyl-methyl amino]-3-methoxy-estra-1,3,5(10)-triene |
| 24 | | 17β-(4-N,N-Diethylamino-2-hydroxyphenyl-carbaldimino)-3-methoxy-estra-1,3,5(10)-triene |
| 25 | | 17β-(3-Hydroxy-naphth-2-carbaldimino)-3-methoxy-estra-1,3,5(10)-triene |
| 26 | | 17(5-Chloro-2-hydroxyphenyl-methylamino)-3-methoxy-estra-1,3,5(10)-triene |

-continued

| | Formula | Nomenclature |
|---|---|---|
| 27 | 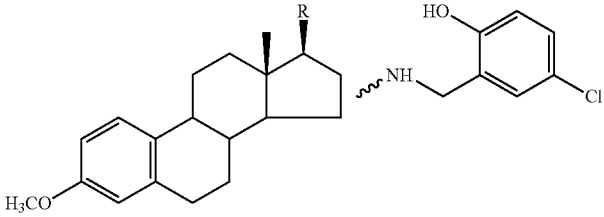 | 17β-(5-Chloro-2-hydroxyphenyl-methylamino)-3-methoxy-estra-1,3,5(10)-triene |
| 28 | 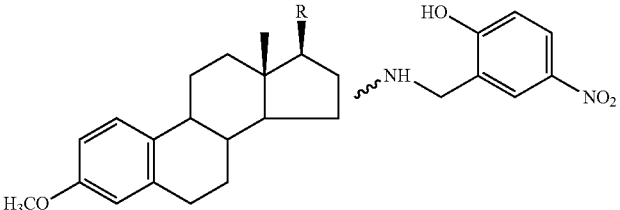 | 17β-(2-Hydroxy-5-nitrophenyl-methylamino)-3-methoxy-estra-1,3,5(10)-triene |
| 29 | 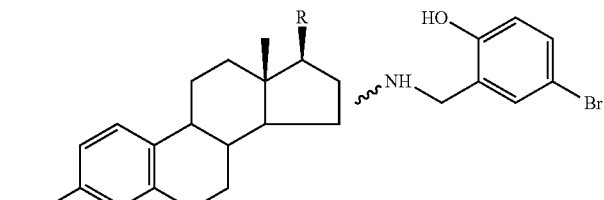 | 17β-(5-Bromo-2-hydroxyphenyl-methylamino)-3-methoxy-estra-1,3,5(10)-triene |
| 30 | 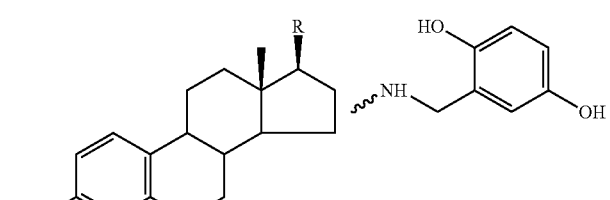 | 17β-(2,5-Dihydroxyphenyl-methylamino)-3-methoxy-estra-1,3,5(10)-triene |
| 31 | 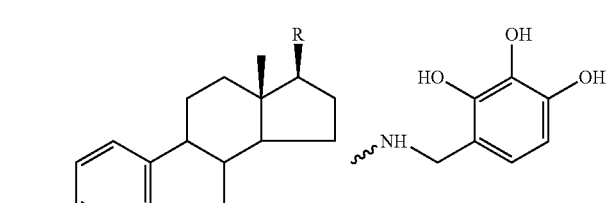 | 17β-(2,3,4-Trihydroxyphenyl-methylamino)-3-methoxy-estra-1,3,5(10)-triene |
| 32 | 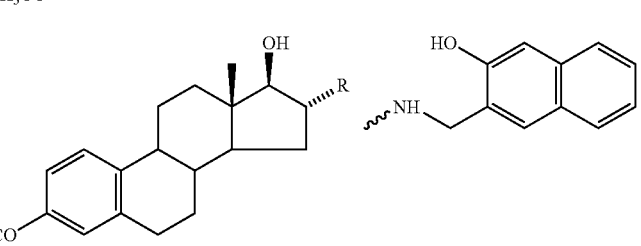 | 16α-[(3-Hydroxy-naphth-2-yl)-methylamino]-17β-hydroxy-3-methoxy-estra-1,3,5(10)-triene |
| 33 | 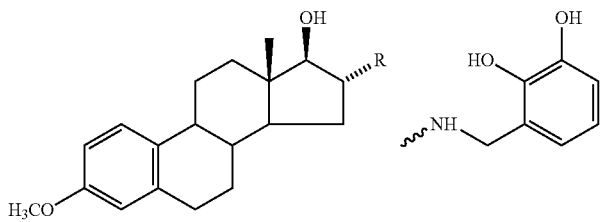 | 16α-(2,3-Dihydroxyphenyl-methylamino)-17β-hydroxy-3-methoxy-estra-1,3,5(10)-triene |

-continued

| | Formula | Nomenclature |
|---|---|---|
| 34 | 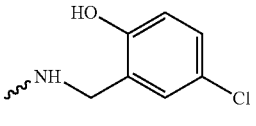 | 16α-(5-Chloro-2-hydroxyphenyl-methylamino)-17β-hydroxy-3-methoxy-estra-1,3,5(10)-triene |
| 35 | 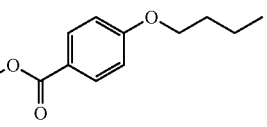 | 16β-{[2-Hydroxy-4-(4'-(4''-n-butoxy-phenyl)carbonyloxy)-phenyl]-methylamino}-17α-hydroxy-3-methoxy-estra-1,3,5(10)-triene |
| 36 | 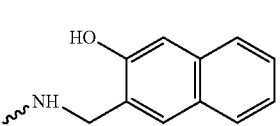 | 16α-[(3-Hydroxy-naphth-2-yl)-methylamino]-17α-hydroxy-3-methoxy-estra-1,3,5(10)-triene |
| 37 | 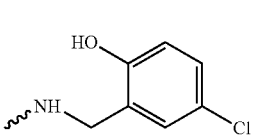 | 16α-(5-Chloro-2-hydroxyphenyl-methylamino)-17α-hydroxy-3-methoxy-estra-1,3,5(10)-triene |
| 38 | 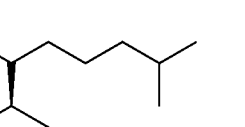 | 2α-(2-Hydroxyphenyl-methylamino)-3α-hydroxy-cholane |
| 39 | 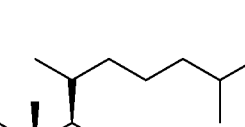 | 2α-[(3-Hydroxy-naphth-2-yl)-methylamino]-3β-hydroxy-cholane |

-continued

| | Formula | Nomenclature |
|---|---|---|
| 40 | | 3α-[(3-Hydroxy-naphth-2-yl)-methylamino]-cholane |
| 41 | | 17α-[(3-Hydroxy-naphth-2-yl)-methylamino]-3-methoxy-estra-1,3,5(10)-triene |
| 42 | | 16β-(2-Hydroxyphenyl-methylamino)-17β-hydroxy-3-methoxy-estra-1,3,5(10)-triene |
| 43 | | 16α-(2-Hydroxyphenyl-methylamino)-17β-hydroxy-3-methoxy-estra-1,3,5(10)-triene |
| 44 | | 16β-(2-Hydroxyphenyl-methylamino)-17α-hydroxy-3-methoxy-estra-1,3,5(10)-triene |
| 45 | | 16α-(2-Hydroxyphenyl-methylamino)-17α-hydroxy-3-methoxy-estra-1,3,5(10)-triene |

-continued

| | Formula | Nomenclature |
|---|---|---|
| 46 | | 3,17β-Dihydroxy-16α-(2-hydroxyphenyl-methylamino)-estra-1,3,5(10)-triene |
| 47 | | 16β-(2-Hydroxyphenyl-methylamino)-17β-hydroxy-3-methoxy-13α-estra-1,3,5(10)-triene |
| 48 | | 16α-(2-Hydroxyphenyl-methylamino)-17β-hydroxy-3-methoxy-13α-estra-1,3,5(10)-triene |
| 49 | | 17α-(4-Methoxyphenyl-methylamino)-3-methoxy-estra-1,3,5(10)-triene |
| 50 | | 14β,17β-Diydroxy-15α-(2-hydroxyphenyl-methylamino)-estra-1,3,5(10)-triene |
| 51 | | 14α,17β-Diydroxy-15β-(2-hydroxyphenyl-methylamino)-estra-1,3,5(10)-triene |

-continued

| | Formula | Nomenclature |
|---|---|---|
| 52 | | 16β-{[2-Hydroxy-4-(4'-(4''-n-butoxy-phenyl)carbonyloxy)-phenyl]-methylamino}-17β-hydroxy-3-methoxy-estra-1,3,5(10)-triene |
| 53 | | 16α-{[2-Hydroxy-4-(4'-phenylcarbonyloxy)-phenyl]-methylamino}-17β-hydroxy-3-methoxy-estra-1,3,5(10)-triene |
| 54 | | 16α-{1-[2-Hydroxy-4-(4'-phenylcarbonyloxy)-phenyl]-eth-1-ylamino}-17β-hydroxy-3-methoxy-estra-1,3,5(10)-triene |
| 55 | | 16α-{[2-Hydroxy-4-(4'-(4''-n-butoxy-phenyl)carbonyloxy)-phenyl]-methylamino}-17β-hydroxy-3-methoxy-estra-1,3,5(10)-triene |
| Ref 1 | | 16β-(2-Hydroxy-3,5-di-tert-butylphenyl-methylamino)-17α-hydroxy-3-methoxy-estra-1,3,5(10)-triene |

The present invention furthermore comprises compounds of the general formula (I) for a use in medicine, particularly preferred for the treatment and/or prophylaxis of parasitic, bacterial, mycotic and/or viral infections and diseases.

Surprisingly it could be demonstrated that compounds of the general formula (I) exhibit an inhibitory effect on the reproduction of chloroquine-resistant P. falciparum strains. This effect was demonstrated both in vitro as well as in vivo in the mouse model.

The hormonal activity of the steroid derivatives is reduced as far as possible, due to the basic nitrogen group introduced and generally also due to the substituent pattern differing from steroid hormones, which is in hormones responsible for their specific interaction and binding. Side-effects are thus reduced. The inventors were in addition able to show that the cytotoxicity of compounds of the present invention is very low.

The present invention moreover relates to pharmaceutical compositions which were manufactured using at least one of the compounds according to this invention or a salt thereof.

In addition to at least one compound of the general formula (I), said pharmaceutical compositions contain a pharmacologically acceptable carrier, excipient and/or solvent.

Said pharmaceutical compositions may be prepared and administered in the form of drops, mouth sprays, nasal sprays, pills, tablets, film tablets, layer tablets, uvulas, gels, ointments, syrups, inhalation powders, granulates, suppositories, emulsions, dispersions, microcapsules, capsules or injection solutions. Pharmaceutical compositions of this invention in addition comprise formulations like layer tablets for controlled and/or continuous release of the active substance as well as micro-encapsulations as specific dosage form.

Such formulations are among others suitable for inhalation or intravenous, intraperitoneal, intramuscular, subcutaneous, mucocutaneous, oral, rectal, transdermal, topical, buccal, intradermal, intragastral, intracutaneous, intranasal, intrabuccal, percutaneous or sublingual administration.

As pharmaceutically acceptable carrier, for example lactose, starch, sorbitol, sucrose, cellulose, magnesium stearate, dicalcium phosphate, calcium sulfate, talcum, mannitol, ethyl alcohol and the like can be used. Powders as well as tablets may consist of approximately 5 to 95 percent of such a carrier.

Disintegrants, coloring agents, flavorings and/or binding agents may furthermore be added to said pharmaceutical compositions.

Liquid formulations comprise solutions, suspensions, sprays and emulsions, for example water-based or water-propylene glycol based injection solutions for parenteral injections.

For the preparation of suppositories, preferably low melting waxes, fatty acid ester and glycerides are used.

Capsules are for example manufactured from methylcellulose, polyvinyl alcohol or denatured gelatine or starch.

As disintegrating agents, starch, sodium carboxymethyl cellulose, natural and synthetic gums like for example locust bean gum flour, karaya, guar, tragacanth and agar as well as cellulose derivatives like methyl cellulose, sodium carboxymethyl cellulose, microcrystalline cellulose as well as alginic acids, aluminas and bentonites can be used. These ingredients can be added in amounts of 2 to 30% per weight.

As binding agents, sugar, starches derived from corn, rice and potatoes, natural gums like acacia gum, gelatine and tragacanth, alginic acid, sodium alginate, ammonium calcium alginate, methyl cellulose, waxes, sodium carboxymethyl cellulose, hydroxypropyl methyl cellulose, polyethylene glycol, polyvinyl pyrrolidone as well as inorganic compounds like magnesium aluminum silicate may be added. Binding agents can be added in amounts of 1 to 30% per weight.

As lubricants, boric acid and stearates like magnesium stearate, calcium stearate or potassium stearate, stearic acid, high melting waxes as well as water-soluble lubricants like sodium chloride, sodium benzoate, sodium acetate, sodium oleate, polyethylene glycol and amino acids like leucine can be used. Lubricants can be added in amounts of 0.05 to 15% per weight.

The present invention furthermore relates to pharmaceutical compositions which in addition contain an antiparasitic, antibacterial, antimycotic and/or antiviral active compound.

It is preferred, if the antiparasitic active substances used in combination with a compound of the general formula (I) are selected from the group comprising or consisting of: tinidazole, metronidazole, melarsoprol, eflornithine, rifampin, amphotericin B, pentamidine, sodium stibogluconate, meglumine antimoniate, N-methylglucamine antimonate, fluconazole, artesunate, quinine, quinidine, chloroquine, atovaquone-proguanil, artemether, artemether-lumefantrine, mefloquine, doxycycline, clindamycin, paromomycin, atovaquone, nitazoxanide, azithromycin, fumagillin, paromomycin, diloxanide, secnidazole, ornidazole, iodoquinol, diloxanide furoate, clindamycin, atovaquone, azithromycin, diminazene, praziquantel, oxamniquine, niclosamide, albendazole, mebendazole, thiabendazole, pyrantel, diethylcarbamazine, ivermectin, selamectin, doramectin, abamectin, mefloquine, amodiaquine, artesunate, artemisinin, sulfadoxine-pyrimethamine, proguanil, pyrimethamine, sulfadiazine, sulfamethoxazole-trimethoprim (co-trimoxazole), suramin, eflornithine, melarsoprol, nifurtimox, methylene blue, levamisole and ivermectin. Particularly preferred is a combination with artesunate and/or artemisinin.

It is preferred, if antimycotic active substances used in combination with a compound of the general formula (I) are selected from the group comprising or consisting of: sertaconazole, fluconazole, butoconazole, chlormidazole, enilconazole, fenticonazole, sulconazole, naftifine, clioquinol, iodoquinol, rimoprogin, griseofulvin, terbinafine, clotrimazole, itraconazole, tioconazole, miconazole, miconazole nitrate, glycerol triacetate, tolnaftate, pyrogallol, econazole, posaconazole, isoconazole, terconazole, oxiconazole, voriconazole, amphotericin B, nystatin, natamycin, caspofungin, cilofungin, flucytosine, tolciclate, sulbentine, haloprogin, ketoconazole, ciclopirox, amorolfine, bifonazole, bifonazole/urea, butenafine/urea, urea, sodium propionate, sodium pyrithione and salicylic acid.

Preferred is furthermore if the antibacterial active substances, in particular antibiotics used in combination with a compound of the general formula (I) are selected from the group comprising or consisting of: cell wall synthesis inhibitors like carbapenems: imipenem, meropenem, ertapenem, cephalosporins, monobactams, aztreonam, penicillin, penicillin G (benzylpenicillin), penicillin V (phenoxymethylpenicillin), acylaminopenicillin, piperacillin, mezlocillin, aminopenicillins: ampicillin, amoxicillin, isoxazolyl penicillins, flucloxacillin, methicillin, oxacillin, clavulanic acid, sulbactam, tazobactam, sultamicillin, fosfomycin, glycopeptide, teicoplanin, vancomycin, bacitracin, colistin, gramicidin, polymyxin B, tyrothricin; inhibitors of the ribosomal protein biosynthesis like aminoglycosides, amikacin, gentamicin, kanamycin, neomycin, netilmicin, streptomycin, tobramycin, chloramphenicol, fusidic acid, ketolide, cethromycin, narbomycin, telithromycin, lincosamide, clindamycin, lincomycin, daptomycin, streptogramin, dalfopristin, quinupristin, azithromycin, clarithromycin, erythromycin, roxithromycin, oxazolidinone, linezolid, tetracycline, doxycycline, minocycline, oxytetracycline, tigecycline; gyrase inhibitors (inhibitors of DNA replication) like fluoroquinolones, norfloxacin, ciprofloxacin, enoxacin, ofloxacin, levofloxacin, moxifloxacin, nitroimidazole, metronidazole, tinidazole, aminocoumarin; folic acid antagonists like sulfonamides, sulfadiazine, sulfadoxine, sulfamethoxazole, sulfasalazine, diaminopyrimidine, pyrimethamine, trimethoprime; ansamycins (inhibitor of bacterial RNA polymerase) like rifampicin and inhibitors of metabolic pathways like fosmidomycin.

It is further preferred, if the antiviral active substances used in combination with a compound of the general formula (I) are selected from the group comprising or consisting of: aciclovir, abacavir, didanosine, emtricitabine, lamivudine, stavudine, tenofovir, zidovudine, efavirenz, nevirapine, atazanavir, ritonavir, lopinavir-ritonavir, indinavir, saquinavir, efavirenz-emtricitabine-tenofovir, zidovudine-lamivudine, stavudine-lamivudine-nevirapine, emtricitabine-tenofovir, ribavirine, zidovudine-lamivudine-nevirapine saquinavir, efavirenz-emtricitabine-tenofovir, emtricitabine-tenofovir, stavudine-lamivudine-nevirapine, zidovudine-lamivudine, zidovudine-lamivudine-nevirapine and ribavirine.

Compounds of the present invention and the above described pharmaceutical compositions are used for the treatment and/or prophylaxis of or for the manufacture of a pharmaceutical formulation suitable for the treatment and/or prophylaxis of an infectious disease, which means a disease caused by a parasites virus or by bacteria or a mycotic disease.

Preferred are compounds of the present invention and the above described pharmaceutical compositions for the treatment and/or prophylaxis of or for the manufacture of a pharmaceutical formulation suitable for the treatment and/or prophylaxis of diseases caused by sporozoa and other parasitic infections like for example caused by: *Babesia, Balantidium, Besnoitia, Blastocystis, Coccidia, Cryptosporidium, Cytauxzoon, Cyclospora, Dientamoeba, Eimeria, Entamoeba, Enterocytozoon, Enzephalitozoon, Eperythrozoon, Giardia, Hammondia, Isospora, Leishmania, Microsporidia, Naegleria, Plasmodium, Pneumocystis, Schistosoma, Sarcocystis, Theileria, Trichinella, Toxoplasma, Trichomonas, Trypanosoma, Unicaria, Cestoda, Dipylidium, Dranunculus, Echinococcus, Fasciola, Fasciolopsis, Taenia, Ancylostoma, Ascaris, Brugia, Enterobius, Loa loa, Mansonella, Necator, Oncocerca, Strongyloides, Strongylus, Toxocara, Toxascaris, Trichuris* or *Wucheria*. Particularly preferred are said compounds of the present invention for the treatment and/or prophylaxis of or for the manufacture of a pharmaceutical formulation suitable for the treatment and/or prophylaxis of infections caused by parasites of the genus *Plasmodium* like *Plasmodium falciparum, Plasmodium vivax, Plasmodium ovale, Plasmodium malariae* and *Plasmodium knowlesi* as well as mixed infections with these pathogens.

Also preferred are compounds of the present invention for the treatment and/or prophylaxis of or for the manufacture of a pharmaceutical formulation suitable for the treatment and/or prophylaxis of infections caused by parasites of the genus *Schistosoma* like *S. mansoni, S. haematobium, S. japonicum, S. intercalatum* and *S. mekongi* as well as mixed infections with these pathogens.

Also preferred are compounds of the present invention for the treatment and/or prophylaxis of or for the manufacture of a pharmaceutical formulation suitable for the treatment and/or prophylaxis of infections caused by parasites of the genus *Trypanosoma* like *Trypanosoma brucei* and *Trypanosoma cruzi*.

Preferred are compounds of the present invention and the above described pharmaceutical compositions for the treatment and/or prophylaxis of or for the manufacture of a pharmaceutical formulation suitable for the treatment and/or prophylaxis of parasitic diseases selected from the group comprising or consisting of: trypanosomiasis (African sleeping sickness), chagas diseases, echinococcosis, amoebiasis (amebic dysentery), ancylostomiasis, babesiosis, balantidiasis, blastocystis infection, schistosomosis, bilharziosis (schistosomiasis), coccidioses, cryptosporidiosis, dientamoebiasis, microsporidiosis, zoonoses, giardiasis, isosporiasis, leishmaniosis, *Naegleria* infection, malaria, sarcosporidiosis, piroplasmosis, trichinosis, toxoplasmosis, trochomoniasis, ascariasis, filariosis, taeniasis, echinococcosis, onchocercosis, capillariasis elephantiasis, enterobiasis, sarcosporidiosis, strongyloidiasis, trichuriasis and cysticercosis. Particularly preferred are the compounds of the present invention for the treatment and/or prophylaxis of or for the manufacture of a pharmaceutical formulation suitable for the treatment and/or prophylaxis of malaria, especially of malaria tropica.

Preferred are compounds of the present invention and the above described pharmaceutical compositions for the treatment and/or prophylaxis of or for the manufacture of a pharmaceutical formulation suitable for the treatment and/or prophylaxis of viral diseases of the group comprising or consisting of: influenza (genuine virus flu), cold, cough (caused by rhinoviruses, RSV, parainfluenza viruses), measles, mumps, rubella, fifth disease (erythema infectiosum, caused by parvovirus B19), three-day-fever (exanthema subitum, caused by HHV 6), chickenpox (caused by varicella zoster virus), glandular fever (caused by Epstein-Barr virus), SARS (caused by SARS-associated coronavirus), cytomegalovirus infections, diarrhea (caused by human rotaviruses, adenoviruses), hepatitis A or E (jaundice), poliomyelitis (polio), herpes labialis, warts (human papilloma virus), rabies (lyssa viruses), lassa fever, ebola, Marburg fever, Hantavirus fever, FSME (tick-borne meningoencephalitis), RSSE (Russian spring summer encephalitis), Louping ill encephalitis, Powassan encephalitis, Kyasanur forest fever, Omsk hemorrhagic fever, Colorado tick fever, yellow fever, dengue fever, Japanese encephalitis, West Nile fever, Chikungunya fever, sandfly fever=pappataci fever, Ross river fever, sindbis fever, Mayaro fever, Murray valley encephalitis, St. Louis encephalitis, Rocio encephalitis, California encephalitis, Bunyamwera fever, Oropouche fever, AIDS (caused by HIV), hepatitis B, C, or D, cytomegalovirus infection and herpes genitalis.

Furthermore are compounds of the present invention and the above described pharmaceutical compositions preferably used for the treatment and/or prophylaxis of or the manufacture of a pharmaceutical formulation suitable for the treatment and/or prophylaxis of mycoses. Mycoses are infectious diseases caused by fungi which are parasites in living tissues. The pathogens may belong to the filamentous fungi (dermatophytes), moulds or yeasts. Particularly preferred are compounds of the present invention for the treatment and/or prophylaxis or for the manufacture of a pharmaceutical formulation suitable for the treatment and/or prophylaxis of athlete's foot, thrush of mouth or tongue, nail mycosis, vaginal mycosis and diaper dermatitis. Filamentous fungi (dermatophytes) lead to a superficial infection of "dead" tissue like the horned layer, nails or hair. Yeasts (candida) lead to superficial infections and/or deeper and systemic infections. These fungi are also present in the healthy organism (e.g. in the intestinal tract). A weakened immune defense or a generally poor health conditions are factors which favor spreading of the fungus. This may result in infections of the skin, mucosa or certain organs. Examples are diaper dermatitis, vaginal mycosis or oral thrush (mouth fungus). In the case of a poor general state of health, moulds may also lead to infections of skin, hair, nails or inner organs. Athlete's foot or nail mycoses may be caused by all abovementioned groups of pathogens.

it is preferred, if the mycotic infection is caused by a fungus selected from the group comprising or consisting of *Trichophyton mentagrophytes, Trichophyton rubrum, Trichophyton interdigitale, T. schönleinii, T. verrucosum, T. violaceum, T. tonsurans, Trichophyton* spp., *M. canis, Candida albicans, C. guillermondii, C. krusei, C. parapsilosis, C. tropicalis, C. glabrata, Candida* spp., *Microsporum* spp., *Microsporum canis, Microsporum audonii, Microsporum gypseum, M. ferrugineum, Trichosporum beigelii, Trichosporum inkiin, Aspergillus niger, Alternaria, Acremonium, Fusarium*, and *Scopulariopsis*.

Preferred are compounds of this invention and the above described pharmaceutical compositions for the treatment and/or prophylaxis of or for the manufacture of a pharmaceutical formulation suitable for the treatment and/or prophylaxis of bacterial diseases caused by a bacterium of a genus selected from the group comprising or consisting of: streptococci, staphylococci, enterococci, klebsiellae, *Haemophilus influenzae*, rickettsiae, legionellae, mycobacteria, mycoplasma, ureaplasma, neisseriae, pseudomonadae, bordetellae, corynebacteria, *Corynebacterium diphtheria, Corynebacterium minutissimum*, chlamydia, campylobacteria, *Escherichia coli*, proteus, salmonellae, shigellae, yersiniae, vibrios, clostridia, listeria, borrelia, *Treponema pallidum*, brucellae, francisellae and leptospirae.

It is preferred, if the bacterial infection is caused by a bacterium selected from the group comprising or consisting of: *Allochromatium vinosum, Acinetobacter baumanii, Bacillus anthracis, Campylobacter jejuni, Clostridium* spp., *Citrobacter* spp., *Escherichia coli, Enterobacter* spp., *Enterococcus faecalis, Enterococcus faecium, Francisella tularensis, Haemophilus influenzae, Helicobacter pylori, Klebsiella* spp., *Listeria monocytogenes, Moraxella catharralis, Mycobacterium tuberculosis, Neisseria meningitidis, Neisseria gonorrhoeae, Proteus mirabilis, Proteus vulgaris, Pseudomonas aeruginosa, Salmonella* spp., *Serratia* spp., *Shigella* spp., *Stenotrophomonas maltophilia, Staphyloccocus aureus, Staphyloccocus epidermidis, Streptococcus pneunmoniae, Streptococcus pyogenes, Streptococcus agalactiae, Yersina pestis*, and *Yersina enterocolitiapprox*.

Preferred are the compounds of the present invention and the above described pharmaceutical compositions for the treatment and/or prophylaxis of or the manufacture of a pharmaceutical formulation suitable for the treatment and/or prophylaxis of bacterial diseases of the group comprising of consisting of: caries, pneumonia, sinusitis, otitis media, mastoiditis, bacterial endocarditis, impetigo, erysipelas, phlegmon, tonsillitis; scarlet fewer; sepsis, septic shock, necrotizing fasciitis, furuncle, carbuncle, bullous impetigo, wound infection, osteomyelitis, bacterial joint inflammation, pyodermia, otitis externa, pyometra, typhus, meningitis, Waterhouse-Friderichsen syndrome, gonorrhoea, pertussis, diphtheria, diarrhea infections, borreliosis, syphilis, plague, anthrax, tetanus, typhus, tuberculosis, conjunctivitis, cholera, lepra, type B gastritis, gastric ulcers, duodenal ulcers and tularemia.

The present invention also relates to a method for the treatment and prophylaxis in a patient, comprising the administration of an effective amount of a compound of the present invention of the general formula (I) which is sufficiently high to treat said infectious diseases.

The present invention furthermore refers to the manufacture of hydroxyaryl methylamino-substituted steroids of the present invention. The synthesis of compounds of the general formula (I) is preferably performed according to the following general scheme:

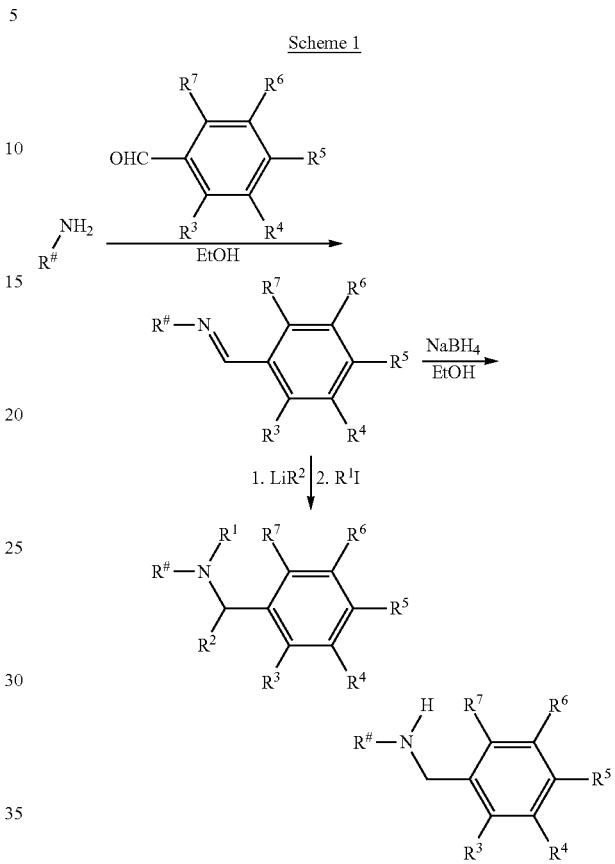

The amino group-functionalized steroid $R^\#$ is converted into imine using an accordingly substituted benzaldehyde, which is reduced to the amine using sodium boron hydride or other suitable reducing agents. Alternatively, addition of a nucleophile to the imine double bond is carried out in the first step, followed by addition of an electrophile.

If steroid residue $R^\#$ carries two or more amino groups, a double or multiple functionalization with the arylmethylamino fragment may be performed, which results in compounds of the general formula (VI).

Alternatively, hydroxyaryl methylamino-substituted steroids of the present invention are available by reductive amination of steroid ketones or aldehydes with respective primary or secondary arylmethylamines, e.g. using $NaBH(OAc)_3$, $NaBH_3CN$, decaborane, pyridine-$BH_3$ adduct with or without addition of Lewis acid catalysts like for example $ZnCl_2$ or $TiCl_4$.

DESCRIPTION OF FIGURES

FIG. 3: Isobolograms for compound 18 with artemisinin and artesunate. For the diagrams, in each case the $FIC_{90}$ values were used.

FIG. 4: Isobolograms for compound 2 ($FIC_{90}$ values) and compound 41 ($FIC_{50}$ values) with artemisinin

Figure 1:
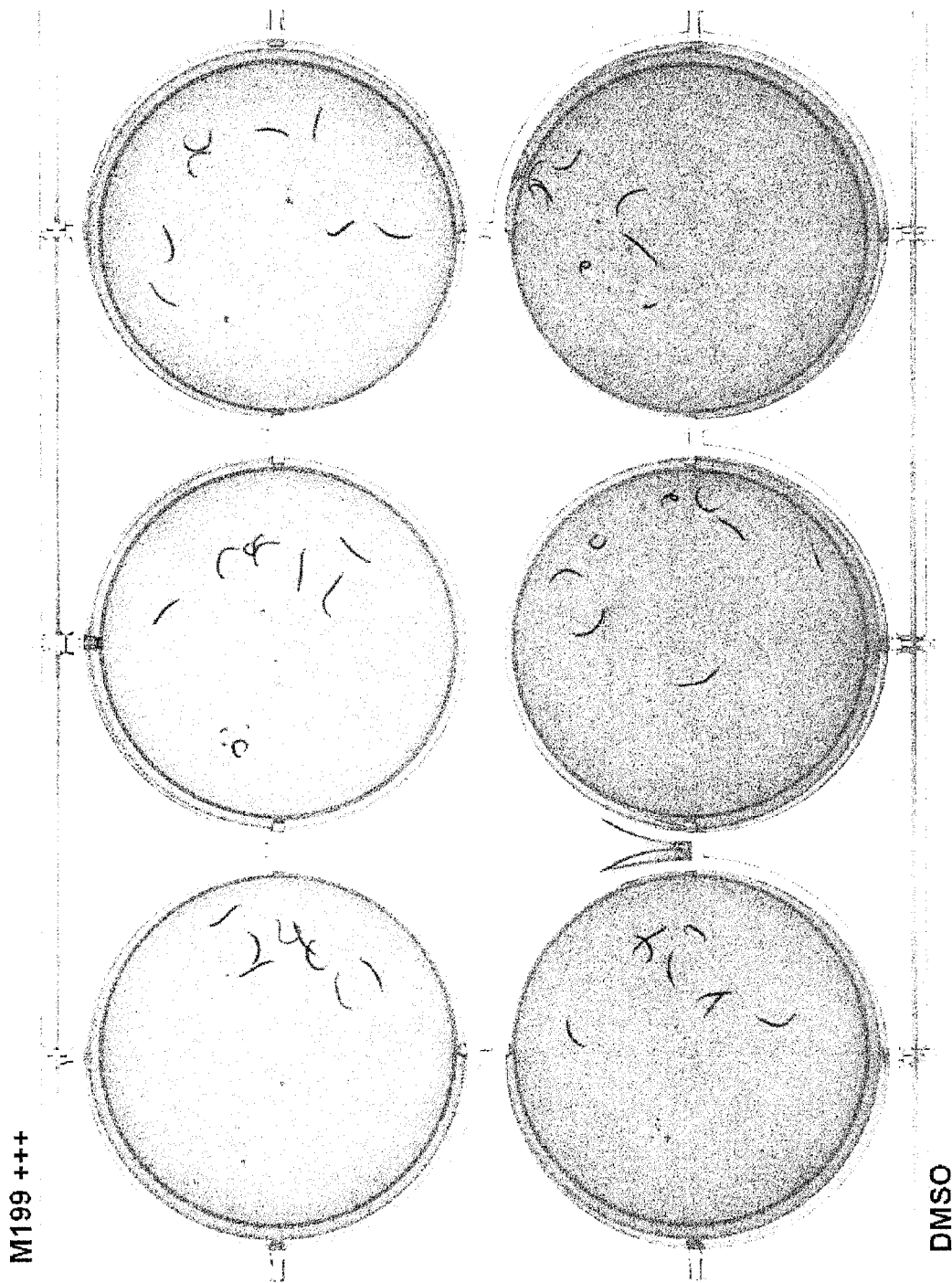
FIG. 1: Eight pairs of adult *S. mansoni* each after 48 hours of incubation in pure medium (M199) and DMSO control

EXAMPLES
Example 1
Synthesis of 16-amino-3-methoxy-estra-1,3,5(10)-triene Precursors to Compounds of the Present Invention in Scheme 1, Starting from Commercially Available Estrone Methylether
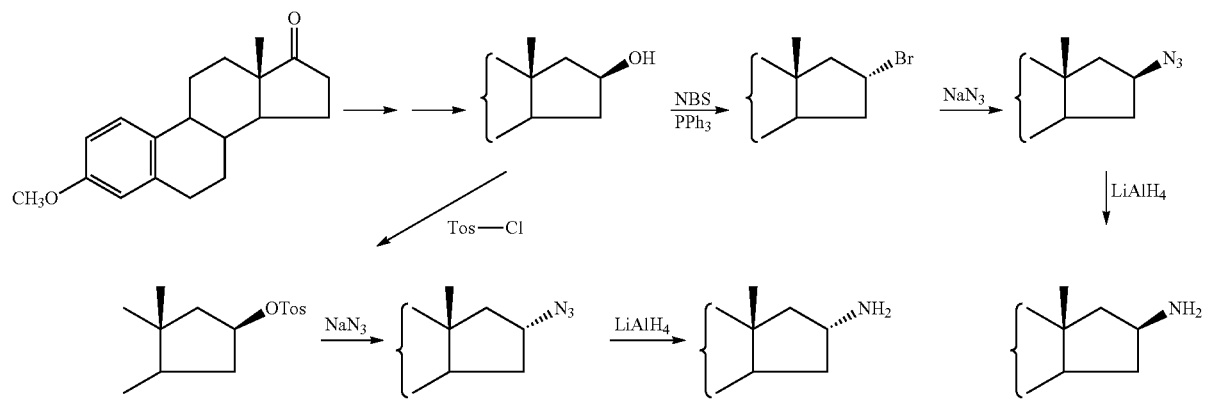
Example 2
Synthesis of 17-amino-estra-3-methoxy-1,3,5(10)-triene Precursors to Compounds of the Present Invention in Scheme 1, Starting from Commercially Available Estrone Methylether
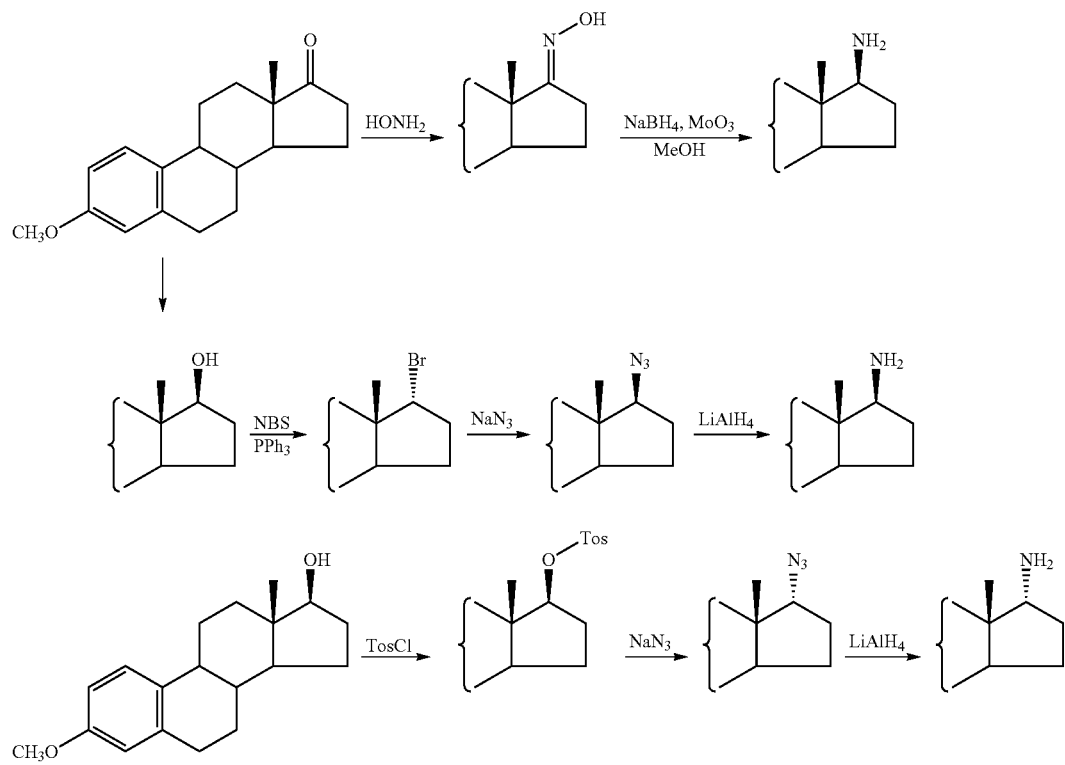

Example 3
Synthesis of 16-amino-17-hydroxy-3-methoxy-estra-1,3,5(10)-triene Precursors to Compounds of the Present Invention in Scheme 1, Starting from Steroid Intermediates Known from the Literature
3.1: 16α-Amino Series
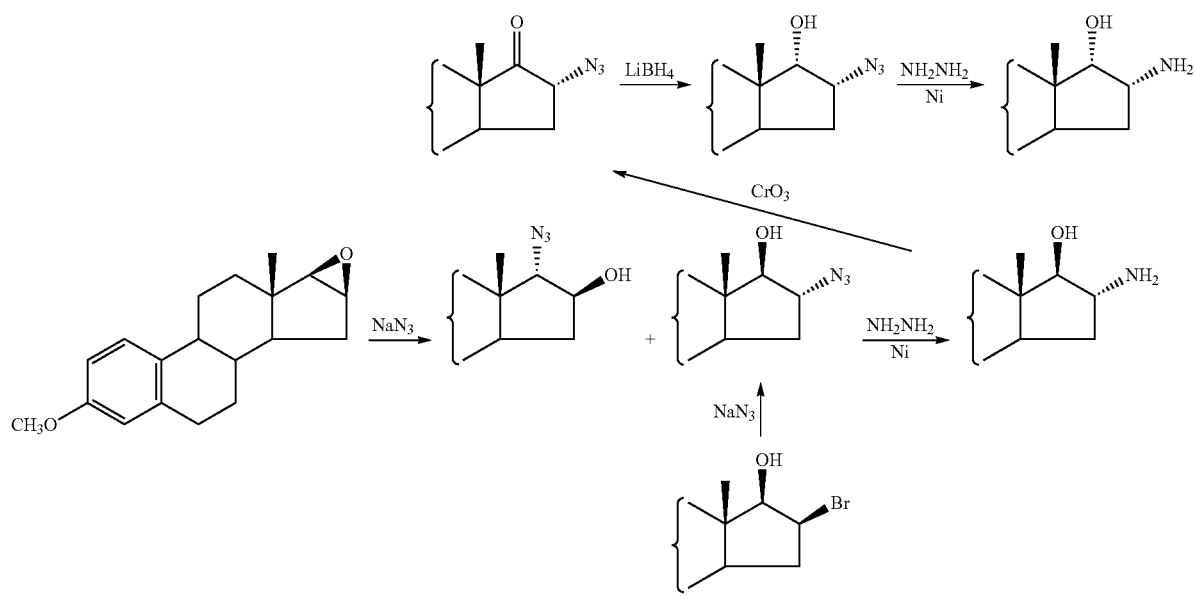
3.2: 16β Amino Series
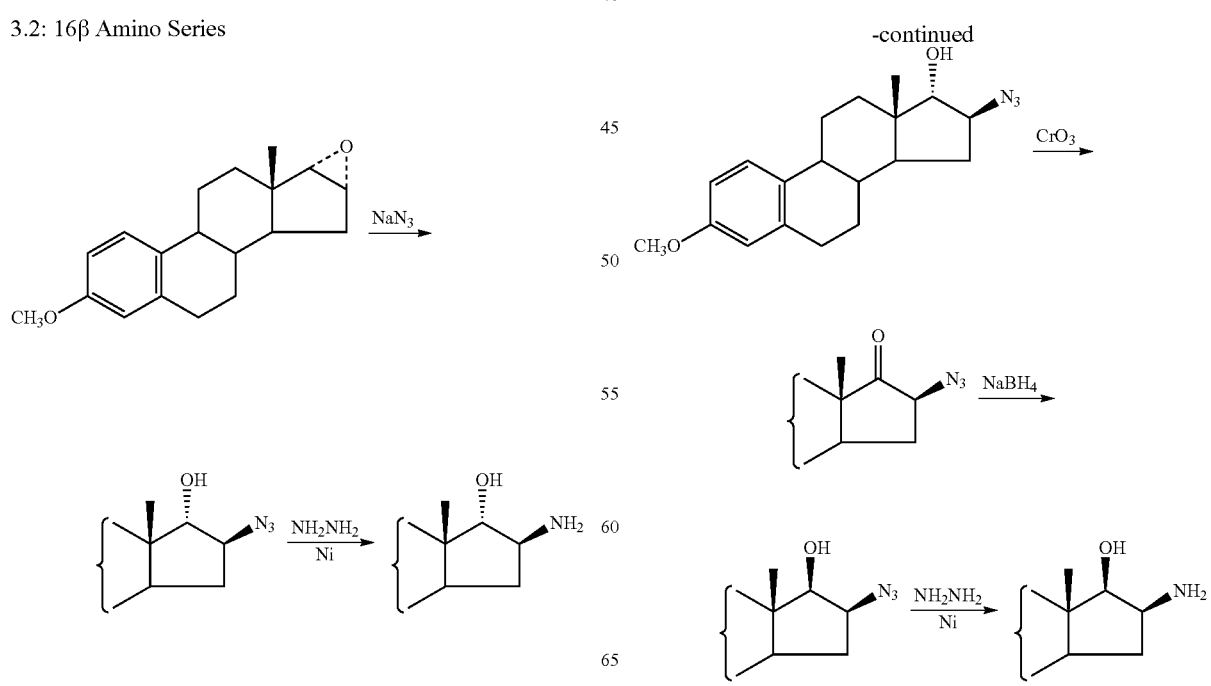

Example 4
Synthesis of Aminocholane Precursors to the Compounds of the Present Invention in Scheme 1, Starting from Steroid Intermediates Known from the Literature
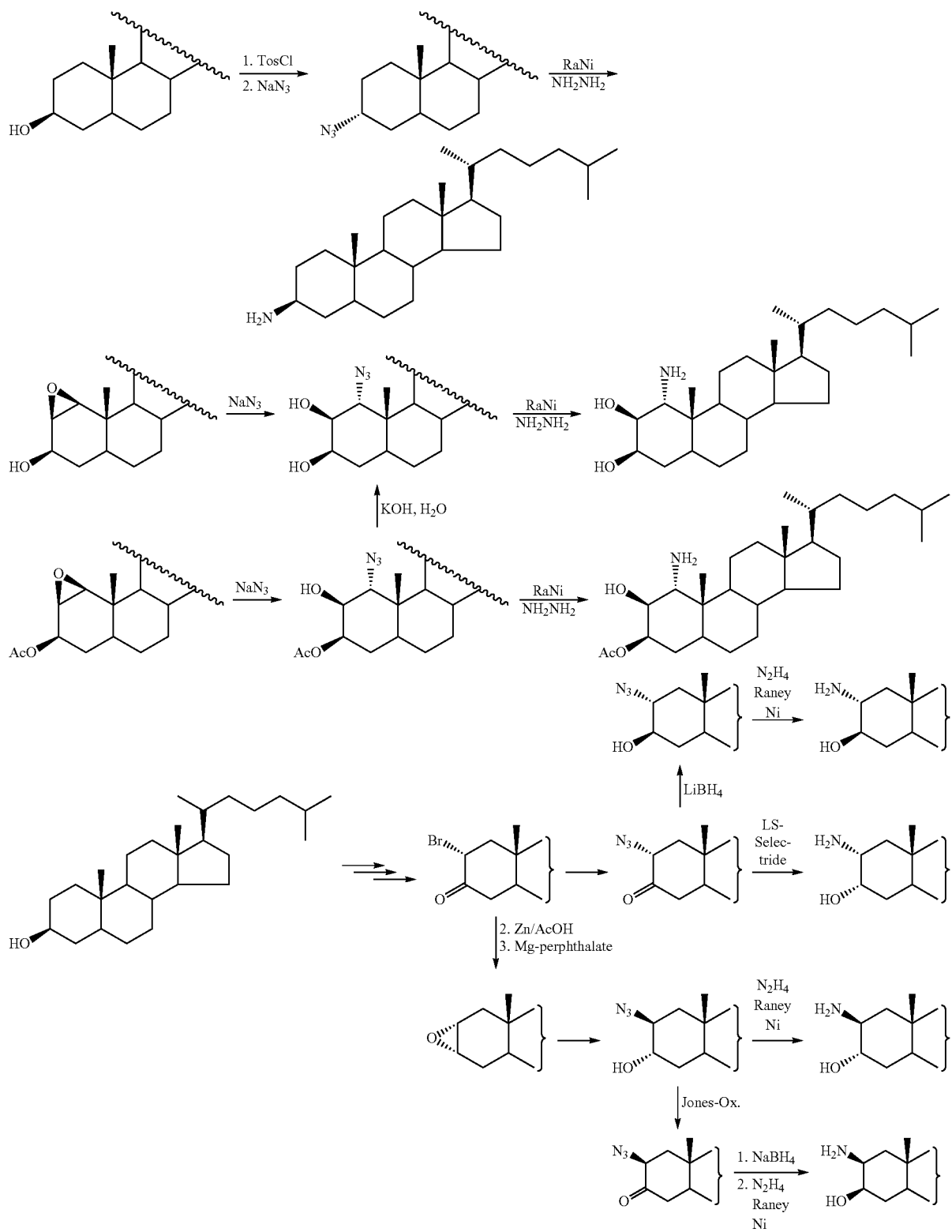

Example 5
Synthesis of 13-Epi-Estratriene Precursors to Compounds of the Present INVENTION in Scheme 1, Starting from Steroid Intermediates Known from the Literature
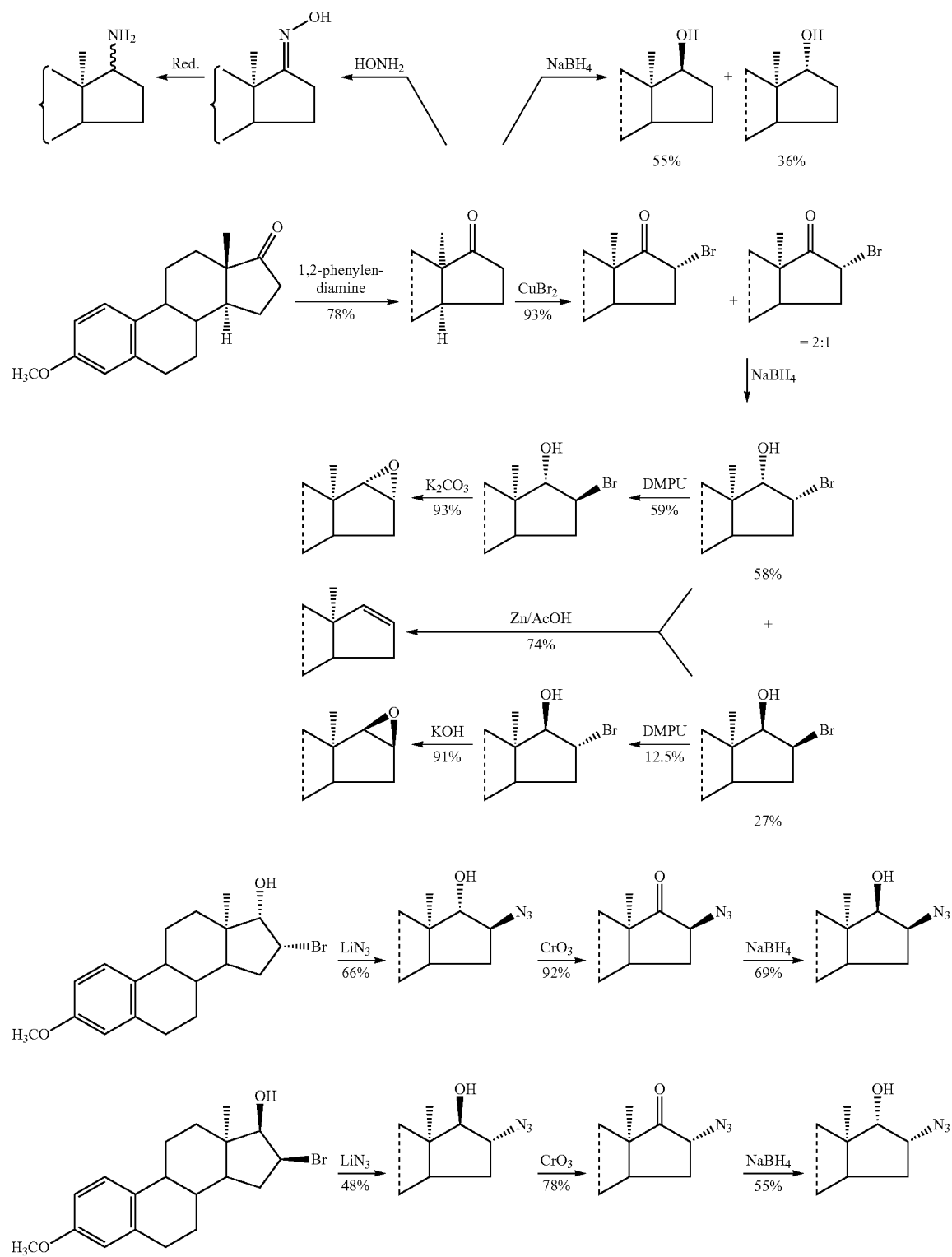
Scheme 5

-continued

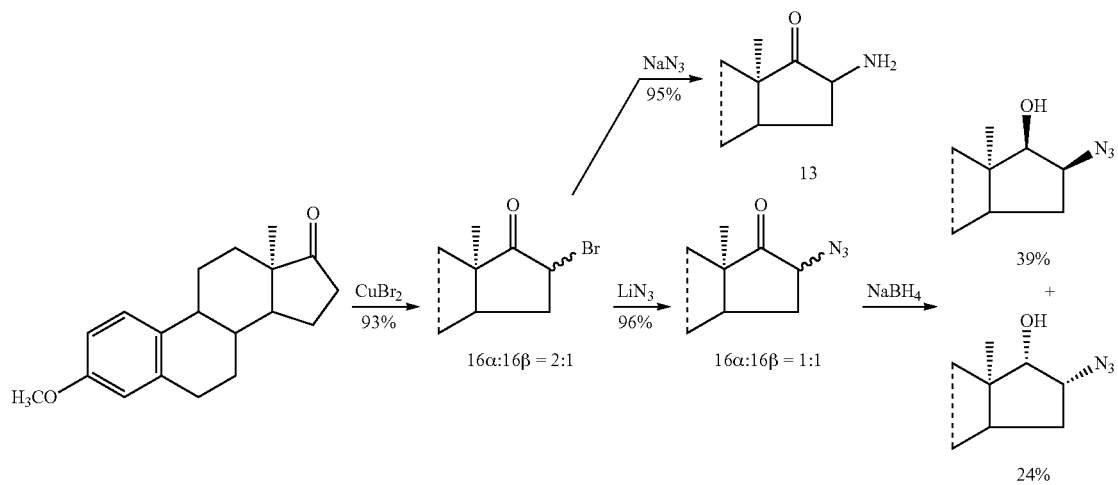

Example 6

Determination of IC$_{50}$ Values in *Plasmodium falciparum* In Vitro

Cultivation of *Plasmodium falciparum* to Determine the Antiparasitic Effect of Benzylamino Steroid Derivatives Chloroquine-sensitive *P. falciparum* strain 3D7-Netherlands and chloroquine-sensitive *P. falciparum* strain K1 were kept in continuous culture according to internationally accepted and repeatedly published standards, as described by our group amongst others in Akoachere et al. (In Vitro Assessment of Methylene Blue on Chloroquine-Sensitive and -Resistant *Plasmodium falciparum* Strains Reveals Synergistic Action with Artemisinins; Antimicrobial Agents and Chemotherapy, 2005, Vol. 49, 4592-4597). Parasites were cultivated at 1 to 10% parasitemia and 3.3% hematocrit in an RPMI 1640 culture medium (Gibco, Invitrogen) supplemented with A+erythrocytes, 0.5% bovine serum albumin (Albumax, Invitrogen), 9 mM (0.16%) glucose, 0.2 mM hypoxanthine, 2.1 mM L-glutamine and 22 µg/ml gentamicin. All incubations were carried out at 37° C. in a Heraeus/Thermo Scientific Cytoperm 2-Incubator under constant gassing with 3% $O_2$, 3% $CO_2$ and 94% $N_2$. Synchronization of parasites in culture to ring stages as start population was carried out by repeated treatment of parasitized erythrocytes with 5% (w/v) sorbitol (each 3 minutes at 37° C.), followed by centrifugation (3 minutes at 900×g, room temperature) and 1× washing with the abovementioned supplemented RPMI medium. After a further centrifugation step (3 minutes, 900×g), parasites were resuspended in 10 ml medium (hematocrit 5%). The obtained parasites in the ring stage of development were incubated for 48 h (1 development cycle) and then utilized for the assessment of the benzylamino steroid derivatives.

Determination of IC$_{50}$ Values In Vitro

A radioactive sensitivity assay was used to determine the susceptibility of *P. falciparum* for different compounds of the general formula (I). This procedure is based on the incorporation of radioactive $^3$H-hypoxanthine which is taken up by the parasite as precursor for purine deoxynucleotides for DNA synthesis. A dilution series (total of 8 twofold serial dilutions) of the in initial concentration (50 ng/ml) of the pharmacologically effective compound of the formula (I) was prepared in 96-well microtiter plates for suspension cultures (Greiner). Parasites were initially incubated for 48 h at a parasitemia of 0.1% (>90% ring stage) and 1.25% hematocrit in hypoxanthine-free medium (total volume 200 µl) with inhibitory substances. Then, 0.5 µCi $^3$H-hypoxanthine was added to each well and plates were incubated for further 24 hours. The cells of each well were then harvested on a glass fiber filter (Perkin-Elmer, Rodgau-Jügesheim, Germany), washed with distilled water and dried in an oven (60-70° C., 1 h). The radioactivity in counts per minute was measured on a beta counter and was proportional to the number of survivable parasites on the glass fiber plate before the harvesting step. All IC$_{50}$ values were determined in quadruplicates. In each assay, a chloroquine control was performed in parallel.

Result

Compound 1 exhibited an in vitro activity of IC$_{50}$=73 nM with respect to the chloroquine-resistant *Plasmodium falciparum* strain K1, and 50 nM with respect to 3D7 (see table 1). This compound has a low cytotoxicity IC$_{50}$=11 µM (SI=217). Compounds 3 and 4 have a comparable activity. Interesting however was that compound 2 is much more effective for strain 3D7 with an IC$_{50}$ value of 7.4 nM (SI=1071).

TABLE 1

| | In vitro activities | | | | |
|---|---|---|---|---|---|
| | | | IC$_{50}$ [µg/ml] | | |
| | IC$_{50}$ [nM] | IC$_{50}$ [ng/ml] | Antiproliferative activity | | Cytotoxicity |
| Compound | P.f.(3D7) | | L929 | K562 | HeLa |
| 1 | 50 | 19.8 | 2.2 | 0.8 | 4.3 |
| 2 | 7.4 | 2.9 | 1.9 | 0.5 | 3.1 |
| 3 | 62 | 24.5 | 1.9 | 0.7 | 4.4 |

TABLE 1-continued

| | In vitro activities | | | | |
| | | | IC$_{50}$ [µg/ml] | | |
| Compound | IC$_{50}$ [nM] P.f.(3D7) | IC$_{50}$ [ng/ml] | Antiproliferative activity L929 | K562 | Cytotoxicity HeLa |
| --- | --- | --- | --- | --- | --- |
| 4 | 41.5 | 16.4 | 1.6 | 1.3 | 4.7 |
| 5 | 879 | 578 | — | — | — |
| 6 | 440 | 172 | — | — | — |
| 7 | 115 | 45 | — | — | — |
| 17 | 72.8 | 32.1 | — | — | — |
| 18 | 7.0 | 3.1 | | | |
| 19 | 182 | 98.60 | — | — | — |
| 20 | 733 | 287 | — | — | — |
| 21 | 465 | 237 | — | — | — |
| 23 | 716.10 | 331.3 | — | — | — |
| 26 | 11.0 | 4.7 | | | |
| 27 | 62.1 | 26.4 | | | |
| 28 | 114 | 49.6 | | | |
| 29 | 42 | 19.8 | | | |
| 30 | 210 | 85.5 | | | |
| 31 | 625 | 265 | | | |
| 32 | 29.9 | 13.7 | | | |
| 33 | 919 | 389 | | | |
| 34 | 54.6 | 24.2 | | | |
| 36 | 42.1 | 19.3 | | | |
| 37 | 99.2 | 43.9 | | | |
| 38 | 208 | 106 | | | |
| 41 | 4.4 | 1.9 | | | |
| 42 | 227 | 91.3 | — | — | — |
| 43 | 58.5 | 23.9 | 2.0 | 1.2 | 7.7 |
| 44 | 675.5 | 275 | 2.5 | 0.85 | 3.4 |
| 45 | 101 | 41 | — | — | — |
| 46 | 998 | 393 | — | — | — |
| 47 | 140.5 | 57.3 | — | — | — |
| 48 | 83.3 | 34.0 | — | — | — |
| Ref 1 | 1608 | 836 | | | |

Example 7

Determination of IC$_{50}$-Values Using *Plasmodium berghei* in the Mouse Model (In Vivo)

To assess the efficacy of benzylamino steroid derivatives in vivo, compounds 1 and 2 were investigated in a mouse model with *Plasmodium berghei* infection (s. also Peters and Robinson, Handbook of Animal Models in Infection; Chapter 92, Malaria, Academic Press, London, United Kingdom, 1999 and Sturm et al. Compounds Structurally Related to Ellagic Acid Show Improved Antiplasmodial Activity, Antimicrobial Agents and Chemotherapy, 2009, Vol. 53, 622-630). These experiments were carried out at the Swiss Tropical Institute under the direction of Dr. Sergio Wittlin according to internationally accepted standards. One day after infection of animals with *Plasmodium berghei* GFP MRA-865, the compounds were dissolved in tween/alcohol and applied either subcutaneously or orally with each one dosage per day on three consecutive days after infection. Subcutaneously applied were 3×10 mg/kg or 3×30 mg/kg, the oral dosage was 3×10 mg/kg, 3×30 mg/kg or 3×100 mg/kg. On day 4, Giemsa-stained blood smears of mice were investigated with respect to parasitemia (counting parasitized erythrocytes under the light microscope). As additional parameter, the survival time was determined. Infected but untreated mice were euthanized on day 4, due to the severity of symptoms.

Result:

In vivo activities of compounds 1 and 2 are given in table 2. Compounds are effective both after subcutaneous as well as after oral application on *Plasmodium berghei* blood stages in the mouse, which is most clearly demonstrated in the dosage-dependent reduction of parasitemia as compared to untreated control animals. All dosages and routes of administration tested furthermore considerably extended the life span.

TABLE 2

In vivo activity (indicated in % of parasitemia of untreated controls (n = 5)) of compounds 1 and 2 as compared to chloroquine.

| Application/ dosage | MSD (days) compound 1 | Activity (%) 1 | MSD (days) compound 2 | Activity (%) 2 | MSD (days) control | MSD chloroquine ip 3 × 10 mg/kg | Activity (%) chloroquine |
| --- | --- | --- | --- | --- | --- | --- | --- |
| sc 3 × 10 mg/kg | 10.2 (n = 3) | 47 | 7 (n = 3) | 17.7 | 4 (euth.) | 13.6 | 99.6 |
| sc 3 × 30 mg/kg | 15 (n = 3) | 94 | 14 (n = 3) | 61.8 | 4 (euth.) | 13.6 | 99.6 |
| oral 3 × 10 mg/kg | nd | nd | 8.7 (n = 3) | 46.8 | nd | nd | nd |
| oral 3 × 30 mg/kg | nd | nd | 13 (n = 3) | 99.4 | nd | nd | nd |
| oral 3 × 100 mg/kg | 16.3 (n = 3) | 99 | 15.33 (n = 3) | 99.7 | 4 (euth.) | 13.6 | 99.6 |

(sc = subcutaneous;

ip = intraperitoneal;

MSD = mean survival days).

Example 8

Synthesis and Characterization of Compounds

Experimental Details—General Information Concerning the Embodiment Examples

Melting points (corrected): micro hot stage according to BOËTIUS.—EA: Foss-Heraeus CHN-O-RAPID or micro analysis according to Knobloch, M given in g/mol.—Mass spectra: AMD 402, El.—IR: Shimadzu IR-470; ν given in cm$^{-1}$.—UV (in acetonitrile): Specord M-40 (Carl Zeiss Jena).—Specific rotational value: Polamat A (Carl Zeiss Jena) or PROPOL DIGITAL automatic polarimeter (Dr. Kernchen), measured at room temperature in chloroform (c=1) unless stated otherwise; c given in g 100$^{-1}$ ml$^{-1}$.—$^1$H- and $^{13}$C-NMR: Bruker AC 200, WP 200 SY and AMX 400; in CDCl$_3$, TMS as internal standard; δ in ppm; measured in CDCl$_3$ at 250 MHz ($^1$H) unless stated otherwise—DC: Merck aluminum backed plates silica gel 60 F$_{254}$ or Fluka aluminum-coated plates (Al$_2$O$_3$), UV detection or detection by spraying with a mixture of 80 ml conc. sulphuric acid, 20 ml ethanol, 200 mg vanillin and subsequent visualization at 170° C.; eluent:ethyl acetate/n-hexane (1:2) unless stated otherwise. Used solvents and liquid reagents are, unless commercially available, purified and dried according to generally used procedures. Condensation reactions with aryl aldehydes are preferably performed under argon in the absence of moisture. Raw products are dried at ≈5 Torr for several hours over phosphorus pentoxide at room temperature.

In the following, representative examples and data are given in detail.

Synthesis of Hydroxyaryl Methylamino-Substituted Steroids of the Present Invention—Illustrated with a Scheme Describing the Condensation of Amino Steroids with Carbonyl Compounds to Yield Azomethines, and Subsequent Reduction Thereof According to Example 1

General Protocol for the Condensation of Amino Steroids with Carbonyl Compounds to azomethines 1 mmol of steroid amino alcohol is dissolved in 15 ml abs. methanol under heating, then 1.1 mmol of the carbonyl compound is added. After stirring for 30 min at 60° C. and cooling to room temperature, the precipitated reaction product is filtered off, washed with methanol, dried and preferably directly processed further. Non-precipitating reaction products may also directly be reduced with NaBH$_4$ to the respective steroid arylamines without further purification as described below. Alternatively, the synthesis may be carried out in ethanol. For reactive aldehydes like e.g. salicylaldehyde, reactions are preformed at room temperature.

General Instructions

Exemplarily Shown for the Synthesis of 16β-(2-hydroxyphenyl-carbaldimino)-estra-3,17β-diol-3-methyl ether 3 mmol (904.2 mg) of 16β-amino-estra-3,17β-diol-3-methyl ether are dissolved in ml of absolute methanol and 3.3 mmol (403 mg, 346 μl) freshly distilled salicylaldehydes are added under constant stirring at room temperature. After approx. 3 hours, the mixture is reduced to 50% of the initial volume and cooled. The precipitate is filtered off, and washed with methanol. After drying 1.3 g (97%) 16β-(2-hydroxyphenylmethylenimino)-estra-3,17β-diol-3-methylether are obtained in the form of a bright, lemon yellow, fine crystalline product ($^1$H-NMR: more or less homogeneous, no signal at 5.6 ppm). Recrystallization was performed by dissolving in approx. 30 ml boiling ethyl acetate and subsequent addition 15 ml hot heptane: 1.0 g (75%), bright yellow needles or columns, m.p. 221-224° C.

C$_{26}$H$_{31}$NO$_3$ (405.56), calc.: C, 76.99; H, 7.71; N, 3.47. found: C, 77.01; H, 7.71; N, 3.75; [α]$_D$+47.40.

$^1$H-NMR: 0.90 (s, 3H, 18-H$_3$), 1.13-2.31 (m, overl., 12H), 2.79 (m, 2H, 6-H$_2$), 3.66 (t, $^3$J=8.5 Hz, 1H, 17α-H), 3.70 (s, 3H, 3-MeO), 3.84 (m, 1H, 16αH), 6.55-7.25 (m, overl., 7H, 1-H, 2-H, 4-H and phenyl-H$_4$), 8.30 (s, 1H, N=CH).

$^{13}$C-NMR (CDCl$_3$): 12.1 (C-18), 34.4 (C-15), 37.1 (C-12), 43.4 (C-13), 47.9 (C-14), 69.0 (C-16), 55.5 (OCH$_3$), 82.9 (C-17), 166.3 (N=CH).

In the same manner, obtained are for example:

17β-(4-N,N-Diethylamino-2-hydroxyphenyl-carbaldimino)-3-methoxy-estra-1,3,5(10)-triene (24)

obtained by conversion of 17β-amino-3-methoxy-estra-1,3,5(10)-triene) and 4-(N,N-diethylamino)salicylaldehyde in abs. ethanol.

C$_{30}$H$_{40}$N$_2$O$_2$ (460.65), F=234.5-235.5° C. (from EtOH), R$_f$=0.48.

$^1$H-NMR: 0.890 (s, 3H, 18-H$_3$), 1.190 (t, $^3$J=7.0 Hz, 6H, 2×CH$_3$—CH$_2$), 1.200-2.311 (m, overl., 13H), 2.862 (s, broad, 2H, 6-H$_2$), 3.173 (t, $^3$J=8.7 Hz, 1H, 17α-H), 3.373 (q, $^3$J=7.0 Hz, 4H, 2×CH$_3$—CH$_2$), 3.780 (s, 3H, 3-MeO), 6.084 (s, 1H, phenyl-H), 6.138 (d, $^3$J=8.4 Hz, 1H, phenyl-H), 6.628 (d, $^3$J=8.4 Hz, 1H, phenyl-H), 6.643 (s, 1H, 4-H), 6.69 (d, $^3$J=8.6 Hz, 1H, 2-H), 7.204 (d, $^3$J=8.6 Hz, 1H, 1-H), 7.957 (s, 1H, CH=N), 14.260 (s, broad, 1H, OH).

$^{13}$C-NMR: 12.70, 12.75, 24.02, 25.60, 26.13, 27.61, 29.66, 29.84, 36.88, 38.86, 43.95, 44.49, 44.74, 52.23, 55.19, 76.87, 77.20, 98.65, 102.90, 108.36, 111.44, 113.80, 126.30, 132.58, 132.69, 137.94, 151.76, 157.45, 161.03, 168.04.

17β-(3-Hydroxy-naphth-2-carbaldimino)-3-methoxy-estra-1,3,5(10)-triene (25)

obtained by conversion of 17β-amino-3-methoxy-estra-1, 3,5(10)-triene) and 3-hydroxy-naphth-2-carbaldehyde in abs. ethanol.

C$_{30}$H$_{33}$NO$_2$ (339.59), F=234.5-236.5° C. (from EtOH/THF=1:1), R$_f$=0.76.

$^1$H-NMR (selected data): 0.960 (s, 3H, 18-H$_3$), 2.880 (s, (s, broad, 1H, OH), 2H, 6-H$_2$), 3.296 (t, $^3$J=8.6 Hz, 1H, 17α-H), 3.782 (s, 3H, 3-MeO), 6.661 (m, 1H, 4-H), 6.780 (d, $^3$J=7.5 Hz, 1H, 2-H), 7.264 (d, $^3$J=7.5 Hz, 1H, 1-H), 7.304-7.769 (m, approx. 6H, 6× naphthyl-H), 8.530 (s, 1H, N=CH), 13.303 (s, broad, 1H, OH).

$^{13}$C-NMR: 13.11, 24.37, 26.13, 27.71, 29.85, 30.06, 36.98, 38.79, 43.94, 45.45, 52.53, 55.20, 80.09, 110.84, 111.47, 113.84, 121.30, 123.30, 126.31, 127.29, 127.92, 128.31, 132.51, 132.57, 133.75, 137.94, 157.11, 157.49, 163.14.

17α-(3-Hydroxy-naphth-2-carbaldimino)-3-methoxy-estra-1,3,5(10)-triene obtained by conversion of 17α-Amino-3-methoxy-estra-1, 3,5(10)-triene) and 3-hydroxy-naphth-2-carbaldehyde in abs. ethanol.

C$_{30}$H$_{33}$NO$_2$ (339.59), F=246-248° C. (from EtOH/THF=1:1), R$_f$=0.82.

17β-[(E)-salicylidene imino)-3-methoxy-estra-1,3,5(10)-triene obtained by conversion of 17β-amino-3-methoxy-estra-1, 3,5(10)-triene) and salicylaldehyde in abs. ethanol.

$C_{26}H_{31}NO_2$ (389.54), F=85-88° C. (from MeOH), $R_f$=0.56, $[\alpha]_D$+105.8° (c=9.837).

$^1$H-NMR: 0.864 (s, 3H, 18-H$_3$), 2.876 (s, broad, 2H, 6-H$_2$), 3.222 (t, $^3$J=7.5 Hz, 1H, 17α-H), 3.764 (s, 3H, 3-MeO), 6.672 (m, 2H, 2- and 4-H), 6.910 (m, 2H, 3- and 5-phenyl-H), 7.256 (m, 3H, 1-H and 4-H and 6-phenyl-H), 8.273 (s, 1H, N=CH), 13.866 (s, 1H, 2-phenyl-OH).

$^{13}$C-NMR: (incl. DEPT 135): 13.0 (18-CH$_3$), 24.3 (15-C), 26.1 ((11-C), 27.7 (7-C), 29.8 (6-C), 29.9 (12-C), 36.9 (16-C), 55.2 (CH$_3$O), 79.6 (17-C), 111.4 (2-C), 113.9 (4-C), 126.3 (1-C), 132.5 (10-C), 137.9 (5-C), 157.4 (3-C), 163.1 (CH=N); phenyl-C: 117.0, 118.3, 118.9, 131.0, 132.0, 161.5.

IR: 1630 (s, C=N valence); 1610 (m), 1579 (w), and 1497 (s, arom. C=C).

17α-[(E)-Salicylidene imino)-3-methoxy-estra-1,3,5(10)-triene obtained by conversion of 17α-amino-3-methoxy-estra-1,3,5(10)-triene) and salicylaldehyde in abs. ethanol.

$C_{26}H_{31}NO_2$ (389.54), F=161-162.5° C. (from MeOH), $[\alpha]_D$–116.3° (c=8.432).

$^1$H-NMR: 0.864 (s, 3H, 18-H$_3$), 2.855 (m, broad, 2H, 6-H$_2$), 3.357 (d, J=6.6 Hz, 1H, 17β-H), 3.760 (s, 3H, 3-MeO), 6.662 (m, 2H, 2-und 4-H), 6.889 (m, 2H, 3- and 5-Phenyl-H), 7.254 (m, 3H, 1-H and 4-H and 6-phenyl-H), 8.246 (s, 1H, N=CH), 13.754 (s, 1H, 2-phenyl-OH).

$^{13}$C-NMR: (incl. DEPT 135): 18.5 (18-CH$_3$), 25.1 (15-C), 26.4 ((11-C), 28.1 (7-C), 30.0 (6-C), 31.7 (12-C), 33.4 (16-C), 55.2 (CH$_3$O), 78.7 (17-C), 111.5 (2-C), 113.8 (4-C), 126.4 (1-C), 132.0 (10-C), 138.0 (5-C), 157.4 (3-C), 162.0 (CH=N); phenyl-C: 116.9, 118.5, 118.8, 131.1, 132.8, 161.0.

16β-[(E)-Salicylidene imino]-3-methoxy-estra-1,3,5(10)-triene

Obtained by conversion of 16β-amino-3-methoxy-estra-1,3,5(10)-triene) and salicylaldehyde in abs. methanol.

$C_{26}H_{31}NO_2$ (389.54), yield 90%, F=181-183 (from methanol), $[\alpha]_D$+24.6° (c=7.315), $R_f$=0.74.

$^1$H-NMR: 1.02 (s, 3H, 18-H$_3$), 3.76 (s, 3H, OCH$_3$), 3.88 (m, 1H, 16α-H), 6.61-7.30 (7H, Ar—H), 8.25 (s, 1H, CH=N), 13.70 (s, 1H, —XH).

$^{13}$C-NMR: 19.1 (C-18), 26.5 (C-11), 28.1 (C-7), 29.8 (C-6), 35.9 (C-15), 38.8 (C-12), 38.6 (C-8), 41.4 (C-13), 43.9 (C-9), 50.0 (C-17), 53.6 (C-14), 55.2 (OCH$_3$), 67.1 (C-16), 111.5 (C-2), 113.8 (C-4), 126.2 (C-1), 132.7 (C-10), 137.8 (C-5), 157.4 (C-3), 162.1 (CH=N); Ar—C: 116.9, 118.4, 118.8 (q), 131.0, 131.9, 161.1 (q).

Calc. C, 80.16; H, 8.02; N, 3.67. found: 80.39, 8.39, 3.67.
IR: 1630 (CH=N), 1582, 1503.

16α-[(E)-Salicylidene imino]-3-methoxy-estra-1,3,5(10)-triene obtained by conversion of 16α-amino-3-methoxy-estra-1,3,5(10)-triene) and salicylaldehyde in abs. methanol.

$C_{26}H_{31}NO_2$ (389.54), yield 88%, F=118-120 (from methanol), $[\alpha]_D$+126.4° (c=8.027), $R_f$=0.77.

$^1$H-NMR: 0.84 (s, 3H, 18-H$_3$), 3.76 (s, 3H, OCH$_3$), 3.97 (m, 1H, 16β-H), 6.61-7.30 (7H, Ar—H), 8.27 (s, 1H, CH=N), 13.68 (s, 1H, —XH).

$^{13}$C-NMR: 18.7 (C-18), 26.4 (C-11), 28.0 (C-7), 29.6 (C-6), 35.5 (C-15), 38.4 (C-12), 38.9 (C-8), 42.3 (C-13), 43.8 (C-9), 50.5 (C-17), 52.1 (C-14), 55.2 (OCH$_3$), 66.9 (C-16), 111.4 (C-2), 113.8 (C-4), 126.2 (C-1), 132.7 (C-10), 137.9 (C-5), 157.4 (C-3), 162.0 (CH=N); Ar—C: 116.9, 118.4, 118.8 (q), 131.0, 131.8, 161.1 (q).

Calc. C, 80.16; H, 8.02; N, 3.67. found: 80.01, 8.09, 3.77.

17β-Hydroxy-16α-(E)-salicylidene imino-3-methoxy-estra-1,3,5(10)-triene obtained by conversion of 16α-amino-17β-hydroxy-3-methoxy-estra-1,3,5(10)-triene) and salicylaldehyde in abs. methanol.

$C_{26}H_{31}NO_3$ (405.56). Calc. C, 76.99; H, 7.71; N, 3.47. found: C, 76.82; H, 7.87; N, 3.54.

Recrystallization from methanol, yield: 89%, F=169-172° C., $[\alpha]_D$+81.7° (c=0.969).

$^1$H-NMR: 0.89 (s, 3H, 18-H$_3$); 3.63 (m, 1H, 16β-H); 3.70 (d, $^3$J=6.5 Hz, 1H, 17α-H); 3.77 (s, 3H, OCH$_3$); 6.62 (d, $^4$J=2.8 Hz, 1H, 4-H); 6.70 (dd, $^3$J=8.5 Hz, $^4$J=2.8 Hz, 1H, 2-H); 6.86 (m, 1H, C$_6$H$_4$); 6.94 (m, 1H, Ar—H); 7.17-7.32 (m, 3H, 1-H and Ar—H); 8.31 (s, 1H, N=CH).

$^{13}$C-NMR: 12.23 (s, C-18), 25.97 (s, C-11), 27.11 (s, C-7), 29.68 (s, C-6), 32.78 (s, C-15), 36.49 (s, C-12), 38.42 (s, C-8), 43.87 (s, C-9), 43.99 (s, C-13), 48.36 (s, C-14), 55.15 (s, OCH$_3$), 74.64 (s, C-16), 87.91 (s, C-17), 111.47 (s, C-2), 113.75 (s, C-4), 116.91, 118.59 (23 s, C$_6$H$_4$), 118.66 (s, C—C$_6$H$_4$), 126.23 (s, C-1), 131.24, 132.12 (2×s, Ar—C), 132.29 (s, C-10), 137.83 (s, C-5), 157.42 (s, C-3), 161.04 (s, HO—Ar), 163.87 (CH=N).

16α-[(E)-3-Hydroxy-salicylidene imino]-17β-hydroxy-3-methoxy-estra-1,3,5(10)-triene obtained by conversion of 16α-amino-17β-hydroxy-3-methoxy-estra-1,3,5(10)-triene) and 2,3-dihydroxybenzaldehyde in abs. methanol.

$C_{26}H_{31}NO_4$ (421.54). Calc. C, 74.79; H, 7.41; N, 3.32. found: C, 73.36; H, 7.45; N, 3.28.

Recrystallization from ethyl acetate under slow addition of ether, then petroleum ether, yield: 82%, F=109-114° C., $[\alpha]_D$+80.0° (c=10.037).

MS (FAB): 421.5 (M$^+$), 138.1 (100%).

$^1$H-NMR: 0.863 (s, 3H, 18-H$_3$), 2.830 (m, 2H, 6-H$_2$), 3.678-3.738 (m, overl., 2H, 16(3-H und 16α-H), 3.767 (s, 3H, OCH$_3$), 3.88 (m, 1H, 6.530-6.726 (m, overl., 4H, 4×Ar—H), 6.910 (d, $^3$J=8.9 Hz, 1H, 2-H), 7.171 (d, $^3$J=8.9 Hz, 1H, 1-H), 8.120 (s, 1H, CH=N).

$^{13}$C-NMR: 12.04, 25.92, 27.10, 29.65, 32.28, 36.33, 38.37, 43.80, 43.92, 48.29, 55.21, 71.36, 87.75, 111.57, 113.84, 115.90, 116.36, 116.70, 122.31, 126.23, 132.20, 137.78, 146.52, 156.29, 157.54, 163.99.

3,17β-Dihydroxy-16α-(E)-salicylidene imino-estra-1,3,5(10)-triene obtained by conversion of 16α-amino-3,17β-dihydroxy-estra-1,3,5(10)-triene) and salicylaldehyde in abs. methanol.

$C_{25}H_{29}NO_3$ (391.53), calc. C, 76.69; H, 7.47; N, 3.58. found: C, 76.36; H, 7.18; N, 3.56; F=235-238° C., $[\alpha]_D$-2.8° (c=9.432, pyridine).

$^1$H-NMR: 0.89 (s, 3H, 18-H$_3$), 3.62-3.66 (1H, 16β-H), 3.71 (d, 1H, 17α-H), 6.55-7.32 (Ar—H), 8.33 (s, 1H, CH=N), 13.65 (s, 1H, 3-OH).

$^{13}$C-NMR: 12.2 (C-18), 32.8 (C-15), 36.5 (C-12), 44.0 (C-13), 48.4 (C-14), 74.6 (C-16), 163.9 (CH=N).

17α-Hydroxy-16β-(E)-salicylidene imino)-3-methoxy-estra-1,3,5(10)-triene obtained by conversion of 16β-amino-17α-hydroxy-3-methoxy-estra-1,3,5(10)-triene) and salicylaldehyde in abs. methanol.

$C_{26}H_{31}NO_3$ (405.56), yield: 90.5%, F=198-203° C. (from MeOH).

Calc.: C, 76.99; H, 7.71; N, 3.47. found: C, 77.07; H, 7.89; N, 3.39; $[\alpha]_D$+62.7°.

$^1$H-NMR: 0.96 (s, 3H, 18-$H_3$); 3.66 (t, $^3J$=7.5 Hz, 1H, 16β-H); 3.76 (s, 3H, $OCH_3$); 3.78 (s, 1H, 17β-H); 6.62-7.32 (m, 7H, aromat. H); 8.33 (s, 1H, N=CH);

$^{13}$C-NMR (CDCl$_3$): 17.31 (C-18), 77.71 (C-16), 77.71 (16-C); 86.80 (17-C); 116.88, 118.65, 131.22, 132.19 ($C_6H_4$); 118.72 (C—$\underline{C}_6H_4$); 160.92 (HO—$\underline{C}_6H_4$); 163.55 (N=CH).

IR (KBr): 1628 (s, CH=N).

17α-Hydroxy-16α-[(E)-salicylidene imino)-3-methoxy-estra-1,3,5(10)-triene obtained as tautomeric mixture with according 1,3-oxazolidine C2 epimers by conversion of 16α-amino-17α-hydroxy-3-methoxy-estra-1,3,5(10)-triene) and salicylaldehyde in abs. methanol.

$C_{26}H_{31}NO_3$ (405.56), yield: 72,%, F=128-132° C. Recrystallization from ethanol yields the same isomeric mixture:

$[\alpha]_D$ 103.7° (c=0.875). IR (ATR):1637 (s, CH=N), 3104 (br, NH).

Calc. C, 76.99; H, 7.71; N, 3.47. found: C, 76.57; H, 7.87; N, 3.53.

$^1$H-NMR: 0.72, 078 und 0.84 (3×s, 3×3H, 3×18-$H_3$); 5.38 and 5.98 (2×s, 2×1H, 2×CH—N); 8.43 (s, 1H, CH=N).

(E)-17β-Hydroxy-16β-(2-hydroxy-naphth-1-carbaldimino)-3-methoxy-estra-1,3,5(10)-triene obtained by conversion of 16β-amino-17β-hydroxy-3-methoxy-estra-1,3,5(10)-triene) and 2-hydroxy-naphth-1-carbaldehyde in abs. ethanol.

$C_{30}H_{33}NO_3$ (455.6): calc. C, 79.10; H, 7.30; N, 3.07. found: C, 78.98; H, 7.37; N, 3.13. 63%, F=260-262° C. (from THF/acetonitrile), $[\alpha]_D$+59° (c=0.974, pyridine).

IR (KBr): 1628 cm$^{-1}$ (vs, CH=N), 3183 (m, br., OH ass.).

$^1$H-NMR: 0.97 (s, 3H, 18-$H_3$), 2.85 (m$_c$, 2H, 6-$H_2$), 3.76 (s, 3H, $OCH_3$), 3.71 (d, $^3J$=8.5 Hz, 1H, 17α-H), 4.04 (m$_c$, 1H, 16α-H), 6.62 (d, $^4J$=2.7 Hz, 1H, 4-H), 6.71 (dd, $^3J$=8.5 Hz, $^4J$=2.8 Hz, 1H, 2-H), 6.90 (d, $^4J$=2.7 Hz, 1H, Ar—H), 7.16-7.24 (m, overlay in CDCl$_3$, approx. 2H, 1-H and Ar—H), 7.40 (t, $^3J$=7.1 Hz, 1H, Ar—H), 7.53 (d, $^3J$=7.9 Hz, 1H, Ar—H), 7.62 (d, $^3J$=8.4 Hz, 1H, Ar—H), 7.83 (d, $^3J$=8.4 Hz, 1H, Ar—H), 8.72 (s, 1H, CH=N), 14.46 (s, br., 1H, OH).

(E)-17α-Hydroxy-16α-(2-hydroxy-naphth-1-carbaldimino)-3-methoxy-estra-1,3,5(10)-triene obtained by conversion of 16α-amino-17α-hydroxy-3-methoxy-estra-1,3,5(10)-triene) and 2-Hydroxy-1-naphth-carbaldehyde in abs. ethanol, yield 63%.

$C_{30}H_{33}NO_3$ (455.6): calc. C, 79.10; H, 7.30; N, 3.07. found: C, 77.27; H, 7.43; N, 3.06.—MS (70 eV); m/z (%): 455 (100) [M$^+$].—HR-MS $C_{30}H_{33}NO_3$: calc. 455.2450. found: 455.2461.

63%, F=235.5-237° C. (from methanol or toluene/heptane), $[\alpha]_D$+286° (c=0.981).

$^1$H-NMR (400 MHz, DMSO-D$_6$; HMQC, HMBC, TOCSY, NOE, NOESY): 0.78 (s, 3H, 18-$H_3$), 2.76 (m$_c$, 2H, 6-$H_2$), 3.68 (s, 3H, $OCH_3$), 3.71 (t, $^3J$=5.2 Hz, 1H, 17β-H), 4.24 (m$_c$, 1H, 16β-H), 5.48 (d, $^3J$=5.2 Hz, 1H, 17-OH), 6.60 und 6.61 (2×d, overl., $^3J$=9.5 Hz, $^4J$=3.5 Hz, 2H, Ar—H and 4-H), 6.67 (dd, $^3J$=8.5 Hz, $^4J$=2.7 Hz, 1H, 2-H), 7.12 (t, J=7.1 Hz, 1H, Ar—H), 7.18 (d, $^3J$=8.7 Hz, 1H, 1-H), 7.38 (t, $^3J$=8.3 Hz, 1H, Ar—H), 7.56 (d, $^3J$=7.8 Hz, 1H, Ar—H), 7.64 (d, $^3J$=9.4 Hz, 1H, Ar—H), 7.98 (d, $^3J$=8.4 Hz, 1H, Ar—H), 9.02 (d, $^3J$=12.3 Hz, 1H, CH=N), 13.60 (dd, $^3J$=12.2 Hz, $^4J$=9.0 Hz, 1H, Ar—OH).

IR (KBr): 1629 cm$^{-1}$ (vs, CH=N), 3230 (w-m, br., OH ass.).

3,17β-Dihydroxy-16α-salicylidene imino-estra-1,3,5(10)-triene obtained by conversion of 16α-amino-3,17β-dihydroxy-estra-1,3,5(10)-triene) and salicylaldehyde in abs. methanol.

$C_{25}H_{29}NO_3$ (391.51), F=235-238° C. (from methanol), $[\alpha]_D$-2.80 (c=9.432, pyridine), R$_f$=0.34.

$^1$H-NMR: 0.89 (s, 3H, 18-$H_3$), 3.62-3.66 (1H, 16β-H), 3.71 (d, 1H, 17α-H), 6.55-7.32 (Ar—H), 8.33 (s, 1H, CH=N), 13.65 (s, 1H, 3-OH).

$^{13}$C-NMR: 12.2 (C-18), 32.8 (C-15), 36.5 (C-12), 44.0 (C-13), 48.4 (C-14), 74.6 (C-16), 163.9 (CH=N).

Calc. C, 76.69; H, 7.47; N, 3.58. found: C, 76.36; H, 7.18; N, 3.56.

16α-[(E)-3-Hydroxy-5-hydroxymethyl-pyrid-4-carbaldimino]-17β-hydroxy-3-methoxy-estra-1,3,5(10)-triene obtained by conversion of 16α-amino-17β-hydroxy-3-methoxy-estra-1,3,5(10)-triene) and pyridoxaldehyde-hydrochloride in abs. methanol. Aqueous synthesis under addition of small amounts of potassium carbonate.

$C_{27}H_{34}N_2O_4$ (450.59), calc. C, 71.98; H, 7.61; N, 6.22. found: C, 71.34; H, 7.82; N, 6.17.

MS (FAB): M+HI$^+$=451.2 (100%), F=244-246° C. (decomp., from 70% methanol), Yield 82%, $[\alpha]_D$+14° (c=10.261).

$^1$H-NMR (DMSO-D$_6$): 0.799 (s, 3H, 18-$H_3$), 1.34-2.30 (m, overl., 14H, steroid-C—H), 2.367 (s, 3H, pyridine-$CH_3$), 2.768 (s, broad, 2H, 6-$H_2$), 3.680 (s, 3H, 3-MeO), 4.625 (s, 2H, $CH_2$—OH) 5.130 (s, 1H, 17α-H), 5.350 (s, 1H, 16β-H), 6.602 (s, 1H, 4-H), 6.660 (d, $^3J$=8.6 Hz, 1H, 2-H), 7.160 (d, $^3J$=8.6 Hz, 1H, 1-H), 7.893 (s, 1H, pyridine-H), 8.797 (s, 1H, N=CH).

$^{13}$C-NMR (DMSO-D$_6$): 12.22, 18.60, 25.73, 26.68, 29.19, 32.34, 36.31, 43.42, 43.67, 47.87, 54.83, 47.87, 54.83, 58.33, 73.78, 86.68, 111.46, 113.43, 119.16, 126.08, 131.99, 132.62, 137.35, 148.04, 154.02, 157.03, 161.54.

IR (KBr): 1626 (CH=N), 1500, 1401.

16β-(2-Hydroxy-3,5-di-tert-butylphenyl-carbaldimino)-17α-hydroxy-estra-1,3,5(10)-triene obtained by conversion of 16β-amino-17α-hydroxy-3-methoxy-estra-1,3,5(10)-triene) and 3,5-di-t-butylsalicylaldehyde in abs. methanol.

$C_{34}H_{47}NO_3$ (517.54), yield: 90%, F=185-188° C. (from MeOH or heptane).

Calc.: C, 78.91; H, 9.15; N, 2.71. found: C, 78.62; H, 9.16; N, 2.74; $[\alpha]_D$+45.5°.

$^1$H-NMR: 0.983 (s, 3H, 18-$H_3$); 1.284 (s, 9H, tert-Bu); 1.413 (s, 9H, tert-Bu); 2.836 (m$_c$, 2H, 6-$H_2$); 3.620 (t, $^3J$=8

Hz, 1H, 17β-H); 3.762 (s, 3H, OCH$_3$); 3.807 (s, 1H, 16α-H); 6.618 (s, 1H, 4-H), 6.695 (d, $^3$J=9.4 Hz, 1H, 2-H), 7.066 (s, 1H, Ar—H), 7.222 (d, $^3$J=9.4 Hz, 1H, 1-H), 7.346 (s, 1H, Ar—H), 8.360 (s, 1H, CH=N).

16α-{[2-Hydroxy-4-(4'-phenylcarbonyloxy)phenyl]-carbaldimino}-17β-hydroxy-3-methoxy-estra-1,3,5 (10)-triene obtained by conversion of 16α-amino-17β-hydroxy-3-methoxy-estra-1,3,5(10)-triene) and 2-hydroxy-4-(4'-phenylcarbonyloxy)benzaldehyde in abs. ethanol.

C$_{33}$H$_{35}$NO$_5$ (525.64), yield: 37%, F=219-223° C. (slow decomp., from MeOH/ethyl acetate=3:1), [α]$_D$+84° (c=7.675). MS (FAB): M$^+$=526.8.

$^1$H-NMR: 0.895 (s, 3H, 18-H$_3$), 1.24-2.35 (m, overl., aliph. H), 2.845 (m$_c$, 2H, 6-H$_2$), 3.470 (s, 3H, OCH$_3$), 3.65-3.34 (m, overl., 2H, 16β-H and 17α-H), 6.628 (m$_c$, 1H, 4-H), 6.690 (d, overl., $^3$J=9 Hz, 2H, 2-H and Ar—H), 6.800 (s, 1H, Ar—H), 7.176-7.263 (m, overl. 2H, 2×Ar—H), 7.530 (t, $^3$J=8 Hz, 2H, Ar—H), 7.632 (t, $^3$J=8 Hz, 1H, Ar—H), 8.718 (d, $^3$J=8 Hz, 2H, 2×Ar—H), 8.313 (s, 1H, CH=N).

IR: 3536 (m, OH), 1732 (s, CH=N), 1631 (s), 1611 (s), 1500 (s), 1451 (m), 1257 (vs).

16α-{1-[2-Hydroxy-(4-phenylcarbonyloxy)-phenyl]-eth-1-yleneimino}-17β-hydroxy-3-methoxy-estra-1,3,5(10)-triene obtained by conversion of 16α-amino-17β-hydroxy-3-methoxy-estra-1,3,5(10)-triene) and 2-hydroxy-4-(4'-phenylcarbonyloxy)acetophenone in abs. ethanol, 8 hours reaction time at room temperature.

C$_{34}$H$_{37}$NO$_5$ (539.67), yield: 50%; F=157-161° C., differential thermal analysis: F=173° C., from ethyl acetate/heptane recrystallized; [α]$_D$+132° (c=9.017). MS (FAB): M$^+$=539.3.

$^1$H-NMR (400 MHz): 0.934 (s, 3H, 18-H$_3$), 1.24-2.08 (m, overl., 11H, aliph H), 2.287 (s m, overl., 5H, CH$_3$—C=N and 2×aliph H), 2.840 (m$_c$, 2H, 6-H$_2$), 3.765 (s, 3H, OCH$_3$), 3.857 (d, $^3$J=7 Hz, 1H, 17α-H), 4.190 (d, $^3$J=7 Hz, 1H, 16β-H), 6.099 (s, sher broad, 1H, OH), 6.383 (dd, $^3$J=9 Hz, $^4$J=2 Hz, 2H, 2×Ar—H), 6.646 (s, 2H, 2×Ar—H), 7.089 (d, $^3$J=9 Hz, 1H, Ar—H), 7.275 (t, $^3$J=9 Hz, 1H, Ar—H), 7.502 (t, $^3$J=7 Hz, 2H, 2×Ar—H), 7.630 (t, $^3$J=7 Hz, 1H, Ar—H), 8.159 (d, $^3$J=7 Hz, 1H, Ar—H).

$^{13}$C-NMR (400 MHz): 12.10, 14.12, 13.85, 22.69, 26.14, 27.20, 29.80, 31.88, 32.98, 36.92, 38.43, 44.06, 44.10, 48.64, 55.231, 62.48, 88.40, 109.14, 111.59, 113.55, 113.737, 114.712, 126.528, 128.61, 129.41, 130.17, 130.66, 132.08, 133.68, 137.72, 155.97, 157.48, 164.81, 172.39, 172.97.

16α-{[2-Hydroxy-(4-(4'-n-butoxy-phenyl)carbonyloxy)-phenyl]-carbaldimino}-17β-hydroxy-3-methoxy-estra-1,3,5(10)-triene obtained by conversion of 16α-amino-17β-hydroxy-3-methoxy-estra-1,3,5(10)-triene) and 2-hydroxy-4-[4'-(4"-n-butoxyphenyl)carbonyloxy]benzaldehyde in abs. methanol.

C$_{37}$H$_{43}$NO$_6$ (597.75), yield: 75%, after recrystallization from ethanol/ethyl acetate: 55%, F=195-197° C., [α]$_D$+132° (c=9.017).

$^1$H-NMR (400 MHz, Tocsy, Cosydqf, HMQC, HMBC, Dept90): 0.891 (s, 3H, 18-H$_3$), 0.979 (t, $^3$J=7.2 Hz, 3H, CH$_3$—CH$_2$—), 1.38-1.52 (m, overl., 7H, aliph H), 1.75-1.85 (m, overl., 3H, aliph. H), 1.94-2.01 (m, overl., 2H, aliph. H), 2.298 (m$_c$, 2H, aliph. H), 2.844 (m$_c$, 2H, 6-H$_2$), 3.626 (m$_c$, 1H, 16β-H), 3.709 (d, $^3$J=6.5 Hz, 1H, 17α-H), 3.763 (s, 3H, OCH$_3$), 4.034 (t, $^3$J=6.5 Hz, 2H, —CH$_2$—O), 6.618 (m$_c$, 2H, 4-H and Ar—H), 6.700 (dd, $^3$J=8.3 Hz, $^4$J=2.9 Hz, 1H, 2-H), 6.742 (d, $^4$J=2.8 Hz, 1H, Ar—H), 6.955 (d, $^3$J=7.6 Hz, 2H, 2×Ar—H), 7.183 (dd, $^3$J=8.3 Hz, $^4$J=2.9 Hz, 1H, 1-H), 7.239 (s, 1H, Ar—H), 8.111 (d, $^3$J=7.6 Hz, 2H, 2×Ar—H), 8.257 (s, 1H, CH=N).

$^{13}$C-NMR (400 MHz): 12.23, 13.81, 19.17, 26.02, 27.15, 29.72, 31.10, 32.81, 36.62, 38.43, 43.94, 44.00, 48.42, 55.19, 67.99, 73.74, 87.90, 98.71, 110.87, 111.52, 112.04, 113.78, 114.29, 116.17, 121.26, 126.28, 132.31, 132.72, 137.86, 154.62, 157.46, 163.38, 163.61, 164.57.

IR: 3435 (vs, broad), 1729 (m-s), 1628 (s), 1605 (s), 1501 (m-s).

16β-{[2-Hydroxy-(4-(4'-n-butoxy-phenyl)carbonyloxy)-phenyl]-carbaldimino}-17α-hydroxy-3-methoxy-estra-1,3,5(10)-triene obtained by conversion of 16β-amino-17α-hydroxy-3-methoxy-estra-1,3,5(10)-triene) and 2-hydroxy-4-[4'-(4"-n-butoxyphenyl)carbonyloxy]benzaldehyde in abs. ethanol.

C$_{37}$H$_{43}$NO$_6$ (597.75), yield after recrystallization from ethanol/ethyl acetate: 67%, F 154-157° C., [α]$_D$+31° (c=10.010); again from ethyl acetate/heptane: F=165-168° C., [α]$_D$+30 0 (C=5.006).

EA, calc. C, 74.35; H, 7.25; N, 2.34. found: C, 74.60; H, 7.19; N, 2.27.

$^1$H-NMR: 0.958 (s, 3H, 18-H$_3$), 0.979 (t, $^3$J=7.2 Hz, 3H, CH$_3$—CH$_2$—), 1.427-1.924 (m, overl., 12H, aliph H), 2.346 (m$_c$, 3H, aliph. H), 2.854 (m, 2H, 6-H$_2$), 3.666 (t, $^3$J=7.4 Hz, 1H, 16α-H), 3.763 (s, overl., 4H, 1713 and OCH$_3$), 4.034 (t, $^3$J=6.5 Hz, 2H, —CH$_2$—O), 6.618 (m$_c$, 1H, 4-H), 6.686-6.779 (m, overl., 3H, 3×Ar—H), 6.948 (d, $^3$J=8.8 Hz, 2H, 2×Ar—H), 7.149-7.265 (m, overl., 2H, 2×Ar—H), 8.113 (d, $^3$J=8.8 Hz, 2H, 2×Ar—H), 8.315 (s, 1H, CH=N), 13.766 (s, 1H, OH).

$^{13}$C-NMR (DEPT 135, DEPT 90): 13.79, 17.36, 19.18, 25.92, 28.02, 29.80, 31.12, 31.86, 34.93, 38.68, 43.42, 45.37, 48.54, 55.21, 68.2, 86.86, 110.46, 111.56, 112.55, 113.81, 114.32, 116.55, 121.28, 126.30, 132.12, 132.34, 132.38, 137.88, 154.23, 157.52, 162.76, 162.95, 163.66, 164.47.

IR: 3440 (vs, broad), 1731 (m), 1628 (s), 1606 (s), 1510 (m), 1501 (m).

16β-{[2-Hydroxy-(4-(4'-n-butoxy-phenyl)carbonyloxy)-phenyl]-carbaldimino}-17β-hydroxy-3-methoxy-estra-1,3,5(10)-triene obtained by conversion of 16β-amino-17β-hydroxy-3-methoxy-estra-1,3,5(10)-triene) and 2-hydroxy-4-[4'-(4"-n-butoxyphenyl)carbonyloxy]benzaldehyde in abs. ethanol.

C$_{37}$H$_{43}$NO$_6$ (597.75), yield after recrystallization from THF/isopropanol/ethyl acetate (1:2:2): 95%, F 229-232° C., [α]$_D$+18° (c=8.376); again 2× from methanol/THF: F=230-233.5° C. MS (FAB): M$^+$=597.5.

$^1$H-NMR: 0.949 (s, 3H, 18-H$_3$), 0.989 (t, $^3$J=7 Hz, 3H, CH$_3$—CH$_2$—), 1.24-1.57 (m, overl., 8H, aliph H), 1.76-1.85 (m, overl., 3H, aliph H), 2.027 (m$_c$, 1H, aliph. H), 2.362 (m$_c$, overl., 3H, aliph. H), 2.298 (m$_c$, 3H, aliph. H), 2.847 (m$_c$, 2H, 6-H$_2$), 3.727 and 3.899 (each: m$_c$, 1H, 16-α und 17α-H), 3.763 (s, 3H, OCH$_3$), 4.032 (m$_c$, 2H, —CH$_2$—O), 6.62-6.78 (m, 4H, 4-H und 3×Ar—H), 6.941 (d, $^3$J=9 Hz, 2H, 2×Ar—H), 6.213 (d, $^3$J=9 Hz, 1H, Ar—H), 7.283 (d, $^3$J=9 Hz, 1H, Ar—H), 8.109 (d, $^3$J=9 Hz, 2H, 2×Ar—H), 8.300 (s, 1H, CH=N), 13.045 (s, 1H, OH).

$^{13}$C-NMR (DEPT 135, DEPT 90): 12.10, 13.79, 19.17, 26.15, 27.34, 29.72, 31.11, 34.48, 37.16, 38.34, 43.47, 44.14, 47.92, 55.20, 67.99, 68.02, 68.75, 82.88, 110.51, 111.57, 112.78, 113.84, 114.33, 116.46, 121.25, 126.33, 132.34, 132.53, 137.78, 154.51, 157.54, 162.72, 163.67, 164.34, 165.62.

IR: 3445 (vs, broad), 1728 (m-s), 1628 (s), 1605 (s), 1501 (m-s).

General Protocol for the Reduction of Schiff Bases Using NaBH$_4$ to the Arylmethylamines of this Invention According to Scheme 1

To 1 mmol steroidal Schiff base synthesized according to examples as outlined above in 10 ml abs. methanol, 2 equivalents of NaBH$_4$ are added under argon atmosphere at room temperature. After 5-10 min, a clear, colorless liquid is formed in most cases. Depending on the reactivity, stirring is continued 20 to 100 min at room temperature, then H$_2$O and a few drops of acetic acid is added. The resulting precipitate is collected by filtration, washed several times with H$_2$O and recrystallized from methanol or ethanol, if required under addition of a small amount of water. Poorly soluble steroid amines are advantageously recrystallized under addition of THF.

In the same manner obtained is for example:

17β-(2-Hydroxyphenyl-methylamino)-3-methoxy-estra-1,3,5(10)-triene (1)

obtained by conversion of 17β-[(E)-salicylidenimino]-3-methoxy-estra-1,3,5(10)-triene and NaBH$_4$.

C$_{26}$H$_{33}$NO$_2$ (391.55), F=117.5-119.5° C. (from methylene chloride/hexane), R$_f$=0.29.

$^1$H-NMR: 0.789 (s, 3H, 18-H$_3$), 1.170-2.332 (m, overl., approx. 13H, 13× aliph. H), 2.720 (t, $^3$J=8.4 Hz, 1H, 17α-H), 2.847 (s, broad, 2H, 6-H$_2$), 3.780 (s, 3H, 3-MeO), 3.959 (d, $^2$J=15.1 Hz, 1H, benzyl-H), 4.106 (d, $^2$J=15.1 Hz, 1H, benzyl-H), 6.627 (m, 1H, 4-H), 6.694-6.861 (m, overl. 3H, 1-H and 2×Ar—H), 7.001 (d, $^3$J=7.5 Hz, 1H, Ar—H), 7.184 (m, 2H, 2×Ar—H).

$^{13}$C-NMR: 11.86, 23.46, 26.29, 27.38, 28.84, 29.76, 37.56, 38.72, 42.92, 43.96, 51.68, 52.02, 55.19, 67.78, 111.46, 113.82, 116.43, 118.90, 122.94, 126.28, 128.10, 128.68, 132.53, 137.89, 157.47, 158.47.

17α-(2-Hydroxyphenyl-methylamino)-3-methoxy-estra-1,3,5(10)-triene (2)

obtained by conversion of 17α-[(E)-salicylidene imino]-3-methoxy-estra-1,3,5(10)-triene and NaBH$_4$.

C$_{26}$H$_{33}$NO$_2$ (391.55), F=145.5-147.5° C. (from methanol), R$_f$=0.71, [α]$_D$+7.1° (C=10.508).

$^1$H-NMR (300 MHz): 0.914 (s, 3H, 18-H$_3$), 1.458-2.364 (m, overl., 13H, aliph. H), 2.788 (d, $^3$J=6.6 Hz, 1H, 17β-H), 2.868 (m, broad, 2H, 6-H$_2$), 3.789 (s, 3H, 3-MeO), 3.826 (d, $^2$J=13.8 Hz, 1H, NH—CH$_2$-phenyl), 4.062 (d, $^2$J=13.8 Hz, 1H, NH—CH$_2$-Phenyl), 6.645 (s, 1H, 4-H), 6.726 (d, $^3$J=8.4 Hz, 1H, 2-H), 6.760-6.866 (m, overl., 2H, Ar—H), 7.014 (d, $^3$J=8.3 Hz, 1H, 1-H), 7.158-7.205 (m, overl. 2H, Ar—H).

$^{13}$C-NMR (75 MHz): 19.08, 24.82, 26.31, 28.08, 29.05, 29.89, 32.83, 39.24, 43.56, 44.95, 49.59, 51.06, 55.20, 66.70, 111.49, 113.80, 116.42, 118.94, 122.96, 126.36, 128.13, 128.70, 132.51, 137.92, 157.47, 158.34.

IR: 1613 (m), 1586 (m) and 1495 (m; arom. C=C), no signal at 1630 (for CH=N).

16β-(2-Hydroxyphenyl-methylamino)-3-methoxy-estra-1,3,5(10)-triene (3)

obtained by conversion of 6β-[(E)-salicylidene imino]-3-methoxy-estra-1,3,5(10)-triene and NaBH$_4$.

C$_{26}$H$_{33}$NO$_2$ (391.55), F=149-151.5° C. (from methanol), yield 88%, R$_f$=0.43, [α]$_D$+61.7° (c=7.315).

$^1$H-NMR: 0.92 (s, 3H, 18-H$_3$), 3.29 (m, 1H, 16α-H), 3.93 (q, 2H, N—CH$_2$), 3.76 (s, 3H, OCH$_3$), 6.61-7.19 (7H, Ar—H).

$^{13}$C-NMR: 19.9 (C-18), 26.4 (C-11), 28.0 (C-7), 29.8 (C-6), 34.2 (C-15), 38.9 (C-12), 38.4 (C-8), 40.5 (C-13), 43.8 (C-9), 47.6 (C-17), 52.7 (C-14), 55.2 (OCH$_3$), 56.4 (C-16), 111.5 (C-2), 113.7 (C-4), 126.2 (C-1), 132.6 (C-10), 137.8 (C-5), 157.4 (C-3); 51.6 (CH$_2$—N); Ar—C: 116.4, 119.0, 122.7 (q), 128.2, 128.7, 158.2 (q).

Calc. C, 79.75; H, 8.49; N, 3.58. found: 78.70, 8.37, 3.95.
HRMS: calc. 391.25113. found: 391.25171.
IR: 1472, 1499, 1608, 3687.

16α-(2-Hydroxyphenyl-methylamino)-3-methoxy-estra-1,3,5(10)-triene (4)

obtained by conversion of 16α-[(E)-salicylidene imino]-3-methoxy-estra-1,3,5(10)-triene and NaBH$_4$.

C$_{26}$H$_{33}$NO$_2$ (391.55), 148-149.5° C. (from methanol), yield 87%, R$_f$=0.30, [c]$_D$+54.8° (c=6.780).

$^1$H-NMR: 0.75 (s, 3H, 18-H$_3$), 3.38 (m, 1H, 16β-H), 3.39 (q, 2H, N—CH$_2$), 3.76 (s, 3H, OCH$_3$), 6.61-7.20 (7H, Ar—H).

$^{13}$C-NMR: 18.3 (C-18), 26.3 (C-11), 28.0 (C-7), 29.6 (C-6), 33.0 (C-15), 38.6 (C-12), 38.7 (C-8), 41.6 (C-13), 43.9 (C-9), 49.5 (C-17), 51.7 (C-14), 55.2 (OCH$_3$), 55.8 (C-16), 111.4 (C-2), 113.8 (C-4), 126.2 (C-1), 132.7 (C-10), 137.9 (C-5), 157.4 (C-3); 51.7 (CH$_2$—N); Ar—C: 116.4, 118.9, 122.8 (q), 128.1, 128.6, 154.4 (q).

Calc. C, 79.75; H, 8.49; N, 3.58. found: 79.59, 8.44, 3.59.
HRMS: calc. 391.25113. found: 391.25390.

17α-(2-Methoxyphenyl-methylamino)-3-methoxy-estra-1,3,5(10)-triene (5)

obtained by conversion of 17α-[(E)-2-methoxyphenyl-carbaldimino]-3-methoxy-estra-1,3,5(10)-triene and NaBH$_4$.

C$_{27}$H$_{35}$NO$_2$ (405.58), F=71-72° C. (from hexane or MeOH), R$_f$=0.42.

$^1$H-NMR (400 MHz): 0.747 (s, 3H, 18-H$_3$), 1.270-2.348 (m, overl, approx. 13H, aliphatic H), 2.702 (d, overl., $^3$J=6.7 Hz, 1H, 17β-H), 2.847 (s, broad, 2H, 6-H$_2$), 3.705 (d, $^2$J=13.6 Hz, 1H, N-benzyl-H), 3.789 (s, 3H, 3-MeO), approx. 3.800 (d, overl., $^2$J=13.6 Hz, 1H, N-benzyl-H), 3.870 (s, 3H, 2-MeO-benzyl), 6.638 (s, 1H, 4-H), 6.712 (d, $^3$J=8.6 Hz, 1H, 2-H), 6.876-6.934 (m, overl., 1-H and phenyl-H), 7.219-7276 (m, overl. 3H, 3× phenyl-H).

$^{13}$C-NMR (100 MHz): 19.02, 25.04, 26.48, 28.06, 29.97, 30.10, 32.69, 39.34, 43.46, 43.68, 45.05, 48.23, 48.79, 55.20, 55.25, 66.37, 110.31, 111.43, 113.80, 120.45, 126.27, 128.01, 129.82, 133.07, 138.14, 157.42, 157.77.

17α-(3-Hydroxyphenylmethylamino)-3-methoxy-estra-1,3,5(10)-triene (6)

obtained by conversion of 17α-[(E)-3-hydroxyphenyl-carbaldimino]-3-methoxy-estra-1,3,5(10)-triene and NaBH$_4$.

C$_{26}$H$_{33}$NO$_2$ (391.55), F=128-129° C. (raw product), R$_f$=0.19 (uniform).

$^1$H-NMR (in DMSO-D$_6$): 0.668 (s, 3H, 18-H$_3$), 1.000-2.400 (m, overl, approx. 13H, aliph. H), 2.587 (d, $^3$J=6.7 Hz, 1H, 17β-H), 2.771 (s, broad, 2H, 6-H$_2$), 3.513 (d, $^2$J=13.8 Hz, 1H, N-benzyl-H), 3.634 (d, overl., $^2$J=13.8 Hz, 1H, N-benzyl-H), 3.673 (s, overl., 3H, 3-MeO), 6.590 (s, 1H, 4-H), 6.630-

6.748 (m, overl., 3H, 2-H and 2×Ar—H), 7.059 (t, $^3J$=7.8 Hz, 1H, Ar—H), 7.164 (d, $^3J$=8.5 Hz, 1H, 1-H), 9.214 (s, 1H, X—H).

$^{13}$C-NMR (in DMSO-D$_6$): 19.93, 24.87, 26.61, 28.24, 29.85, 30.07, 32.92, 43.69, 45.32, 48.61, 52.57, 55.31, 66.59, 111.91, 113.76, 113.86, 115.15, 118.88, 126.64, 129.38, 132.73, 137.89, 143.37, 157.46, 157.66.

17α-(4-Hydroxyphenyl-methylamino)-3-methoxy-estra-1,3,5(10)-triene (7)

obtained by conversion of 17α-[(E)-4-Hydroxyphenyl-carbaldimino]-3-methoxy-estra-1,3,5(10)-triene and NaBH$_4$.

C$_{26}$H$_{33}$NO$_2$ (391.55), F=143-145° C. (from EtOH, 90%), R$_f$=0.19.

$^1$H-NMR: 0.759 (s, 3H, 18-H$_3$), 1.284-2.000 (m, overl, approx. 13H, aliph. H), 2.772 (d, overl., 3J=6.8 Hz, 1H, 17β-H), 2.843 (s, broad, 2H, 6-H$_2$), 3.593 (d, $^2J$=12.8 Hz, 1H, N-benzyl-H), approx. 3.740 (d, overl., $^2J$=12.8 Hz, 1H, N-benzyl-H), 3.778 (s, 3H, 3-MeO), 6.634-6.722 (s and d, overl., $^3J$=8.4 Hz, 4H, 4-H, 2-H and 2× phenyl-H), 7.128-7.263 (d and m, overl., $^3J$=8.4 Hz, 1-H and 2× phenyl-H).

$^{13}$C-NMR: 19.12, 25.04, 26.43, 28.03, 29.93, 30.08, 32.86, 39.24, 43.42, 45.06, 48.92, 52.30, 55.20, 67.03, 111.42, 113.76, 115.11, 115.53, 126.30, 129.49, 132.16, 132.92, 138.09, 155.01, 157.37.

17α-[(2-Hydroxynaphth-1-yl)-methylamino]-3-methoxy-estra-1,3,5(10)-triene (17)

obtained by conversion of 17α-[(E)-2-hydroxynaphth-1-carbaldimino]-3-methoxy-estra-1,3,5(10)-triene and NaBH$_4$.

C$_{30}$H$_{35}$NO$_2$ (441.61), MS: M+HI$^+$=442.4 (100%), F=105-106° C. (from EtOH, addition of 10% H$_2$O), R$_f$=0.58.

$^1$H-NMR (selected data): 0.858 (s, 3H, 18-H$_3$), 2.875 (m, broad, 2H, 6-H$_2$), 3.796 (s, 3H, 3-MeO), 4.373 (d, $^2J$=9.3 Hz, 2H, benzyl-H), 4.483 (d, $^2J$=9.3 Hz, 2H, benzyl-H), 6.654 (s, 1H, 4-H), 6.736 (d, $^3J$=4.7 Hz, 1H, 2-H), 7.172 (d, $^3J$=4.7 Hz, 1H, 1-H), 7.200-7.480 (m, overl., approx. 6H, naphthyl-H).

17β-[(3-Hydroxynaphth-2-yl)-methylamino]-3-methoxy-estra-1,3,5(10)-triene (18)

obtained by conversion of 17β-[(E)-3-hydroxynaphth-2-carbaldimino]-3-methoxy-estra-1,3,5(10)-triene (25) and NaBH$_4$.

C$_{30}$H$_{35}$NO$_2$ (441.61), MS: M+HI$^+$=442.4 (100%), F=192-194° C. (from EtOH/THF, 1:1, addition of 10% H$_2$O), R$_f$=0.40.

$^1$H-NMR: 0.814 (s, 3H, 18-H$_3$), 1.293-2.291 (m, overl., approx. 13H, aliph. H), 2.706 (t, $^3J$=8.6 Hz, 1H, 17α-H), 2.850 (s, broad, 2H, 6-H$_2$), 3.784 (s, 3H, 3-MeO), 4.130 (d, $^2J$=13.7 Hz, 1H, benzyl-H), 4.273 (d, $^2J$=13.7 Hz, 1H, benzyl-H), 6.639 (s, broad, 1H, 4-H), 6.717 (d, $^3J$=8.2 Hz, 1H, 2-H), 7.204-7.308 (m, overl. 3H, 1-H and 2× naphthyl-H), 7.390 (t, $^3J$=7.8 Hz, 1H, naphthyl-H), 7.508 (s, 1H, naphthyl-H), 7.692 (d, $^3J$=8.1 Hz, 2H, 2× naphthyl-H).

$^{13}$C-NMR: 11.88, 23.46, 26.29, 27.37, 28.82, 29.76, 37.50, 38.71, 42.92, 43.94, 51.96, 51.99, 55.20, 67.69, 110.61, 111.46, 113.82, 123.03, 125.76, 125.93, 126.19, 126.29, 127.16, 127.26, 127.98, 132.51, 134.52, 137.89, 156.50, 157.47.

17β-[(2-Hydroxynaphth-1-yl)-methylamino]-3-methoxy-estra-1,3,5(10)-triene hydroperchlorate (19)

obtained by conversion of 17β-[(E)-2-hydroxynaphth-1-carbaldimino]-3-methoxy-estra-1,3,5(10)-triene and NaBH$_4$. The raw product is chromatographed to silica gel (eluent ethyl acetate/hexane, gradient 1:7 to 1:4). The resulting oil is dissolved in THF, followed by addition of 2 equivalents of perchloric acid and precipitation of the resulting product at 4° C. with water.

C$_{30}$H$_{36}$NO$_6$Cl (542.07), MS: 442.4 (M$^+$-ClO$_4$), F=138-143° C. (glassy, decomp.), R$_f$=0.50.

$^1$H-NMR (broad signals, selected data): 0.896 (s, 3H, 18-H$_3$), 2.770 (s, broad, 2H, 6-H$_2$), 3.752 (s, 3H, 3-MeO), 4.716 (m, 2H, CH$_2$—N), 8.455 (s, broad, 1H, X—H).

$^{13}$C-NMR: 11.51, 23.21, 25.15, 25.76, 27.08, 29.45, 35.97, 38.16, 38.45, 42.73, 43.29, 43.74, 51.25, 55.19, 66.89, 107.72, 111.54, 113.82, 117.64, 121.26, 123.83, 126.24, 127.98, 129.07, 131.64, 132.03, 132.44, 137.52, 153.71, 157.54.

17β-(3-Hydroxyphenyl-methylamino)-3-methoxy-estra-1,3,5(10)-triene (20)

obtained by conversion of 17β-[(E)-3-hydroxyphenyl-carbaldimino]-3-methoxy-estra-1,3,5(10)-triene and NaBH$_4$.

C$_{26}$H$_{33}$NO$_2$ (391.55), MS: M+HI$^+$=392.3 (100%), 184-187 (from EtOH/THF, 4:1), R$_f$≈0.

$^1$H-NMR (broad signals): 0.795 (s, 3H, 18-H$_3$), 1.100-2.350 (m, overl., approx. 13H, aliph. H), 2.704 (t, $^3J$ approx. 7 Hz, 1H, 17α-H), 2.482 (s, very broad, approx. 4H, 6-H$_2$ and 2×N-benzyl-H), 3.779 (s, 3H, 3-MeO), 6.663 (s, 1H, 4-H), 6.700 (s, broad, overl., 2H, 2-H and phenyl-H), 6.799-6.869 (m, overl., 2H, 2×Ar—H), 7.181 (m, overl., 2×Ar—H).

$^{13}$C-NMR: 11.92, 23.50, 26.50, 27.42, 29.54, 29.82, 38.12, 38.79, 43.17, 43.99, 52.28, 52.44, 55.19, 68.30, 111.43, 113.79, 114.05, 115.17, 120.17, 126.27, 129.50, 132.76, 137.99, 142.43, 155.96, 157.40.

3β-Hydroxy-2α-(2-hydroxyphenyl-methylamino)-cholane (21)

obtained by conversion of 3β-hydroxy-2α-[(E)-salicylidene imino]-cholane and NaBH$_4$.

C$_{34}$H$_{55}$NO$_2$ (509.81), clearing point 167-168° C. (from methanol), R$_f$=0.60.

$^1$H-NMR (selected data): 0.665 (s, 3H, 18-H$_3$), 2.633 (m, 1H), 3.432 (m, 1H), 3.958 (d, $^2J$=13.0 Hz, 1H, benzyl-H), 4.100 (d, $^2J$=13.0 Hz, 1H, benzyl-H), 6.780-7.165 (m, 4H, phenyl-H).

$^{13}$C-NMR: 11.50, 13.20, 18.68, 21.32, 22.53, 22.77, 23.83, 24.19, 27.99, 28.10, 28.20, 31.89, 35.02, 35.77, 36.18, 36.73, 37.31, 39.53, 39.89, 42.59, 44.72, 50.30, 54.26, 56.27, 56.37, 59.64, 116.48, 119.03, 123.55, 127.94, 128.61, 158.10.

2β,3β-Dihydroxy-1α-(2-hydroxyphenyl-methylamino)-cholane (22)

obtained by conversion of 2β,3β-dihydroxy-1α[(E)-salicylidene imino]-cholane and NaBH$_4$.

C$_{34}$H$_{55}$NO$_3$ (525.81), M+HI$^+$=526.4 (100%), clearing point 162-164° C., R$_f$=0.16.

$^1$H-NMR: 0.670 (s, 3H, 18-H$_3$), 2.861 (s, broad, 1H), 3.863 (d, $^2J$=13.4 Hz, 1H, benzyl-H), 3.900 (m, overl., 1H), 4.086 (d, $^2J$=13.4 Hz, 1H, benzyl-H), 4.221 (s, broad, 1H), 6.774-7.194 (m, 4H, phenyl-H).

$^{13}$C-NMR: 12.11, 14.40, 18.73, 21.10, 22.54, 22.79, 23.79, 24.20, 27.99, 28.15, 28.43, 31.41, 32.55, 34.86, 35.77, 36.12, 39.10, 39.24, 39.46, 39.49, 42.58, 48.81, 52.68, 56.05, 56.23, 64.48, 68.81, 70.77, 116.41, 119.34, 122.95, 128.33, 129.10, 157.67.

17β-[4-(N,N-Diethylamino)-2-hydroxyphenyl-methylamino]-3-methoxy-estra-1,3,5(10)-triene (23)

obtained by conversion of 17β-[(E)-[4-(N,N-diethylamino)-2-hydroxyphenyl-carbaldimino]-3-methoxy-estra-1,3,5(10)-triene (24) and NaBH$_4$ in EtOH/THF (2:1).

$C_{30}H_{42}N_2O_2$ (462.67); MS: M+HI$^+$=463.3 (11%), 461.3 (59%), 286.2 (44%), 178.1 (100%); F=137-142° C. (raw product), R$_f$=0.30.

$^1$H-NMR (very broad signals): 0.773 (s, 3H, 18-H$_3$), 1.157 (s, overl., 6H, 2×CH$_3$), 2.851 (s, broad, 2H, 6-H$_2$), 3.310 (s, 4H, 2×CH$_2$N), 3.783 (s, 3H, 3-MeO).

$^{13}$C-NMR: 11.20, 12.10, 23.49, 28.86, 29.78, 30.31, 31.17, 37.57, 38.73, 42.89, 44.37, 44.47, 51.05, 52.21, 55.19, 67.54, 99.37, 102.73, 110.18, 111.44, 113.80, 126.30, 128.69, 132.74, 138.02, 148.78, 157.44, 159.37.

17α-(5-Chloro-2-hydroxyphenyl-methylamino)-3-methoxy-estra-1,3,5(10)-triene (26)

obtained by conversion of 17α-[(E)-5-chloro salicylidene imino]-3-methoxy-estra-1,3,5(10)-triene and NaBH$_4$. Purification of the raw product by column chromatography (silica gel, ethyl acetate/hexane, gradient 1:8 to 1:2).

$C_{26}H_{32}NO_2Cl$ (425.99), MS: M+HI$^+$=426.2 (100%), oil, R$_f$=0.61.

17β-(5-chloro-2-hydroxyphenyl-methylamino)-3-methoxy-estra-1,3,5(10)-triene (27)

obtained by conversion of 17β-[(E)-5-chloro salicylidene imino]-3-methoxy-estra-1,3,5(10)-triene and NaBH$_4$.

$C_{26}H_{32}NO_2Cl$ (425.99), MS: M+HI$^+$=426.2 (100%), F=161-163 (from EtOH), R$_f$=0.69.

17β-(2-Hydroxy-5-nitrophenyl-methylamino)-3-methoxy-estra-1,3,5(10)-triene (28)

obtained by conversion of 17β-[(E)-5-nitrosalicylidene imino]-3-methoxy-estra-1,3,5(10)-triene and NaBH$_4$.

$C_{26}H_{32}N_2O_4$ (436.55), F=212-215° C. (from EtOH/THF 1:1), R$_f$=0.14.

17β-(5-Bromo-2-hydroxyphenyl-methylamino)-3-methoxy-estra-1,3,5(10)-triene (29)

obtained by conversion of 17β-[(E)-5-bromo salicylidene imino]-3-methoxy-estra-1,3,5(10)-triene and NaBH$_4$.

$C_{26}H_{32}NO_2Br$ (470.44), F=164-166° C. (from EtOH, addition of 20% water), R$_f$=0.62.

$^1$H-NMR: 0.798 (s, 3H, 18-H$_3$), 1.115-2.25 (m, overl., steroid C—H), 2.733 (t, $^3$J=8.5 Hz, 1H, 17α-H), 2.862 (s, 2H, 6-H$_2$), 3.775 (s, 3H, OCH$_3$), 3.941 (d, $^2$J=14.0 Hz, 1H, benzyl-H), 4.112 (d, $^2$J=14 Hz, 1H, benzyl-H), 6.631 (s, 1H, 4-H), 6.715 (d, $^3$J=8.7 Hz, 1H, 2-H), 6.828-7.287 (m, approx. 4H, Ar—H).

17β-(2,5-Dihydroxyphenyl-methylamino)-3-methoxy-estra-1,3,5(10)-triene (30)

obtained by conversion of 17β-[(E)-5-hydroxysalicylidene imino]-3-methoxy-estra-1,3,5(10)-triene and NaBH$_4$.

$C_{26}H_{33}NO_3$ (407.55), F=220-226° C. (decomp. above 213° C., from EtOH, subsequent addition of water), R$_f$=0.14.

$^1$H-NMR (selected data): 0.792 (s, 18-H$_3$), 1.10-2.40 (m, overl., steroid C—H), 2.857 (s, 2H, 6-H$_2$), 3.773 (s, 3H, OCH$_3$), 3.920 (d, $^2$J=14.0 Hz, 1H, benzyl-H), 4.110 (d, $^2$J=14 Hz, 1H, benzyl-H), 6.586-7.201 (m, approx. 6H, Ar—H).

17β-(2,3,4-Trihydroxyphenyl-methylamino)-3-methoxy-estra-1,3,5(10)-triene (31)

obtained by conversion of 17β-[(E)-2,3,4-trihydroxyphenyl-carbaldimino]-3-methoxy-estra-1,3,5(10)-triene and NaBH$_4$.

$C_{26}H_{33}NO_4$ (423.55), MS: 424.3 (56%), 285 (100%), F>330° C. (decomp. above approx. 200° C.; raw product), R$_f$=0.

$^1$H-NMR (DMSO): 0.750 (s, 3H, 18-H$_3$), 1.0-2.2 (steroid-C—H), 2.500 (s, 1H, 17α-H), 2.756 (s, broad, 2H, 6-H$_2$), approx. 3.54 (very broad, X—H), 3.673 (s, 3H, 3-MeO), 6.043-7.165 (m, 5H, Ar—H), 8.474 (s, very broad, X—H).

16α-[(3-Hydroxy-naphth-2-yl)-methylamino]-17β-hydroxy-3-methoxy-estra-1,3,5(10)-triene (32)

obtained by conversion of 16α-[(E)-3-hydroxy-naphth-2-carbaldimino]-3-methoxy-estra-1,3,5(10)-triene and NaBH$_4$.

$C_{30}H_{35}NO_3$ (457.61), F=218-222° C. (decomp., from ethanol), R$_f$=0.09.

16α-(2,3-Dihydroxyphenyl-methylamino)-17β-hydroxy-3-methoxy-estra-1,3,5(10)-triene (33)

obtained by conversion of 16α-[(E)-3-hydroxy-salicylidene imino]-17β-hydroxy-3-methoxy-estra-1,3,5(10)-triene and NaBH$_4$.

$C_{26}H_{33}NO_4$ (423.55), F>250° C., decomp. (from ethanol/water, 4:1), R$_f$=0.

$^1$H-NMR: 0.821 (s, 3H, 18-H$_3$), 1.26-2.00 (steroid-C—H), 2.879 (s, broad, 2H, 6-H$_2$), 3.792 (s, 3H, 3-MeO), 6.690 (m, 2H, 2×Ar—H), 7.221-7.801 (m, approx. 7H, 7×Ar—H).

16α-(5-Chloro-2-hydroxyphenyl-methylamino)-17β-hydroxy-3-methoxy-estra-1,3,5(10)-triene (34)

obtained by conversion of 16α-[(E)-5-chloro-salicylidene imino]-17β-hydroxy-3-methoxy-estra-1,3,5(10)-triene and NaBH$_4$.

$C_{26}H_{32}NO_3Cl$ (441.99), F=153.5-154° C. (from ethanol/water), R$_f$=0.14.

16α-[(3-Hydroxy-naphth-2-yl)-methylamino]-17α-hydroxy-3-methoxy-estra-1,3,5(10)-triene (36)

obtained by conversion of 16α-[(E)-3-hydroxy-naphth-2-carbaldimine]-17α-hydroxy-3-methoxy-estra-1,3,5(10)-triene and NaBH$_4$.

$C_{30}H_{35}NO_3$ (457.61), F>200° C. (decomp., from ethanol/THF), R$_f$=0.

$^1$H-NMR: 0.477 (s, 3H, 18-H$_3$), 1.2-2.5 (m, overl., steroid C—H), 2.718 (m, 2H, 6-H$_2$), 3.732 (s, 3H, OCH$_3$), 6.531-7.766 (Ar—H).

16α-(5-chloro-2-hydroxyphenyl-methylamino)-17α-hydroxy-3-methoxy-estra-1,3,5(10)-triene (37)

obtained by conversion of 16α-[(E)-5-chloro-salicylidene imino]-17α-hydroxy-3-methoxy-estra-1,3,5(10)-triene and NaBH$_4$.

$C_{26}H_{32}NO_3Cl$ (441.99), MS: M+HI⁺=442.2; F=250-255 (decomp., form ethanol/water), $R_f$=0.

2α-(2-Hydroxyphenyl-methylamino)-3α-hydroxy-cholane (38)

obtained by conversion of 2α-[(E)-salicylidene imino]-3α-hydroxy-cholane and NaBH₄.

$C_{34}H_{55}NO_2$ (509.81), clearing point: 285-290° C. (from ethanol/water; then AcOEt/hexane), $R_f$=0.22.

¹H-NMR: 0.537 (s, 3H, 18-H₃), 0.620 (s, 3H, 19-H₃); 0.742, 0.7967 and 0.803: overl., 21-, 26- and 27-H₃), 0.7-2.0 (m, overl., aliph. H), 2.478 (s, 1H, 2β-H), 3.010 (s, 1H, 3β-H), 4.057 and 4.138 (each: s, broad, 1H; CH₂—N), 6.737 (t, ³J=8 Hz, 1H, Ar—H), 6.924 (d, ³J=8 Hz, 1H, Ar—H), 7.108 (t, ³J=8 Hz, 1H, Ar—H), 7.256 (d, ³J=8 Hz, 1H, Ar—H), 8.366 (s, broad, 1H, OH), 8.495 (s, broad, 1H, OH).

¹³C-NMR: 17.01, 17.08, 20.44, 27.08, 28.40, 28.82, 32.33, 32.61, 32.86, 36.41, 39.63, 39.70, 39.95, 40.37, 40.78, 41.31, 42.86, 44.84, 47.21, 48.99, 58.60, 60.80, 60.97, 61.49, 62.55, 68.21, 120.76, 122.59, 124.40, 135.44, 136.30, 160.95.

2α-[(3-Hydroxy-naphth-2-yl)-methylamino]-3(-hydroxy-cholane (39)

obtained by conversion of 2α-[(E)-3-hydroxy-naphth-2-carbaldimino]-3β-hydroxy-cholane and NaBH₄.

$C_{38}H_{57}NO_2$ (559.87), clearing point: 189-191° C. (from ethanol/THF=4:1), $R_f$=0.07.

¹H-NMR (very broad signals): 0.5-2.3 (m, overl., aliph. H), 2.86 (s, broad, 1H, 2β-H), 3.60 (s, broad, 1H, 3α-H), 4.10 and 4.42 (each: s, broad, 1H; CH₂—N), 7.29-7.80 (m, overl., 6H, Ar—H), 9.54 (s, broad, OH).

3α-[(3-Hydroxy-naphth-2-yl)-methylamino]-cholane (40)

obtained by conversion of 3α-[(E)-3-hydroxy-naphth-2-carbaldimino]-cholane and NaBH₄.

$C_{38}H_{57}NO$ (543.87), clearing point: 186.5-189° C. (from ethanol/THF=6:1), $R_f$=0.74.

¹H-NMR: 0.549 (s, 3H, 18-H₃), 0.691 (s, 3H, 19-H₃); 0.857, 0.879 and 0.900: overl., 21-, 26- and 27-H₃), 0.9-2.0 (m, overl., aliph. H), 3.172 (s, 1H, 3β-H), 4.337 (m, 2H, CH₂—H), 7.300-7.713 (m, overl., 6H, Ar—H).

17α-[(3-Hydroxy-naphth-2-yl)-methylamino]-3-methoxy-estra-1,3,5(10)-triene (41)

obtained by conversion of 17α-[(E)-3-hydroxy-naphth-2-carbaldimino]-3-methoxy-estra-1,3,5(10)-triene and NaBH₄.

$C_{30}H_{35}NO_2$ (441.61), yield: 90%. F=196-198° C. (from EtOH/THF=1:1, then addition of 10% water), $R_f$=0.60.

¹H-NMR: 0.814 (s, 3H, 18-H₃), 1.293-2.291 (m, overl., approx. 13H, aliph. H), 2.706 (t, ³J=8.6 Hz, 1H, 17α-H), 2.850 (s, broad, 2H, 6-H₂), 3.784 (s, 3H, 3-MeO), 4.130 (d, ²J=13.7 Hz, 1H, Benzyl-H), 4.273 (d, ²J=13.7 Hz, 1H, benzyl-H), 6.639 (s, broad, 1H, 4-H), 6.717 (d, ³J=8.2 Hz, 1H, 2-H), 7.204-7.308 (m, overl. 3H, 1-H and 2× naphthyl-H), 7.390 (t, ³J=7.8 Hz, 1H, naphthyl-H), 7.508 (s, 1H, naphthyl-H), 7.692 (d, ³J=8.1 Hz, 2H, 2× naphthyl-H).

¹³C-NMR: 11.88, 23.46, 26.29, 27.37, 28.82, 29.76, 37.50, 38.71, 42.92, 43.94, 51.96, 51.99, 55.20, 67.69, 110.61, 111.46, 113.82, 123.03, 125.76, 125.93, 126.19, 126.29, 127.16, 127.26, 127.98, 132.51, 134.52, 137.89, 156.50, 157.47.

16β-(2-Hydroxyphenyl-methylamino)-17β-hydroxy-3-methoxy-estra-1,3,5(10)-triene (42)

obtained by conversion of 16β-[(E)-salicylidene imino]-17β-hydroxy-3-methoxy-estra-1,3,5(10)-triene and NaBH₄.

$C_{26}H_{33}NO_3$ (407.6), yield: 88%. F=163-167° C. [α]_D+ 97.7° (c=0.909). calc. C, 76.62; H, 8.16; N, 3.44. found: C, 75.91; H, 8.32; N, 3.50. MS (CI): 408 [M⁺].

¹H-NMR (CDCl₃): 0.85 (s, 3H, 18-H₃); 3.20 (m, 1H, 16-H); 3.71 (d, 1H, 17-H); 3.76 (s, 3H, OCH₃); 3.93 (q, 2H, —CH₂); 6.61-7.20 (m, 7H, aromat. H).

¹³C-NMR (CDCl₃): 12.39 (C-18), 52.04 (N—CH₂), 57.62 (C-16), 80.92 (C-17), 116.30, 119.10, 128.26, 128.74 (C₆H₄); 123.26 (H₂C—C₆H₄); 157.94 (HO—C₆H₄).

16α-(2-Hydroxyphenyl-methylamino)-17β-hydroxy-3-methoxy-estra-1,3,5(10)-triene (43)

obtained by conversion of 16α-[(E)-salicylidene imino]-17β-hydroxy-3-methoxy-estra-1,3,5(10)-triene and NaBH₄.

$C_{26}H_{33}NO_3$ (407.6), yield: 90.5%. F=167-169° C. [α]_D+ 26.2° (c=0.979). Calc.: C, 76.62; H, 8.16; N, 3.44. found: C, 76.65; H, 8.38; N, 3.51. MS (CI): 408 [M⁺].

¹H-NMR (CDCl₃): 0.79 (s, 3H, 18-H₃); 3.07 (m, 1H, 16-H); 3.50 (d, ³J=6.6 Hz, 1H, 17-H); 3.75 (s, 3H, OCH₃); 3.97 (d, ³J=13.9 Hz, 1H, —CH₂); 4.09 (d, ³J=13.9 Hz, 1H, —CH₂); 6.61-7.18 (m, 7H, aromat. H).

¹³C-NMR (CDCl₃): 12.11 (C-18), 51.51 (N—CH₂), 63.55 (C-16), 88.17 (C-17), 116.52, 119.17, 128.18, 128.76 (C₆H₄); 122.77 (H₂C—C₆H₄); 158.12 (HO—C₆H₄).

16β-(2-Hydroxyphenyl-methylamino)-17α-hydroxy-3-methoxy-estra-1,3,5(10)-triene (44)

obtained by conversion of 16β-[(E)-salicylidene imino]-17α-hydroxy-3-methoxy-estra-1,3,5(10)-triene and NaBH₄.

$C_{26}H_{33}NO_3$ (407.6), yield: 93.5%. F=158-161° C. [α]_D+ 62.0° (c=0.981). Calc. C, 76.62; H, 8.16; N, 3.44. found: C, 76.46; H, 8.37; N, 3.51. MS (CI): 408 [M⁺].

¹H-NMR (CDCl₃): 0.88 (s, 3H, 18-H₃); 3.03 (t, 1H, 16-H); 3.70 (s, 1H, 17-H); 3.76 (s, 3H, OCH₃); 4.02 (s, 2H, —CH₂); 6.62-7.21 (m, 7H, aromat. H).

¹³C-NMR (CDCl₃): 17.87 (C-18), 51.99 (N—CH₂), 67.88 (C-16), 84.88 (C-17), 116.42, 119.24, 128.23, 128.86 (C₆H₄); 122.77 (H₂C—C₆H₄); 157.96 (HO—C₆H₄).

16α-(2-Hydroxyphenyl-methylamino)-17α-hydroxy-3-methoxy-estra-1,3,5(10)-triene (45)

obtained by conversion of 16α-[(E)-salicylidene imino]-17α-hydroxy-3-methoxy-estra-1,3,5(10)-triene and NaBH₄.

$C_{26}H_{33}NO_3$ (407.6), yield: 87.6%. F=176-182° C. [α]_D+ 31.4° (C=0.921). Calc. C, 76.62; H, 8.16; N, 3.44. found: C, 76.46; H, 8.37; N, 3.51. MS (CI): 408 [M⁺].

¹H-NMR (CDCl₃): 0.71 (s, 3H, 18-H₃); 3.42 (m, 1H, 16-H); 3.76 (s, 3H, OCH₃); 3.81 (d, 1H, 17-H); 3.98 (q, 2H, —CH₂); 6.60-7.20 (m, 7H, aromat. H).

¹³C-NMR (CDCl₃): 17.15 (C-18), 51.23 (N—CH₂), 58.01 (C-16), 78.14 (C-17), 116.37, 118.98, 128.42, 128.65 (C₆H₄); 122.72 (H₂C—C₆H₄); 158.33 (HO—C₆H₄).

3,17β-Diydroxy-16α-(2-hydroxyphenyl-methylamino)-estra-1,3,5(10)-triene (46)

obtained by conversion of 3,17β-dihydroxy-16α-salicylidene imino-estra-1,3,5(10)-triene and NaBH₄.

$C_{25}H_{31}NO_3$ (393.52), F=144-145° C. (from methanol), $R_f$=0.

16β-(2-Hydroxyphenyl-methylamino)-17β-hydroxy-3-methoxy-13α-estra-1,3,5(10)-triene (47)

obtained by conversion of 16β-salicylidene imino-17β-hydroxy-3-methoxy-13α-estra-1,3,5(10)-triene) and NaBH$_4$.

$C_{26}H_{33}NO_3$ (407.55), F=92-98° C. (from methanol), $R_f$=0.03.

16α-(2-Hydroxyphenyl-methylamino)-17β-hydroxy-3-methoxy-13α-estra-1,3,5(10)-triene (48)

obtained by conversion of 16α-salicylidene imino-17β-hydroxy-3-methoxy-13α-estra-1,3,5(10)-triene) and NaBH$_4$.

$C_{26}H_{33}NO_3$ (407.55), F=131-136° C. (from methanol), $R_f$=0.09.

17α-(4-Methoxyphenyl-methylamino)-3-methoxy-estra-1,3,5(10)-triene (49)

obtained by conversion of 17α-(4-methoxyphenyl-methylenimino)-3-methoxy-estra-1,3,5(10)-triene) and NaBH$_4$.

$C_{27}H_{35}NO_2$ (405.58), colorless oil, $R_f$=0.51.

$^1$H-NMR: 0.746 (s, 3H, 18-H$_3$), 1.235-2.371 (m, overl., approx. 13H, aliph. H), 2.733 (d, overl., $^3$J=5.6 Hz, 1H, 17β-H), 2.865 (s, broad, 2H, 6-H$_2$), 3.361 (d, $^2$J=13.0 Hz, 1H, N-benzyl-H), approx. 3.740 (d, overl., $^2$J=13.0 Hz, 1H, N-benzyl-H), 3.778 (s, 3H, 3-MeO), 3.805 (s, 3H, MeO-phenyl), 6.637 (s, 1H, 4-H), 6.703 (d, $^3$J=8.4 Hz, 1H, 2-H), 6.868 (d, $^3$J=8.6 Hz, 2H, 2× phenyl-H), 7.205-7.264 (2×d, overl., $^3$J=8.4 and 8.6 Hz, 2H, 1-H and 2× phenyl-H).

$^{13}$C-NMR: 19.03, 24.97, 26.46, 28.08, 29.96, 30.30, 32.86, 39.28, 43.49, 45.13, 48.85, 52.27, 55.19, 55.26, 66.77, 111.41, 113.77, 126.31, 129.15, 132.98, 133.19, 138.10, 157.38, 158.50.

14α,17β-Diydroxy-15β-(2-hydroxyphenyl-methylamino)-estra-1,3,5(10)-triene (50)

obtained by conversion of 14β,17β-dihydroxy-15α-salicylidene imino-estra-1,3,5(10)-triene and NaBH$_4$.

$C_{26}H_{33}NO_4$ (423.56), F=178-181° C. (from ethanol), $R_f$=0.07.

14β,17β-Diydroxy-15α-(2-hydroxyphenyl-methylamino)-estra-1,3,5(10)-triene (51)

obtained by conversion of 14β,17β-dihydroxy-15α-salicylidene imino-estra-1,3,5(10)-triene and NaBH$_4$.

$C_{26}H_{33}NO_4$ (423.56), F=163-164.5° C. (from ethanol), $R_f$=0.17.

16β-(2-Hydroxy-3,5-di-tert-butylphenyl-methylamino)-17α-hydroxy-3-methoxy-estra-1,3,5(10)-triene (Ref 1)

obtained by conversion of 16β-(2-hydroxy-3,5-di-tert-butylphenyl-carbaldimino)-17α-hydroxy-3-methoxy-estra-1,3,5(10)-triene and NaBH$_4$.

$C_{24}H_{49}NO_4$ (519.76), F=184.5-186° C. (from ethanol/water), $R_f$=0.71, yield 82%, [α]$_D$+43° (c=0.934).

$^1$H-NMR ((400 MHz, CDCl$_3$, COSYDQF)):

d 5 0.88 (s, 3H, 18-H$_3$); 1.28 (s, 9H, tert-Bu), 1.43 (s, 9H, tert-Bu), 2.85 (m$_c$, 2H, 6-H$_2$), 3.09 (t, line form analysis: 2×d with 2×$^3$J approx. 8 Hz, 1H, 16α-H), 3.04 (s, 1H, 17β-H), 3.70 (s, 3H, OCH$_3$), 4.00 (m$_c$, 2H, 2× benzyl-H); 6.63-7.23 (m, 7H, Ar—H).

$^{13}$C-NMR: 53.03 (s, N—CH$_2$), 68.29 (s, C-16), 84.77 (s, C-17).

IR (KBr): 3299 (m) and 3569 (s, NH, OH), no CH=N line.
MS (70 eV); m/z (%) 519 (71) [M$^+$], 214 (100).
HR-MS: calc. 519.3710; found: 519.3712.
EA: calc. C, 78.60; H, 9.51; N, 2.70. found: C, 77.67; H, 9.93; N, 2.83.

Synthesis of Aminosteroid Precursors of the Abovementioned Embodiment Examples

16-Aminosteroids According to Example 1

16α-Bromo-3-methoxy-estra-1,3,5(10)-triene

To a stirred suspension of 2.67 g (15.0 mmol) N-bromosuccinimide in 18 ml dry dichloromethane, a solution of 3.93 g (15.0 mmol) triphenylphosphine in 18 ml dry dichloromethane is added dropwise at 10° C. After 5 min, 1.72 g (6.0 mmol) 16β-hydroxy-3-methoxy-estra-1,3,5(10)-triene are added and the mixture is stirred at room temperature for 2 h. After column chromatography of the reaction product on silica gel (60 g) using 300 ml of dichloromethane, the target compound is obtained in the form of colorless crystals.

$C_{19}H_{25}BrO$ (349.3); calc. C, 65.33; H, 7.21; Br, 22.88. found: C, 65.40; H, 7.41; Br, 22.95.

Yield 1.86 g (89%), F=108-111° C. [α]$_D$+118° (c=10.1).

$^1$H-NMR (CDCl$_3$): 0.718 (s, 3H, 18-H$_3$), 2.831 (m, 2H, 6-H$_2$), 3.757 (s, 3H, 3-MeO), 4.463 (m, 1H, 16β-H), 6.607 (s, 1H, 4-H), 6.694 (m, 1H, 2-H), 7.183 (d, $^3$J=8.62 Hz, 1H, 1-H).

16β-Azido-3-methoxy-estra-1,3,5(10)-triene

A stirred solution of 1.56 g (4.5 mmol) 16α-bromo-3-methoxy-estra-1,3,5(10)-triene and 0.67 g (13.7 mmol) lithium azide in 30 ml of DMSO is heated for 1 h to 80° C. After cooling, water is added dropwise and the resulting precipitate is collected by filtration, washed with water and dried under vacuum. 1.33 g (96%). F=80-85° C., after recrystallization from ether/methanol: F=84-87° C. [α]$_D$+60° (c=10.2).

$^1$H-NMR: 0.895 (s, 3H, 18-H$_3$), 2.830 (s, 2H, 6-H$_2$), 3.760 (s, 3H, 3-MeO), 4.086 (m, 1H, 16α-H), 6.613 (s, 1H, 4-H), 6.690 (m, 1H, 2-H), 7.181 (d, $^3$J=8.62 Hz, 1H, 1-H).

$C_{19}H_{25}N3O$ (311.4), calc. C, 73.28; H, 8.09; N, 13.49. found: C, 73.18; H, 7.97; N, 13.41.

16β-Amino-3-methoxy-estra-1,3,5(10)-triene

To a stirred solution of 1.28 g (4.1 mmol) 16β-azido-3-methoxy-estra-1,3,5(10)-triene in 30 ml abs. THF, 10 ml of a 1M lithium aluminum hydride solution in THF (Fluka) is added dropwise under cooling. The mixture is stirred for further 30 min at RT, followed by cautious addition of ether/water at 0° C. and subsequent addition of sodium tartrate solution. After three subsequent extractions of the aqueous phase with ether, the combined organic phases are washed twice with water, dried with sodium sulfate and concentrated. Yield after recrystallization from hexane: 1.05 g (89%), white solid matter with F=90-94° C.

$C_{19}H_{27}NO$ (285.4): calc. C, 79.95; H, 9.53; N, 4.90. found: C, 79.23; H, 9.44; N, 4.74. [α]$_D$ (pyridine)+67° (c=9.6).

¹H-NMR (CDCl₃): 0.923 (s, 3H, 18-H₃), 2.850 (s, 2H, 6-H₂), 3.755 (s, 3H, 3-MeO), 3.481 (m, 1H, 16α-H), 6.608 (s, 1H, 4-H), 6.686 (m, 1H, 2-H), 7.183 (d, $^3$=8.64 Hz, 1H, 1-H); after addition of trichloroacetyl isocyanate: 0.918 (s, 1H, 18-H₃), 4.320 (m, 1H, 16α-H), 8.012 (d, $^3$J=7.00 Hz, 1H, 16β-NH), 8.634 (s, 1H, NH—CO).

3-Methoxy-16β-tosyloxy-estra-1,3,5(10)-triene 4.5 g (15.7 mmol) 16β-hydroxy-estra-1,3,5(10)-triene, 9.0 g (47.2 mmol) p-tosylchloride and 45 ml abs. pyridine are reacted with each other for 3 days at 5° C. After addition of iced water and collection by filtration, the product is washed with water and dried. After column chromatographic purification (75 g silica gel, benzene), 6.6 g (95%) of the tosylate is obtained. F=144-150° C., after recrystallization from dichloromethane/methanol: F=151-155° C.

C₂₆H₃₂O₄S (440.6), calc. C, 70.88; H, 7.32; S, 7.28. found: C, 71.05; H, 7.46; S, 7.31. [α]$_D$+55° (c=10.3).
¹H-NMR (CDCl₃): 0.894 (s, 3H, 18-H₃), 2.435 (s, 3H, CH₃-phenyl), 3.745 (s, 3H, 3-MeO), 4.973 (m, 1H, 16α-H).

16α-Azido-3-methoxy-estra-1,3,5(10)-triene 3.3 g (7.5 mmol) of 3-methoxy-16β-tosyloxy-estra-1,3,5 (10)-triene and 0.99 g (15.7 mmol) lithium azide in 66 ml of DMSO are reacted as described above. Yield: 2.15 g (92%), F=80-89° C., after recrystallization from acetone: F=89-92° C.

C₁₉H₂₅N₃O (311.4): calc. C, 73.28; H, 8.09; N, 13.49. found: C, 73.32; H, 8.30; N, 13.53. [α]$_D$+90° (c=10.1).
¹H-NMR (CDCl₃): 0.757 (s, 3H, 18-H₃), 2.834 (s, 2H, 6-H₂), 3.759 (s, 3H, 3-MeO), 4.052 (m, 1H, 16β-H), 6.614 (s, 1H, 4-H), 6.695 (m, 1H, 2-H), 7.181 (d, $^3$J=8.52 Hz, 1H, 1-H).

16α-Amino-3-methoxy-estra-1,3,5(10)-triene 2.62 g (8.4 mmol) 16α-azido-3-methoxy-estra-1,3,5(10)-triene in 80 ml abs. THF are reacted with 20 ml 1M lithium aluminum hydride solution as described above. After recrystallization from heptane, 2.05 g (85%) of a white solid matter is obtained.

F=82-85° C.
C₁₉H₂₇NO (285.4), calc. C, 79.95; H, 9.53; N, 4.90. found: C, 80.39; H, 9.59; N, 4.92.
[α]$_D$ (pyridine)+81 (c=9.5).
¹H-NMR (CDCl₃): 0.746 (s, 3H, 18-H₃), 2.833 (m, 2H, 6-H₂), 3.575 (m, 1H, 16β-H), 3.754 (s, 3H, 3-MeO); after addition of trichloroacetyl isocyanate: 0.789 (s, 3H, 18-H₃), 2.828 (m, 2H, 6-H₂), 3.744 (s, 3H, 3-MeO), 4.390 (m, 1H, 16β-H), 7.912 (d, $^3$J=7.23 Hz, 1H, 16α-NH), 8.662 (s, 1H, NH=CO).

17-Aminosteroids According to Example 2

17β-Amino-3-methoxy-estra-1,3,5(10)-triene

To a well-stirred solution of 17-hydroxyimino-3-methoxy-estra-1,3,5(10)-triene (2.42 g, 8.1 mmol) in 200 ml abs. methanol and 40 ml abs. THF, 2.19 g MoO₃ (15.2 mmol) is added. After cooling to 0° C., NaBH₄ (14.8 g, 15.2 mmol) is added in small amounts at a temperature between 0 and 10° C. The mixture is stirred for another 30 min at RT, followed by addition of a solution of 5 g KOH in 20 ml water. The solution is left for 12 h at 0° C. without stirring and then filtered. The filter residue is washed twice with 30 ml methanol each. The filtrate is then reduced under vacuum to 100 ml, transferred into ice/water and extracted with CHCl₃ (2× with each 50 ml). The combined organic phases are washed three times with 70 ml water each, dried over Na₂SO₄ and concentrated: 1.7 g (85.8%) of a colorless solid matter. F=83-85° C.

¹H-NMR (CDCl³): 0.65 (s, 3H, 18-H₃), 2.73 (t, 1H, 17α-H), 2.81 (m, 2H, 6-H₂), 3.75 (s, 3H, OCH₃), 6.61 (s, 1H, 4-H), 6.69 (m, 1H, 2-H), 7.16 (d, $^3$J=8.54 Hz; 1H, 1-H); after addition of trichloroacetyl isocyanate (TAI): 0.80 (s, 3H, 18-H₃), 3.89 (q, 1H, 17α-H), 7.89 (1H, d, $^3$J=8.57 Hz, 17β-NHCO), 8.67 (s, 1H, NH). After recrystallization from ether: F=113-115° C.

17α-Amino-3-methoxy-estra-1,3,5(10)-triene

3-Methoxyestra-1,3,5(10)-triene-17β-ol (6 g, 0.01 mol) is dissolved in 20 ml pyridine and a solution of p-toluenesulfonyl chloride (2.85 g, 0.015 mol) in pyridine (10 ml) is added dropwise under cooling with ice. After 24 h without agitation at RT, the mixture is poured onto ice/water (500 g) and 10 ml conc. sulphuric acid is added. The precipitate is filtered off, washed thoroughly with water, recrystallized from acetone/water and dried in an exsiccator over P₂O₅.

The 17β-tosyloxy compound obtained (5.16 g, 11.7 mmol) is reacted with NaN₃ (5.68 g, 102.8 mmol) at 100° C. in abs. HMPTA (70 ml) under addition of 18-crone-6 (1.5 g) for 20 h. After cooling, the reaction mixture is given into ice/water and extracted with methylene chloride. The organic phase is separated and washed several times with water. After vacuum concentration, 3.5 g (96.1%) of the 17α-azide is obtained as oily raw product.

¹H NMR (CDCl₃) 0.76 (s, 3H, 18-H₃), 3.57 (d, 1H, 17β-H).

The azide (710 mg, 2.28 mmol) is dissolved in abs. THF (10 ml), then LiAlH₄ (1 M solution in THF, Fluka, 10 ml) is added and the mixture is heated for 2 h under reflux. After cooling to 0° C., an ether/H₂O mixture is carefully added, followed by addition of conc. aqueous NH₄Cl solution and filtration. The filter residue is washed with ether and the aqueous phase is washed twice with 30 ml ether each. The combined organic phases are dried, then dry gaseous HCL is injected. The precipitated hydrochloride is removed by filtration and recrystallized from ethanol. To obtain the amine, a concentrated solution of the hydrochloride in methanol is added to a solution of 1 g KOH in 10 ml water. After ether extraction, washing with water and drying, 322 mg (49.5%) of the amine is obtained in the form of a wax-like product.

¹H-NMR (CDCl₃): 0.71 (s, 3H, 18-H₃), 2.98 (d, 1H, 17β-H); after addition of TAI: 0.85 (s, 3H, 18-H₃), 3.97 (t, 1H, 17β-H), 7.88 (1H, d, $^3$J=8.23 Hz, 17α-NHCO), 8.73 (s, 1H, NH).

Example of Steroid Amino Alcohol Synthesis According to Example 3 (Scheme 3.1. and 3.2.)

16β-Amino-3-methoxy-estra-1,3,5(10)-triene-17α-ol

16β-Azido-3-methoxy-estra-1,3,5(10)-triene-17α-ol 5.0 g of 16α,17α-epoxy-3-methoxy-estra-1,3,5(10)-triene, 20 g sodium azide, 100 ml abs. DMSO and 30 ml glacial acetic acid are stirred at 110° C. 7 h under argon atmosphere. The mixture is then poured into water, extracted with ether, washed with 1N NaOH and then with water. After drying and removal of the solvent by distillation, the residue is chromatographed with benzene on 50 g aluminum oxide (neutral, activity level 1). Recrystallization from methanol/water yields 4.2 g (73%) of the azide.

C₁₉H₂₅N₃O₂ (327.4), calc. C, 69.70; H, 7.70; N, 12.83. found: C, 69.77; H, 752; N, 12.72.

F=100-101° C.; [α]$_D$+86°. IR: 2092 (N$_3$), 3610 (OH); $^1$H-NMR: 3.75 (16α-H, 17β-H, OCH$_3$), 17α-OCONH-COCCl$_3$-compound: 4.85 (s, 17β-H).

16β-Amino-3-methoxy-estra-1,3,5(10)-triene-17α-ol 1.0 g 16β-azido-3-methoxy-estra-1,3,5(10)-triene-17α-ol, 10 ml methanol, 2 ml 80% hydrazine hydrate and a spatula tip of Raney nickel are heated on a water bath for 15 min. After filtration, the Raney nickel is washed with methanol, subsequently wash fluid and filtrate are combined and methanol is removed by distillation under vacuum. The residue is recrystallized from methanol/ether. Yield: 0.8 g (87%), F=158-160° C.; [α]$_D$+68° (pyridine).

C$_{19}$H$_{27}$NO$_2$ (301.4), calc. C, 75.71; H, 9.031; N, 4.65. found: C, 75.60; H, 8.99; N, 4.51. IR: 3365 cm (NH). 3605 (OH).

16α-Amino-3-methoxy-estra-1,3,5(10)-triene-17β-ol

17α-Azido-3-methoxy-estra-1,3,5(10)-triene-16β-ol 1.0 g 16β,17β-epoxy-estra-1,3,5(10)-triene, 4.0 g sodium azide, 20 ml abs. DMSO and 3 ml glacial acetic acid are stirred for 4 h at 120° C. under argon. The purification was performed as described above. The dry raw product is separated into two fractions by preparative layer chromatography on silica gel PF (Merck) using benzene/ether 3:2 as eluent. If required, both fractions are purified further by preparative layer chromatography. Obtained from the polar fraction is 0.23 g 17α-azido-3-methoxy-estra-1,3,5(10)-triene-16β-ol (20%) as colorless oil.

$^1$H-NMR: 3.50 (s, 17β-H), 425 (m, 16α-H); 16β-OCONHCOCCl$_3$-compound: 3.71 (s, 17β-H), 5.13 (m, 16α-H).

16α-Azido-3-methoxy-estra-1,3,5(10)-triene-17β-ol

Variant 1: From the non-polar faction obtained during the synthesis of 17α-azido-3-methoxy-estra-1,3,5(10)-triene-16β-ol by preparative layer chromatography, 0.25 g 16α-azido-3-methoxy-estra-1,3,5(10)-triene-17β-ol (22%) is obtained by recrystallization from methanol/water. F=112-114° C.; [α]$_D$+38°. IR: 2090 (N$_3$), 3612 (OH); NMR: approx. 3.68 (16β-H, 17α-H, OCH$_3$). 17β-OCONHCOCCl$_3$-compound: 3.85 (m, 16β-H), 4.88 (d, 17α-H).

C$_{19}$H$_{25}$N$_3$O$_2$ (327.4), calc. C, 69.70; H, 7.70; N, 12.83. found: C, 69.71; H, 7.53; N, 12.86.

Variant 2: 18.2 g 16β-bromo-3-methoxy-estra-1,3,5(10)-triene-17β-ol are stirred with 10.8 g sodium azide in 180 ml DMSO for 40 min at 90° C. After cooling, water is added dropwise and the precipitate is filtered off. The obtained crude product is washed with water and dried. For the separation of the ketone fraction, the raw product is heated in 90 ml methanol and 6.8 ml glacial acetic acid with 6.1 g Girard reagent P for 1 h. The mixture is then poured into water containing 5.7 g (water-free) sodium carbonate, followed by extraction with ether, washing with water and removal of the solvent by distillation. The residue is recrystallized from methanol/water. Yield: 14.6 g (89%), F=112-114° C.

16α-Amino-3-methoxy-estra-1,3,5(10)-triene-17β-ol 5.0 g 16α-azido-3-methoxy-estra-1,3,5(10)-triene-17β-ol, 100 ml methanol, 10 ml of 80% hydrazine hydrate and 4 spatula tips of Raney nickel are heated for 30 min on a water bath. Purification and recrystallization are performed as described for the purification of 16α-amino-3-methoxy-estra-1,3,5(10)-triene-17β-ol. Yield: 3.2 g (69%). F=158-161° C.; [α]$_D$+41° (pyridine). IR: 3367 (NH). 3601 (OH);

C$_{19}$H$_{27}$NO$_2$ (301.4), calc. C, 75.71; H, 9.03; N, 4.65. found: C, 75.78; H, 9.02; N, 4.65.

16β-Amino-3-methoxy-estra-1,3,5(10)-triene-17β-ol 1.0 g 16β-azido-3-methoxy-estra-1,3,5(10)-triene-17β-ol are reduced with 20 ml methanol, 2 ml 80% hydrazine hydrate and one spatula tip of Raney nickel by procedures as described for the purification of 16β-Amino-3-methoxy-estra-1,3,5(10)-triene-17α-ol. Recrystallization is performed from methanol/ether. Yield: 0.7 g (76%). F=152-157° C.; [α]$_D$+59° (pyridine). IR: 3300 (broad), 3417 (OH, NH), 3601 (OH).

C$_{19}$H$_{27}$NO$_2$ (301.4), calc. C, 75.71; H, 9.03; N, 4.65. found: C, 75.55; H, 8.86; N, 4.56.

16α-Amino-3-methoxy-estra-1,3,5(10)-triene-17α-ol

16α-Azido-3-methoxy-estra-1,3,5(10)-triene-17-one

To a solution of 20 g 16α-azido-3-methoxy-estra-1,3,5(10)-triene-17β-ol in 1 l acetone, 40 ml of 8 N chromium trioxide solution in conc. sulfuric acid is added dropwise at 0° C. and under stirring. After 2 h, 2 ml isopropanol are added and the reaction product is precipitated in crystalline form by dropwise addition of water. The product is filtered off, washed with water, dried and recrystallized from acetone/water. Yield: 16 g (81%), F=118-122° C.; [α]$_D$+405°. IR: 1747 cm (CO), 2095 (N$_3$).

C$_{19}$H$_{23}$N$_3$O$_2$ (325.4); calc. C, 70.13; H, 7.12; N, 12.91. found: C, 70.23; H, 6.97; N, 12.71.

16α-Azido-3-methoxy-estra-1,3,5(10)-triene-17α-ol

To a suspension of 3.0 g 16α-azido-3-methoxy-estra-1,3,5(10)-triene-17-one in 75 ml abs. ether, 0.7 g lithium boron hydride are added in portions under stirring at 0° C. and under protective atmosphere. After 80 min, a small amount of acetone is added, followed by the addition of water after another 5 min. The ether phase is removed, washed again with water and dried. The residue obtained after removal of the solvent by distillation is chromatographed on 75 g silica gel with 2 l benzene. Yield after recrystallization from methanol: 2.0 g (67%). F=97-99° C.; [α]$_D$ 0°; IR: 2110 (N$_3$). 3540, 3610 (OH).

C$_{19}$H$_{25}$N$_3$O$_2$ (327.4), calc. C, 69.70; H, 7.70; N, 12.83. found: C, 69.55; H, 7.74; N, 12.79.

Using 150 ml acetone, finally also 0.4 g 16α-azido-3-methoxy-estra-1,3,5(10)-triene-17β-ol (13%) is eluted.

16α-Amino-3-methoxy-estra-1,3,5(10)-triene-17α-ol 2.0 g 16α-azido-3-methoxy-estra-1,3,5(10)-triene-17α-ol are reduced with 40 ml methanol, 4 ml of 80% hydrazine hydrate and 2 spatula tips Raney nickel in the above described manner. Recrystallization is performed from methanol/ether. Yield: 1.3 g (71%), F: at 145° C. conversion, at 193-198° C. melting; [α]$_D$+44° (pyridine);

IR: 3290 (broad), 3400 (NH, OH), 3618 (OH).

C$_{19}$H$_{27}$NO$_2$ (301.4); calc. C, 75.71; H, 9.03; N, 4.65. found: C, 75.71; H, 9.13; N, 4.73.

Aminocholanes According to Example 4

3α-Azido-5α-cholestane 4 g (7.37 mmol) 3β-tosyloxy-5α-cholestane and 0.99 g (15.23 mmol) NaN$_3$ are heated under stirring in 25 ml hexamethylphosphoric acid triamide (HMPT) for 3 h to 90° C. The reaction mixture is cooled and given into 100 ml ice water, the precipitated raw product subsequently removed by filtration, washed with water and dissolved in 60 ml ether. The organic phase is washed twice with water, dried over $Na_2SO_4$ and concentrated. The resulting wax-like product is directly processed further:

Yield 95%, F=49-51° C. IR: 2103 (vs, $N_3$). $C_{27}H_{47}N3$ (413.7), calc. C, 78.39; H, 11.45; N, 10.16. found: C, 78.11; H, 11.40; N, 9.98.

3α-Amino-5α-cholestane

To a solution of 2.04 g (4.83 mmol) 3α-azido-5α-cholestane in 50 ml THF, 16 ml (16 mmol) of a 1M solution of $LiAlH_4$ in ether are carefully added dropwise. The mixture is heated for 4 h under reflux, cooled to RT, followed by cautious addition of 5 ml of a saturated $NH_4Cl$ solution. After filtration and washing of the residual filtrate twice with ether, the ether phase is dried over $Na_2SO_4$ and concentrated. The amine is obtained as white solid and directly processed further. Yield 96%, F=95-97° C. $C_{27}H_{49}N$ (387.7), calc. C, 83.65; H, 12.74; N, 3.61. found: C, 83.30; H, 12.42; N, 3.65.

Amino alcohols of cholane according to example 4

1α-Azido-cholestane-2β,3β-diol-3-acetate 2 g 1,2β-epoxy-cholestane-3β-ol-acetate and 6 g sodium azide in 75 ml dimethyl sulfoxide are heated for 20 h on the boiling water bath and under stirring in the presence of a few drops conc. sulphuric acid. The mixture is then diluted with ice water and the precipitate is redissoled in ether. The ethereal solution is washed several times with water, dried, and the solvent is removed by distillation. The residue crystallizes from hexane in the form of colorless needles with a m.p. 163° C. Yield 1.5 g.

$C_{29}H_{49}N_3O_3$ (487.7); calc. C, 71.41; H, 10.13; N, 8.62. found: C, 71.56; H, 10.08; N, 8.76. $[\alpha]_D$+49° (c=2).

1α-Azido-cholestane-2β,3β-diol

Variant 1: Upon heating of 0.5 g 1α-azido-cholestane-2β, 3β-diol-3-acetate for 30 min. with 5% methanolic potassium hydroxyde under reflux, colorless crystals precipitate upon dilution with water, which, after recrystallization from aqueous methanol, melt at 143-144° C. Yield 0.41 g. $C_{27}H_{47}N_3O_2$ (445.7), calc.: C, 72.75; H, 10.64; N, 9.43. found: C, 72.80; H, 10.61; N, 9.59. $[\alpha]_D$+27° (c=2).

Variant 2: If 2.1 g 1,23-epoxy-cholestane-3β-ol are converted with $NaN_3$ in dimethyl sulfoxide, 1.7 g of colorless crystals are obtained (from water/methanol) with a m.p. of 143-144° C.

1α-Amino-cholestane-2β,3β-diol-3-acetate

Upon heating of a solution of 2.7 g 1α-azido-cholestane-2β,3β-diol-3-acetate in 25 ml ethanol with 8 ml hydrazine hydrate and 1 spatula tip of Raney nickel, colorless flakes crystallize out after approximately 1 min. Ethanol is added until the precipitate solubilizes. After 5 min, the catalyst is filtered off. Upon cooling, colorless flakes crystallize out which, after recrystallization from ethanol, melt at 188-189° C. Yield 1.1 g. $C_{29}H_{51}NO_3$ (461.7). $[\alpha]_D$+30° C. (pyridine).

From the combined mother liquors, additional 0.9 g of the target compound with a m.p. of 186-189° C. can be isolated.

1α-Amino-cholestane-2β,3β-diol 0.5 g of the above described acetate are dissolved in 5% methanolic potassium hydroxyde, heated for 20 min under reflow, followed by dilution with water. The resulting precipitate is then recrystallized from ethanol. Obtained is 0.35 g of colorless flakes with a m.p of 188-189° C.

$C_{27}H_{49}NO_2$ (419.7). calc. C, 77.27; H, 11.77; N, 3.34. found: C, 77.13; H, 12.07; N, 3.40.

$[\alpha]_D$+31° (pyridine).

2β-Amino-cholestane-3-ol 4 g 2β-azido-cholestane-3-ol and 0.2 g lithium aluminium hydride are stirred in 50 ml abs. ether for one day at room temperature. After careful decomposition with water and repeated ether extraction, the combined ethereal solutions are washed with water, dried over sodium sulfate and the solvent is reduced to 50 ml. Upon introduction of hydrogen chloride, the corresponding hydrochloride crystallizes out in the form of colorless needles which, after recrystallization from acidified methanol, melt at 254-256° C.

$C_{27}H_{49}NO$—HCl (440.1); calc. N, 3.18. found: N, 3.34.

0.2 g of the hydrochloride are dissolved in a small amount of hot methanol, then diluted sodium hydroxide solution is added until turbidity is observed. 0.15 g of colorless flakes crystallize out which, after recrystallization from methanol, melt at 206-207° C.

$C_{27}H_{49}NO$ (403.7), calc. C, 80.32; H, 12.24; N, 3.47. found: C, 80.56; H, 12.26; N, 3.64; $[\alpha]_D$+34° (pyridine).

3α-Amino-cholestane-2β-ol

Variant 1: To a solution of 1 g 3α-azido-cholestane-2,3-ol in 10 ml ethanol, 3 ml of 80% hydrazine hydrate a spatula tip of Raney nickel is added and heated to boiling point. The reduction takes place under vigorous gas evolution, and after approximately 1 min, the amino alcohol crystallizes out. The amino alcohol is brought back into solution by addition of ethanol and heated, until the gas evolution stops.

The catalyst is removed by filtration and the crystallized base is recrystallized from ethanol. M.p. 203-204° C. Yield 0.65 g.

$C_{27}H_{49}NO$ (403.7), calc. C, 80.32; H, 12.24; N, 3.47. found: C, 80.30; H, 12.21; N, 3.54; $[\alpha]_D$+38° (pyridine). Yield 0.25 g.

Variant 2: 0.5 g azidoalcohol are reduced with $LiAlH_4$, F=202° C., yield 0.25 g.

4β-Amino-cholestane-5α-ol 1 g 4β-Azido-cholestane-5α-ol is reduced in ethanol with hydrazine hydrate/Raney nickel and recrystallized from methanol. M.p. 116° C. Yield 0.5 g. From the mother liquors, further 0.3 g amino alcohol with m.p. of 113-116° C. can be obtained.

$C_{27}H_{49}NO$ (403.7), calc. C, 80.32; H, 12.24; N, 3.47. found: C, 80.47; H, 12.09; N, 3.57; $[\alpha]_D$+42° (pyridine).

5α-Amino-cholestane-3β,6β-diol

If 1 g of 5α-azido-cholestane-3β,6β-diol-3-acetate are reduced with $LiAlH_4$, 0.6 g colorless needles with a m.p. of 242-243° C. crystallize out from methanol.

$C_{27}H_{49}NO_2$ (419.7). calc. C, 77.27; H, 11.77; N, 3.34. found: C, 77.55; H, 11.85; N, 3.35. $[\alpha]_D$−6° (pyridine).

5α-Amino-cholestane-3β,6β-diol-3-acetate

Upon reduction of 0.75 g of 5-azido-cholestane-3β,6β-diol-3-acetate according to the hydrazine hydrate method, 0.6 g of colorless needles with a m.p. of 179° C. is obtained from methanol. $C_{29}H_{51}NO_3$ (461.7), calc. C, 75.44; H, 11.13; N, 3.03. found: C, 75.67; H, 11.33; N, 3.25.

$[\alpha]_D$–22° (pyridine).

6β-Amino-cholestane-3β,5α-dio3-acetate

The reduction of 3.5 g 6β-azido-cholestane-3β,5α-diol-3-acetate with hydrazine hydrate/Raney nickel yields 2.8 g colorless flakes with a m.p. of 190-191° C. (from ethanol).

$C_{29}H_{51}NO_3$ (461.7); calc. C, 75.44; H, 11.13; N, 3.03. found: C, 75.13; H, 11.10; N, 3.22. $[\alpha]_D$–17° (pyridine).

6β-Amino-cholestane-3β,5α-diol

If 1.25 g 6β-amino-cholestane-3β,5α-diol-3-acetate are heated with 8 ml 5% methanolic potassium hydroxide solution for 30 min under reflow, colorless needles crystallize out upon cooling which after recrystallization from methanol, melt at 199-200° C. Yield 0.95 g.

$C_{27}H_{49}NO_2$ (410.7), calc. C, 77.27; H, 11.77; N, 3.34. found: C, 77.01; H, 11.61; N, 3.60.

$[\alpha]_D$+1° (pyridine).

6β-Amino-cholestane-3β,7α-diol 1.25 g 6β-azido-cholestane-3β,7α-diol-3-acetate are reduced as described above with $LiAlH_4$ and diluted with ether, followed by slow addition of $2NH_2SO_4$ until an acidic reaction is clearly observed. The crystalline precipitate is filtered off, washed with ether and recrystallized from methanol. M.p. 257-258° C. (decomp.). By solvatation of the sulfate in hot methanol and addition of dil. sodium hydroxide solution, colorless needles are obtained which, after recrystallization from benzene/methanol (1:3) followed by recrystallization from methanol, melt at 191-192° C. Yield 0.8 g.

$C_{27}H_{49}NO_2$ (419.7), calc. C, 77.26; H, 11.77; N, 3.34. found: C, 77.19; H, 11.73; N, 3.41.

$[\alpha]_D$+21° (pyridine).

6β-Amino-cholestane-3β,7α-diol-3-acetate

If 0.8 g 6β-azido-cholestane-3β,7α-diol-3-acetate in ethanol are reduced with hydrazine hydrate/Raney nickel, after recrystallization from methanol 0.5 g colorless needles are obtained with a m.p. of 136° C.

$C_{29}H_{51}NO_3$ (461.7), calc. C, 75.44; H, 11.13; N, 3.03. found: C, 75.20; H, 11.41; N, 3.31.

$[\alpha]_D$–1° (pyridine).

7α-Amino-cholestane-3β,6β-diol

Upon reduction of 1.5 g 7a-azido-cholestane-3β,6β-diol-3-acetate with $LiAlH_4$ in abs. ether and decomposition with diluted hydrochloric acid, 1.2 g of the hydrochloride is obtained after recrystallization from methanol with a m.p. of 303-304° C.

$C_{27}H_{56}NO_2$—HCl (456.2), calc. N, 3.07. found: N, 3.10.

0.8 g of the hydrochloride is dissolved in hot methanol and diluted sodium hydroxide is added until turbidity is observed. Colorless needles precipitate which, after recrystallization from methanol, melt at 217-218° C. Yield 0.51 g.

$C_{27}H_{49}NO_2$ (419.7), calc. C, 77.26; H, 11.77; N, 3.34. found: C, 77.30; H, 11.50; N, 3.38.

$[\alpha]_D$+14° (pyridine).

7α-Amino-cholestane-3β,6β-diol-3-acetate 1.25 g 7α-azido-cholestane-3β,6β-diol-3-acetate are reduced with hydrazine hydrate/Raney nickel in ethanol. Obtained from ethanol is 0.75 g of colorless crystals with a m.p of. 212° C. $C_{29}H_{51}NO_3$ (461.7), calc. C, 75.44; H, 11.13; N, 3.03. found: C, 75.34; H, 11.01; N, 3.16. $[\alpha]_D$-13° (pyridine).

Example 9

Test of Drug Combinations

In order to assess the potential of the compounds of the present invention in combination therapies with other, clinically already well established anti-malaria drugs, compounds 2, 18 and 41 were tested in combination assays with chloroquine, artemisinin, artesunate, artemether, mefloquine as well as methylene blue. Remarkable was a considerably synergistic effect of all three compounds with artemisinin and the derivate thereof, artesunate. This is reflected by fractional inhibitory concentrations ($FIC_{50}$ and $FIC_{90}$ values) which are lower than 1.

Method: For the assessment of synergy effects, isotope-based sensitivity assays on the basis of a semiautomated microdilution method were performed. This method is depends on the incorporation of [3H]-hypoxanthine which is taken up by the parasites as precursor of purine deoxynucleotides for DNA synthesis. A twofold serial dilution series of the initial concentration of each compound was prepared in 96-well microtiter plates (Nunc). Both drugs to be tested in combination are each applied alone in this assay as well as in pre-determined concentration ratios of 1:1, 1:3 and 3:1.

Parasites (*Plasmodium falciparum*, strain 3D7) were incubated at a parasitemia of 0.125% (approx. 70% ring stages) and a hematocrit of 1.25% in hypoxanthine-free medium. After 48 hours, 0.5 Ci [3H]-hypoxanthine was added to each well and plates were incubated for further 24 h. The cells in each well were harvested on a Plexiglas filter (Perkin-Elmer, Rodgau-Jügesheim, Germany), washed and dried. In this method, the radioactivity in "counts per minute" is assumed to be proportional to the growth of the parasites. $IC_{50}$—as well as $IC_{90}$ values, in other words the concentration of active substance resulting in 50% or 90% reduction of [3H] hypoxanthine uptake, respectively, were calculated. Die "fractional inhibitory concentrations (FIC)" of each of the active substances was determined as follows:

$$FIC_{50}A=[IC_{50}(A+B)]/IC_{50}A;$$

$$FIC_{50}B=[IC_{50}(B+A)]/IC_{50}B; \text{ and}$$

$$FIC_{50}=FIC_{50}A+FIC_{50}B.$$

Identical calculations were performed to determine the respective $IC_{90}$ values.

FIC values greater than 1 become evident in convex isobolograms and indicate an antagonistic effect of active substances. The five measurement values, i.e. IC values of each of the single substances as well as values of the predetermined active substance combinations 1:1, 1:3 and 3:1, are above the dashed line.

FIC values of 1 indicate an additive effect of substances. Measurement values are on the dashed line.

FIC values lower than 1 indicate synergistic effects of the combined substances. Measurement values are below the dashed line, and the isobolograms are concave. For methodical details, please see: Akoachere M, Buchholz K, Fischer E, Burhenne J, Haefeli W E, Schirmer R H, Becker K (2005) In vitro assessment of methylene blue on chloroquine-sensitive and -resistant *Plasmodium falciparum* strains reveals synergistic action with artemisinins. *Antimicrob Agents Chemother* 49: 4592-4597.

Exemplarily given in FIGS. 3 and 4 are isobolograms for substance 18 with artemisinin and artesunate. For the diagrams, in each case $FIC_{90}$ values were used. In addition shown are isobolograms for substance 2 ($FIC_{90}$ values) and substance 41 ($FIC_{50}$ values) with artemisinin. All experiments were carried out with *Plasmodium falciparum* strain 3D7. All isobolograms clearly demonstrate a synergistic effect of the active compounds tested.

Example 10

Figure 2:
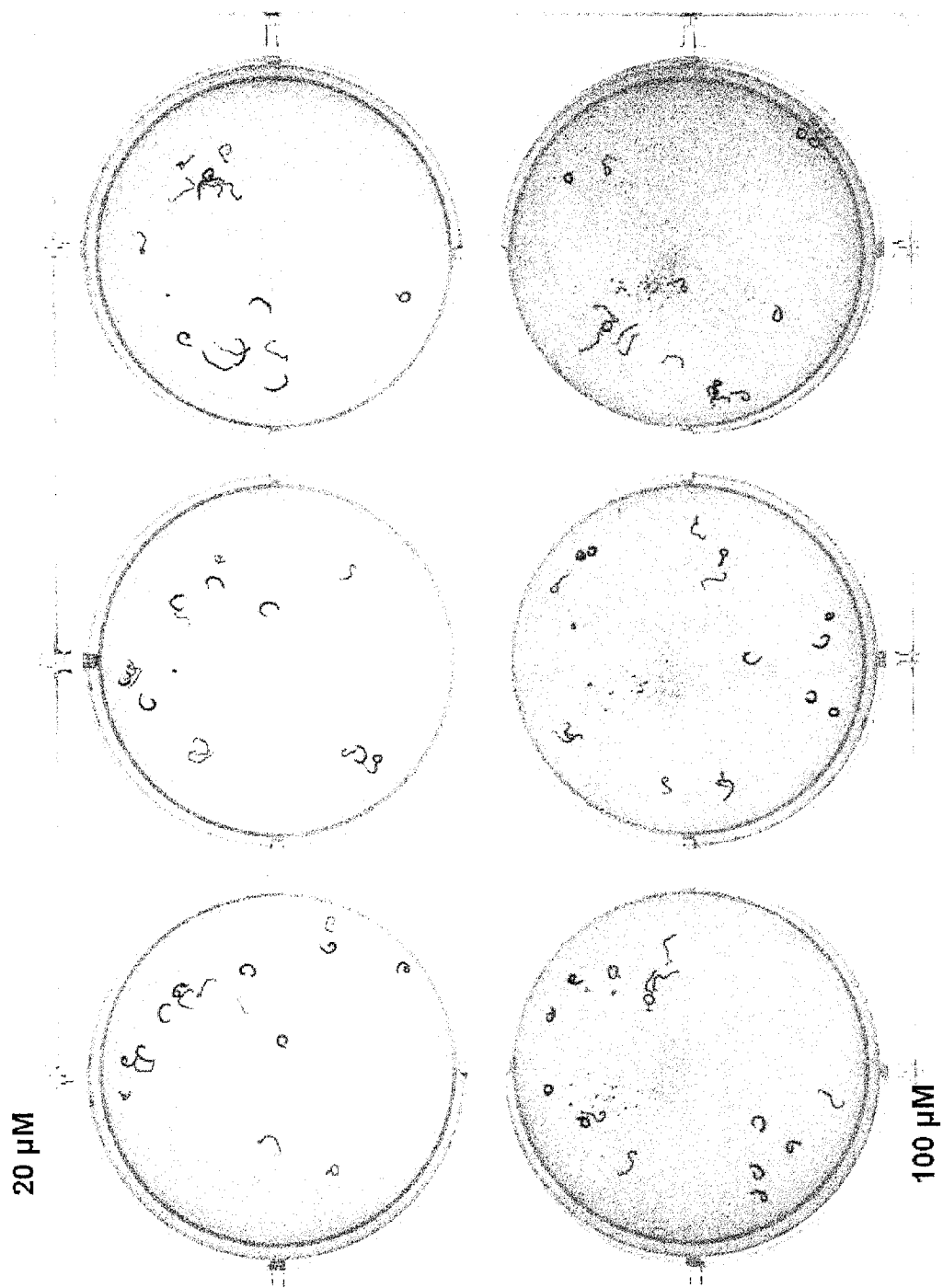
FIG. 2: Eight pairs of adult *S. mansoni* each after 48 hours of incubation with 20 μM and 100 μM of compound 18.

In Vitro Treatment of Adult *S. Mansoni* Couples with Compounds 41, 18 and 26 for 24 Hours Compounds 2, 18 and 41 were tested by Prof. Dr. Grevelding, Parasitology, Veterinary Medicine, University of Gießen, also in the parasite *Schistosoma mansoni*. While all three compounds had a considerable effect on the parasites, clear differences were evident with respect to the compound tested, the concentration applied in the assay as well as the macroscopically detectable phenotypic effects. Each test was performed with 3 groups of 10 worms each. Remarkable was that different effects on the worms with respect to morphological alterations could be observed. Compound 41 lead to dorsal bending, whereas compound 18 resulted in ventral bending. If compound 2 was used, the worms appeared to be ventrally curved in a cork-screw like manner. Exemplarily shown in FIGS. 1 and 2 is an image of a control assay and an image of trematodes after 48 hours of incubation with compound 18.

Each one of the three groups (one group per well) comprised 10 pairs of adult *S. mansoni* were incubated with the substance to be tested for 24 h. As control served three groups which were incubated with medium (M199) and three groups which were incubated with medium and DMSO as solvent of the test substances. Evaluation was done visually using a microscope.

Results:

After 24 hours, pairs of the control group (only medium or DMSO controls) were all attached via the sucker, looked vital and normal and had a stretched shape. Also intestinal peristalsis and sucker movement was present. Egg production was also normal.

After 24 hours of incubation with 20 µM of compound 41 of the present invention, in only two of the groups a couple was detectable. All trematodes were detached. Intestinal peristalsis was reduced, and sucker movement no longer visible. Males barely moved and showed only twitching, while females displayed more twitching movements than males. Males were curved towards the dorsal side. Almost no eggs could be detected.

After 24 hours of incubation with 100 µM of compound 41 of this invention, in only in one of the groups a couple was detectable. All trematodes were detached. Intestinal peristalsis and sucker movement was no longer visible. Males showed almost no motility, only occasional spontaneous twitching was observed. Females also showed only spontaneous sporadic and twitching movements. Males were curved towards the dorsal side. Almost no eggs could be detected.

After 24 hours of incubation with 20 µM of compound 18 of this invention, no couples could be detected. All trematodes were detached. Intestinal peristalsis and sucker movement was no longer visible. Males barely moved and showed only twitching, while females displayed more twitching movements than males. Trematodes had a stretched or slightly ventrally curved shape. Almost no eggs were detectable.

After 24 hours of incubation with 100 µM of compound 18 of this invention, no couples could be detected. All trematodes were detached. Both intestinal peristalsis and sucker movement were no longer detectable. The trematodes rarely showed slightly twitching movements. Males and females are strongly ventrally curved. Almost no eggs were detectable.

After 24 hours of incubation with 20 µM of compound 41 of this invention, 4-6 couples could be detected in each of the groups. All trematodes were detached. Intestinal peristalsis was slowed down, and sucker movement was no longer visible. Trematodes moved only slightly and with twitching movements. Almost no eggs were detectable.

After 24 hours of incubation with 100 µM of compound 2 of this invention, in two of the groups each one couple was detected. All trematodes were detached. Both intestinal peristalsis and sucker movement were no longer detectable. Males and females had a highly bent and twisted appearance. Males as well as females showed bulging/swellings of the intestinal tract. Trematodes moved only slightly and with twitching movements. Almost no eggs were detectable.

Example 11

In Vitro-Treatment of Adult *S. Mansoni* Pairs with Compounds 41, 18 and 26 for 48 Hours In a second experimental setting, again three groups each (one group per well) with 8 pairs of adult *S. mansoni* each were incubated with the compound to be tested, however for 48 h in this experiment. As control served three groups which were either incubated with medium (M199) or medium and DMSO as solvent of the test substances. Evaluation was done visually using a microscope.

Results:

Couples of the control groups (only medium and DMSO control) were all paired after 48 hours and attached; all looked vital and normal and had a stretched shape. Intestinal peristalsis and sucker movement was detectable. Egg production was also normal. See FIG. 1.

After 48 hours of incubation with 20 µM of compound 41 of this invention, no couples could be observed in any of the groups. All trematodes were detached. Intestinal peristalsis was reduced, and sucker movement were no longer detectable. Single trematodes showed slightly twitching movements, while the rest was non-motile. Many male species were bent towards the dorsal site. No eggs were produced.

After 48 hours of incubation with 100 µM of compound 41 of this invention, no couples could be observed in any of the groups. Some of the worms were already dead, while others were dying. A few worms showed slight, spontaneous twitching. Worms mostly had a stretched shape. No eggs were detectable.

After 48 hours of incubation with 20 µM of compound 18 of this invention, no couples could be observed in any of the groups, and all worms were dead. Females were strongly twisted and bent, while males displayed a ventrally bent shape. No eggs were detectable. See FIG. 2.

After 48 hours of incubation with 100 µM of compound 18 of this invention, no couples could be observed in any of the groups and all worms were dead. Females were strongly twisted and bent, while males displayed a ventrally bent shape, some of them being entirely curled up. No eggs were detectable. See FIG. 2.

After 48 hours of incubation with 20 µM of compound 2 of this invention, no couples could be observed in any of the groups. All trematodes were detached. Intestinal peristalsis was reduced, and sucker movement were no longer detectable. The trematodes barely moved, and all were curled in ventral direction. No eggs were detectable.

After 48 hours of incubation with 100 µM of compound 2 of this invention, no couples could be observed in any of the groups. All trematodes were dead. Females were strongly curved and twisted, while males were curled in ventral direction. No eggs were detectable.

Example 12

Activity of Compounds Against *Trypanosoma Brucei*

Compounds 18 and 41 were assessed at the London School of Hygiene and Tropical Medicine in vitro with respect to their efficacy against the parasite *Trypanosoma brucei brucei* S427. Compound 18 showed an $IC_{50}$ of 0.93 µM, compound 41 showed an $IC_{50}$ of 3.58 µM. This example confirms that compounds of the present invention possess a very broad range of possible applications.

The invention claimed is:
1. A method for the treatment of infections of protozoa and trematodes comprising administering an effective amount of a compound to a patient in need thereof, wherein the compound is selected from the group consisting of:
   17α-[(2-Hydroxynaphth-1-yl)-methylamino]-3-methoxy-estra-1,3,5(10)-triene (17),
   17β-[(3-Hydroxynaphth-2-yl)-methylamino]-3-methoxy-estra-1,3,5(10)-triene (18),
   17β-[(2-Hydroxynaphth-1-yl)-methylamino]-3-methoxy-estra-1,3,5(10)-triene hydroperchlorate (19),
   16α-[(3-Hydroxy-naphth-2-yl)-methylamino]-17β-hydroxy-3-methoxy-estra-1,3,5(10)-triene (32),
   16α-[(3-Hydroxy-naphth-2-yl)-methylamino]-17α-hydroxy-3-methoxy-estra-1,3,5(10)-triene (36), and
   17α-[(3-Hydroxy-naphth-2-yl)-methylamino]-3-methoxy-estra-1,3,5(10)-triene 41).
2. The method according to claim 1, wherein the infection is characteristic of schistosomiasis or malaria.

* * * * *